(12) United States Patent
Barden et al.

(10) Patent No.: US 12,129,295 B2
(45) Date of Patent: *Oct. 29, 2024

(54) ANTI P2X7 RECEPTOR ANTIBODIES AND FRAGMENTS THEREOF

(71) Applicant: BIOSCEPTRE (AUST) PTY LTD, North Ryde (AU)

(72) Inventors: Julian Alexander Barden, North Ryde (AU); Neil Brewis, Stevenage (GB); Philip Jones, Cambridge (GB); Steven Grant, Cambridge (GB)

(73) Assignee: BIOSCEPTRE (AUST) PTY LTD, North Ryde (AU)

( * ) Notice: Subject to any disclaimer, the term of this patent is extended or adjusted under 35 U.S.C. 154(b) by 715 days.

This patent is subject to a terminal disclaimer.

(21) Appl. No.: 17/198,179

(22) Filed: Mar. 10, 2021

(65) Prior Publication Data

US 2022/0315652 A1 Oct. 6, 2022

Related U.S. Application Data

(63) Continuation of application No. 16/032,973, filed on Jul. 11, 2018, now Pat. No. 10,988,532, which is a continuation of application No. 15/599,396, filed on May 18, 2017, now Pat. No. 10,053,508, which is a continuation of application No. 14/671,254, filed on Mar. 27, 2015, now Pat. No. 9,688,771, which is a continuation of application No. 13/391,619, filed as application No. PCT/AU2010/001070 on Aug. 20, 2010, now Pat. No. 9,127,059.

(30) Foreign Application Priority Data

Aug. 20, 2009 (AU) .............................. 2009903928

(51) Int. Cl.
*C07K 16/28* (2006.01)
*C07K 16/30* (2006.01)

(52) U.S. Cl.
CPC .............. *C07K 16/28* (2013.01); *C07K 16/30* (2013.01); *C07K 2317/34* (2013.01); *C07K 2317/565* (2013.01); *C07K 2317/567* (2013.01); *C07K 2317/569* (2013.01); *C07K 2317/74* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,133,434 A | 10/2000 | Buell et al. | |
| 6,303,338 B1 | 10/2001 | Ni et al. | |
| 6,306,393 B1 | 10/2001 | Goldenberg et al. | |
| 6,329,503 B1 | 12/2001 | Afar et al. | |
| 6,709,832 B1 | 3/2004 | Von Knebel Doeberitz | |
| 7,183,064 B1 | 2/2007 | Slater et al. | |
| 7,326,415 B2 | 2/2008 | Barden et al. | |
| 7,531,171 B2 | 5/2009 | Barden et al. | |
| 7,767,789 B2 | 8/2010 | Gorodeski et al. | |
| 7,888,473 B2 | 2/2011 | Barden et al. | |
| 8,067,550 B2 | 11/2011 | Barden et al. | |
| 8,080,635 B2 | 12/2011 | Barden et al. | |
| 8,293,491 B2 | 10/2012 | Gidley-Baird et al. | |
| 8,399,617 B2 | 3/2013 | Barden et al. | |
| 8,440,186 B2 | 5/2013 | Barden et al. | |
| 8,597,643 B2 | 12/2013 | Barden et al. | |
| 9,127,059 B2 | 9/2015 | Barden et al. | |
| 9,688,771 B2 | 6/2017 | Barden et al. | |
| 10,053,508 B2 | 8/2018 | Barden et al. | |
| 10,988,532 B2 | 4/2021 | Barden et al. | |
| 2004/0142342 A1 | 7/2004 | Barden et al. | |
| 2007/0020706 A1 | 1/2007 | Gorodeski et al. | |
| 2007/0248963 A1 | 10/2007 | Slater et al. | |
| 2008/0131438 A1 | 6/2008 | Barden et al. | |
| 2008/0227122 A1 | 9/2008 | Barden et al. | |
| 2010/0036101 A1 | 2/2010 | Gidley-Baird et al. | |
| 2011/0111431 A1 | 5/2011 | Slater et al. | |

FOREIGN PATENT DOCUMENTS

| | | |
|---|---|---|
| AU | 64184/98 B2 | 10/1998 |
| CA | 2284859 C | 1/2007 |
| EP | 1006186 A1 | 10/1998 |
| WO | WO 91/002078 A1 | 2/1991 |
| WO | WO 92/016558 A1 | 10/1992 |
| WO | WO 95/033048 A2 | 12/1995 |
| WO | WO 97/006256 A2 | 2/1997 |
| WO | WO 97/041222 A1 | 11/1997 |
| WO | WO 98/042835 A1 | 10/1998 |
| WO | PCT/AU00/000363 | 4/2000 |
| WO | WO 00/050458 A1 | 8/2000 |
| WO | PCT/AU01/001614 | 12/2000 |
| WO | WO 01/006259 A1 | 1/2001 |
| WO | WO 01/030964 A2 | 5/2001 |

(Continued)

OTHER PUBLICATIONS

U.S. Appl. No. 60/686,770, filed Jun. 2, 2005, Gorodeski et al.
U.S. Appl. No. 60/778,993, filed Mar. 3, 2006, Gorodeski et al.
Ayyanathan et al., "Cloning and chromosomal localisation of the human P2Y1 purinoceptor," Biochem Biophys Res Commun, 218(3):783-788, (1996).
Barden et al., "Specific detection of non-functional human P2X7 receptos in HEK293 cells and B-lymphocytes," FEBS Letters, 538:159-162, (2003).
Bird et al., "Single-Chain Antigen-Binding Proteins," Science, 242(4877):423-426, (1988).
Bowler et al., "Identification and cloning of human P2U purinoceptor present in osteoclastoma, bone, and osteoblasts," J Bone Min Res, 10(7):1137-1145, (1995).

(Continued)

*Primary Examiner* — Brad Duffy
(74) *Attorney, Agent, or Firm* — Alston & Bird LLP

(57) ABSTRACT

The invention relates to an antigen binding site for binding to a P2X$_7$ receptor, the antigen binding site being defined by general formula 1: FR1-CDR1-FR2-CDR2-FR3-CDR3-FR4.

16 Claims, 47 Drawing Sheets

Specification includes a Sequence Listing.

(56) References Cited

FOREIGN PATENT DOCUMENTS

| WO | PCT/AU02/000061 | | 1/2002 | | |
| WO | WO 02/057306 A1 | | 7/2002 | | |
| WO | PCT/AU02/001204 | | 9/2002 | | |
| WO | WO 02/102972 A2 | | 12/2002 | | |
| WO | WO 03/020762 A1 | | 3/2003 | | |
| WO | WO 04/092384 A2 | | 10/2004 | | |
| WO | WO-2006017538 A2 | * | 2/2006 | ............ | C07K 16/40 |
| WO | WO-2006085961 A2 | * | 8/2006 | ............ | C07K 16/24 |
| WO | WO 06/133508 A1 | | 12/2006 | | |
| WO | WO 07/056507 A1 | | 5/2007 | | |
| WO | PCT/AU07/001540 | | 10/2007 | | |
| WO | PCT/AU07/001541 | | 10/2007 | | |
| WO | WO 08/043145 A2 | | 4/2008 | | |
| WO | WO 08/043146 A1 | | 4/2008 | | |
| WO | PCT/AU08/001364 | | 9/2008 | | |
| WO | PCT/AU08/001365 | | 9/2008 | | |
| WO | WO 09/033233 A1 | | 3/2009 | | |
| WO | WO 09/033234 A1 | | 3/2009 | | |
| WO | PCT/AU09/000869 | | 7/2009 | | |
| WO | PCT/AU10/001070 | | 8/2010 | | |
| WO | PCT/AU10/001741 | | 12/2010 | | |
| WO | WO 11/020155 A1 | | 2/2011 | | |
| WO | WO 11/075789 A1 | | 6/2011 | | |
| WO | PCT/AU11/001166 | | 9/2011 | | |
| WO | PCT/AU12/000795 | | 7/2012 | | |
| WO | WO 10/000041 A1 | | 5/2021 | | |

OTHER PUBLICATIONS

Buell et al., "P2X receptors: am emerging channel family," Eur J Neurosci., 8:2221-2228, (1996).
Buell et al., "Blockade of Human P2X7 Receptor Function With a Monoclonal Antibody," Blood, 92:3521-3528, (1998).
Burnstock et al., "P2 Purinergic Receptors: Modulation of Cell Function and Therapeutic Potential," J Pharm Exp Therap, 295:862-869, (2000).
Chan et al., "Localization of P2X1 purinoceptors by autoradiography and immunohistochemistry in rat kidneys," Am J Physiol Renal Physiol, 274(4(2)): F799-804, (1998).
Cheewatrakoolpong et al., "Identification and characterization of splice variants of the human P2X7 ATP channel," Biochem Biophys Res Comm., 332:17-27, (2005).
Chessell et al., "Dynamics of P2X7 receptor pore dilation: pharmacological and functional consequences," Drug Dev Res, 53(2-3):60-65, (2001).
Communi et al., "Cloning and Functional Expression of a Human Uridine Nucleotide Receptor," J Biol Chem, 270(52): 30849-30852, (1995).
Communi et al., "Cloning, Functional Expression and Tissue Distribution of the Human P2Y6 Receptor," Biochem Biophys Res Commun, 222:303-308, (1996).
Dangl et al., "Rapid Isolation of Cloned Isotype Switch Variants Using Fluorescence Activated Cell Sorting," Cytometry, 2:395-401, (1982).
DeRisi et al., "Exploring the Metabolic and Genetic Control of Gene Expression on a Genomic Scale," Science, 278: 680-686, (1997).
Di Virgilio et al., "Responses of mouse lymphocytes to extracellular adenosine 5'triphosphaste (ATP)," J Immunol 143:1955-1960, (1989).
Di Virgiolio et al., "Purinergic P2X7 receptor: a pivotal role in inflammation and immunomodulation," Drug Dev Res, 45:207-213, (1998).
Dixon et al., "Extracellular nucleotides stimulate proliferation in MCF-7 breast cancer cells via P2-purinoceptors," Br J Cancer, 75(1):34-39, (1997).
Dubyak et al., "Signal transduction via P2-purinergic receptors for extracellular ATP and other nucleotides," Am. J Physiol 265:C577-C606, (1993).
Feng et al., "A truncated P2X7 receptor variant (P2X7-j) endogenously expressed in cervical cancer cells antagonizes the full-length P2X7 receptor through hetero-oligomerization," J Biol Chem, 281:17228-17237, (2006).
Feng et al., "ATP stimulates GRK-3 phosphorylation and 3-arrestin-2-dependent internalization of P2X7 receptor," Am J Physiol Cell Physiol, 288:C1342-C1356, (2005).
Feng et al., "Endogenously Expressed Truncated P2X, Receptor Lacking the C-Terminal (P2X7-RTr) is Preferentially Upregulated in Epithelial Cancer Cells and Fails to Mediate Ligand-Induced Pore Formation and Apoptosis," 10th Symposium European Society for the Study of Purine and Pyrimidine Metabolism in Man, Abstract and Program, Jun. 8-11, 2005.
Feng et al., "Endogenously Expressed Truncated P2X7 Receptor Lacking the C-Terminus is Preferentially Upregulated in Epithelial Cancer Cells and Fails to Mediate Ligand-Induced Pore Formation and Apoptosis," Nucleosides, Nucleotides and Nucleic Acids, 2006;25 (9-11): 1271-6.
Ferrari et al., "P2Z purinoreceptor ligation induces activation of caspases with distinct roles in apoptotic and necrotic alterations of cell death," FEBS Lett., 447:71-75, (1999).
Ferrari et al., "ATP-mediated cytoxicity in microglial cells," Neuropharmacology, 36 (9):1295-1301, (1997).
Foster et al., "Cellular and molecular pathology of prostate cancer precursors," Scand J Urol Nephrol Suppl.,34(205):19-43, (2000).
Galfre et al., "Antibodies to major histocompatability antigens produced by hybrid cell lines," Nature, 266:550-552, (1977).
Galfre et al., "Rat x rat hybrid myelomas and a monoclonal anti-Fd portion of mouse IgG," Nature, 277:131-133, (1979).
Gefter et al., "A simple method for polyethylene glycol-promoted hybridization of mouse myeloma cells," Somatic Cell Genet., 3(2):231, (1977).
GenBank: Accession No. Y09561, versions Y09561.1, "H. sapiens mRNA for P2X7 receptor". [Retrieved from the Internet May 24, 2011 : <URL: http://www.ncbi.nlm.nih.gov/nuccore/y09561 >].
Georgiou et al., "Human Epidermal and Monocyte-Derived Langerhans Cells Express Functional P2X7 Receptors," J Invest Dermatology, 125:482-490, (2005).
Giusti et al., "Somatic diversification of S107 from an antiphosphocholine to an anti-DNA autoantibody is due to a single base change in its heavy chain variable region," PNAS, 84:2926-2930, (1987).
Greenbaum et al., "Comparing protein abundance and mRNA expression levels on a genomic scale," Genome Biology, 4(9):117.1-117.8, (2003).
Greig et al., "Expression of Purinergic Receptors in Non-melanoma Skin Cancers and Their Functional Roles in A431 Cells," J Invest Dermatol, 121:315-327, (2003).
Groschel-Stewart et al., "Localisation of P2X5 and P2X7 receptors by immunohistochemistry in rat stratified squamous epithelia," Cell Tissue Res, 296:599-605, (1999).
Gu et al., "A Glu-496 to Ala Polymorphism leads to loss of function of the human P2X7 receptor," J Biol Chem, 276(14):11135-11142, (2001).
Gu et al., "An Arg307 to Gln Polymorphism within the ATP-binding Site Causes Loss of Function of the Human P2X7 Receptor," J Biol Chem, 279 (30):31287-31295, (2004).
Gussow et al., "Humanization of Monoclonal Antibodies," Methods in Enzymology, 203:99-121, (1991).
Hansen et al., "Structural Motif and Characteristics of the Extracellular Domain of P2X Receptors," Biochem and Biophys Res Comm, 236(3):670-675, (1997).
Hansen et al., "The distribution of single P (2 x 1)—receptor clusters on smooth muscle cells in relation to nerve varicosities in the rat urinary bladder," J Neurocytol, 27(7): 529-539, (1998).
Holliger et al., "'Diabodies': Small bivalent and bispecific antibody fragments," Proc. Natl. Acad Sci. USA, 90:6444-6448, (1993).
Hopfner et al., "Expression of functional P2-purinergic receptors in primary cultures of human colorectal carcinoma cells," Biochem and Biophys Res Comm, 251:811-817, (1998).
Humphrey, "Gleason grading and prognostic factors in carcinoma of the prostate," Modern Pathology, 17:292-306, (2004).
Huston et al., "Protein engineering of antibody binding sites: Recovery of specific activity in an anti-digoxin single-chain Fv analogue produced in Escherichia coli," Proc. Natl. Acad. Sci. USA, 85:5879-5883, (1988).

(56) References Cited

OTHER PUBLICATIONS

Jacob et al., "Cytogenetic Profile of Chronic Myeloid Leukemias," Indian J Cancer, 39(2):61-65, (2002).
Jameison et al., "Extracellular ATP causes loss of L-selectin from human lymphocytes via occupancy of P2Z purinoceptors," J Cell Physiol, 166:637-642 (1996).
Janssens et al., "Effects of extracellular nucleotides and nucleosides on prostate carcinoma cells," Br J Pharmacol., 132: 536-46, (2001).
Jantzen et al., "Evidence for Two Distinct G-protein-coupled ADP Receptors Mediating Platelet Activation," Thromb and Haemost, 81:111-117, (1999).
Jones, "Critically assessing the state-of-the-art in protein structure prediction," Pharmacogenomics Journal, 1:126-134, (2001).
Katzur et al., "Expression and responsiveness of P2Y2 receptors in human endometrial cancer cell lines," J Clin Endocrinol Metab., 84(11): 4085-4091, (1999).
Kennedy et al., "The discovery and development of P2 receptor subtypes," J Auto Nerv Syst, 81:158-163, (2000).
Kim et al., "Differential Assembly of Rat Purinergic P2X7 Receptor in Immune Cells of the Brain and Periphery," J Biol Chem, 276(26):23262-23267, (2001).
King et al., "Metabotropic receptors for ATP and UTP: exploring the correspondence between native and recombinant nucleotide receptors," TiPS, 19: 506-514, (1998).
Kishore et al., "Cellular localisation of P2Y2 purinoceptor in rat renal inner medulla and lung," Am J Physiol Renal Physiol, 278: F43-F51, (2000).
La Sala et al., "Alerting and tuning the immune response by extracellular Nucleotides," J Leukoc Biol, 73:339-343, (2003).
Lee et al., "P2X receptor immunoreactivity in the male genital organs of the rat," Cell Tissue Res, 300(2): 321-330, (2000).
Li et al., "P2X7 Receptor: A Novel Biomarker of Uterine Epithelial Cancers," Cancer Epidemiol Biomarkers Prev, 15(10):1906-1913, (2006).
Mager et al., "Prediction of the confirmation of the human P2X7 receptor," Letts Drug Des Discov, 3(10):675-682, (2006).
Maier et al., "Cloning of P2Y6 cDNAs and Identification of a Pseudogene: Comparison of P2Y Receptor Subtype Expression in Bone and Brain Tissues," Biochem and Biophys Res Comm, 237:297-302, (1997).
Mariuzza et al., "The structural basis of antigen-antibody recognition," Annual Review of Biophysics and Biophysical Chemistry, 16:139-159, (1987).
Mauro et al., "Chronic myelogenous leukaemia," Curr Opin Oncol, 13(1):3-7, (2001).
Meeker et al., "An additional breakpoint region in the BCL-1 locus associated with the t(11;14)(q13;q32) translocation of B-lymphocytic malignancy," Blood, 74:1801-1806, (1989).
Nawa et al., "Frequent loss of expression or aberrant alternative splicing of P2XM, a p53-inducible gene, in soft-tissue tumours," Br J Cancer, 80(8):1185-89, (1999).
Ngo et al "Computational complexity, protein structure prediction, and the Levinthal paradox," In Merz and Le Grand (eds), The protein folding problem and tertiary structure prediction, Birkhauser: Boston, pp. 491-495, (1994).
Nihei et al., "Pharmacologic properties of P2z/P2X7 receptor characterized in murine dendritic cells: role on the induction of apoptosis", Blood, 96(3)996-1005, (2000).
Parr et al., "Cloning and expression of a human P2U nucleotide receptor, a target for cystic fibrosis pharmacotherapy," Proc. Natl. Acad. Sci. USA, 91:3275-3279, (1994).
Paul, Fundamental Immunology, Lippincott Williams & Wilkins, p. 107, (1998).
Peng et al., "P2Z purinoceptor, a special receptor for apoptosis induced by ATP in human leukemic lymphocytes," Chinese Med J, 112(4):356-362, (1999).
Perou et al., "Distinctive gene expression patterns in human mammary epithelial cells and breast cancers," Proc. Natl. Acad. Sci. USA, 96:9212-9217, (1999).
Poljak et al., "Production and structure of diabodies," Structure, 2:1121-1123, (1994).
Ralevic et al., "Receptors for Purines and Pyrimidines," Pharmacol Rev., 50(3):413-492, (1998).
Rassendren et al., "The permeabilizing ATP receptor, P2X7: Cloning and expression of a human cDNA," J Biol Chem, 272(9):5482-5486, (1997).
Ray et al., "Purinergic receptor distribution in endothelial cells in blood vessels: a basis for selection of coronary artery grafts," Atherosclerosis, 162:55-61, (2002).
Romagnoli et al., "Recent progress in the discovery of antagonists acting at P2X7 receptor," Expert Opinions Ther. Patents, 15(3):271-287, (2005).
Rudikoff et al., "Single amino acid substitution altering antigen-binding specificity," PNAS, 79:1979-1983, (1982).
Sauer et al., "Calcium-dependence of hydrogen peroxide-induced c-fos expression and growth stimulation of multicellular prostate tumour spheroids," FEBS Lett, 419: 201-205, (1997).
Schultze-Mosgau et al., "Characterization of calcium-mobilizing, purinergic P2Y2 receptors in human ovarian cancer cells," Mol Human Reproduct., 6(5): 435-442, (2000).
Slater et al. "Early prostate cancer detected using expression of non-functional cytolytic P2X7 receptors," Histopathology, 44:206-215, (2004).
Slater et al., "Detection of preneoplasia in histologically normal prostate biopsies," Prost Cancer Prostat Dis, 4:92-96, (2001).
Slater et al., "Differentiation between cancerous and normal hyperplastic lobules in breast lesions," Breast Cancer Res Treat, 83:1-10, (2004).
Slater et al., "Expression of the apoptotic calcium channel P2X7 in the glandular epithelium is a marker for early prostate cancer and correlates with increasing PSA levels," J Mol Histol., 36:159-165, (2005).
Slater et al., "Increased expression of apoptotic markers in melanoma," Melanoma Res, 13(2):137-145, (2003).
Slater et al., "Markers for the development of early prostate cancer," J Pathol, 199:368-377, (2003).
Sluyter et al., "Extracellular ATP increases cation fluxes in human erthrocytes by activation of the P2X7 receptor," J Biol Chem, 279(43):44749-44756, (2004).
Spieker-Polet et al., "Rabbit monoclonal antibodies: Generating a fusion partner to produce rabbit-rabbit hybridomas," Proc. Natl. Acad. Sci USA, 92:9348-9352, (1995).
Surprenant et al., "The cytosolic P2Z receptor for extracellular ATP identified as a P2X receptor (P2X7)," Science, 272:735-738, (1996).
Tockman et al., "Considerations in Bringing a Cancer Biomarker to Clinical Application," Cancer Res, 52:2711s-2718s, (1992).
Torres et al., "Hetero-oligomeric Assembly of P2X Receptor Subunits," J Biol Chem, 274(10):6653-6659, (1999).
Tosatto et al., "Large-Scale Prediction of Protein Structure and Function from Sequence," Current Pharmaceutical Design, 12:2067-2086, (2006).
U.S. Appl. No. 14/671,254, Non-Final Office Action mailed Oct. 3, 2016.
U.S. Appl. No. 14/671,254, Notice of Allowance mailed Feb. 23, 2017.
U.S. Appl. No. 14/671,254, Requirement for Restriction/Election mailed Jun. 16, 2016.
U.S. Appl. No. 15/599,396, Notice of Allowance mailed Apr. 11, 2018.
U.S. Appl. No. 16/032,973, Non-Final Office Action mailed Aug. 26, 2020.
U.S. Appl. No. 16/032,973, Notice of Allowance mailed Dec. 10, 2020.
Urano et al., "Cloning of P2XM, a novel human P2X receptor gene regulated by p53," Cancer Res, 57:3281-87, (1997).
Virginio et al., "Kinetics of cell lysis, dye uptake and permeability changes in cells expressing the rat P2X7 receptor," J Physiol., 519(2):335-346, (1999).
Von Kugelgen et al., "Molecular Pharmacology of P2Y-receptors," Naunyn Scmiedebergs Arch Pharmacol, 362:(4-5)310-323, (2000).
Vulchanova et al., "Immunohistochemical study of the P2X2 and P2X3 receptor subunits in rat and monkey sensory neurons and their central terminals," Neuropharmacol, 36(9):1229-1242, (1997).

(56) References Cited

OTHER PUBLICATIONS

Wagstaff et al., "Extracellular ATP activates multiple signalling pathways and potentiates growth factor-induced c-fos gene expression in MCF-7 breast cancer cells," Carcinogenesis 21(12):2175-2181, (2000).
Wang et al., "P2X7 receptor-mediated apoptosis of human cervical epithelial cells," Am. J Physiol, 287:1349-1358, (2004).
Ward et al., "Binding activities of a repertoire of single immunoglobulin variable domains secreted from *Escherichia coli*," Nature 341:544-546, (1989).
Wasilenko et al., "Calcium signaling in prostate cancer cells: Evidence for multiple receptors and enhanced sensitivity to bombesin/GRP," The Prostate 30:167-173 (1997).
Wells "Additivity of mutational effects in proteins," Biochemistry, 29(37):8509-8517, (1990).
White et al., "P2Y purinergic receptors regulate the growth of human melanomas," Cancer Letts, 224:81-91, (2005).
Wiley et al., "A single nucleotide polymorphism is associated with loss of function of the monocyte P2X7 receptor," Blood, 96(11):17, (2000). Abstract.
Wiley et al., "An Ile-568 to Asn polymorphism prevents normal trafficking and function of the human P2X7 receptor," J Biol Chem 278 (19):17108-17113, (2003).
Wiley et al., "Genetic polymorphisms of the human P2X7 receptor and relationship to function," Drug Dev Res, 53(2-3):72-76, (2001).
Williams et al., "Purinergic and pyrimidinergic receptors as potential drug targets," Biochem Pharm, 59:1173-1184, (2000).
Winkler et al., "Changing the antibody binding specificity by single point mutations of an Anti-p24 (HIV-1) antibody," Journal of Immunology, 165:4505-4514, (2000).
Worthington et al., "Point mutations confer loss of ATP-induced human P2X7 receptor function," FEBS Lett, 512:43-46, (2002).
Wurl et al., "High prognostic significance of Mdm2/p53 co-overexpression in soft tissue sarcomas of the extremities," Oncogene, 16(9):1183-85, (1998).
U.S. Appl. No. 15/599,396, filed May 18, 2017, U.S. Pat. No. 10,053,508, Issued.
U.S. Appl. No. 14/671,254, filed Mar. 27, 2015, U.S. Pat. No. 9,688,771, Issued.
U.S. Appl. No. 13/391,619, filed Feb. 21, 2012, U.S. Pat. No. 9,127,059, Issued.
U.S. Appl. No. 16/032,973, filed Jul. 11, 2018, U.S. Pat. No. 10,988,532, Issued.
U.S. Appl. No. 10/019,356, filed May 21, 2002, U.S. Pat. No. 7,183,064, Issued.
U.S. Appl. No. 10/622,313, filed Jul. 17, 2003, U.S. Pat. No. 7,326,415, Issued.
U.S. Appl. No. 10/450,205, filed Nov. 14, 2003, US 2004/0067542, Abandoned.
U.S. Appl. No. 11/566,472, filed Dec. 4, 2006, US 2007-0248963, Abandoned.
U.S. Appl. No. 11/968,607, filed Jan. 2, 2008, U.S. Pat. No. 7,531,171, Issued.
U.S. Appl. No. 12/043,083, filed Mar. 5, 2008, US 2008/0227122, Abandoned.
U.S. Appl. No. 12/417,989, filed Apr. 3, 2009, U.S. Pat. No. 7,888,473, Issued.
U.S. Appl. No. 12/445,258, filed Apr. 10, 2009, US 2010-0036101, Abandoned.
U.S. Appl. No. 12/445,273, filed Apr. 10, 2009, U.S. Pat. No. 8,067,550, Issued.
U.S. Appl. No. 12/677,795, filed Mar. 11, 2010, U.S. Pat. No. 8,293,491, Issued.
U.S. Appl. No. 12/677,799, filed Jul. 1, 2010, U.S. Pat. No. 8,440,186, Issued.
U.S. Appl. No. 12/878,865, filed Sep. 9, 2010, US 2011-0111431, Abandoned.
U.S. Appl. No. 12/975,341, filed Dec. 21, 2010, U.S. Pat. No. 8,080,635, Issued.
U.S. Appl. No. 13/002,647, filed Jan. 4, 2011, U.S. Pat. No. 8,597,643, Issued.
U.S. Appl. No. 13/298,222, filed Nov. 16, 2011, U.S. Pat. No. 8,399,617, Issued.
U.S. Appl. No. 13/518,382, filed Jun. 21, 2012, U.S. Pat. No. 8,835,609, Issued.
U.S. Appl. No. 13/626,833, filed Sep. 25, 2012, U.S. Pat. No. 8,658,385, Issued.
U.S. Appl. No. 13/766,630, filed Feb. 13, 2013, U.S. Pat. No. 8,709,425, Issued.
U.S. Appl. No. 13/821,555, filed Mar. 7, 2013, U.S. Pat. No. 9,562,094, Issued.
U.S. Appl. No. 13/841,692, filed Mar. 15, 2013, U.S. Pat. No. 9,181,320, Issued.
U.S. Appl. No. 14/067,873, filed Oct. 30, 2013, U.S. Pat. No. 9,328,155, Issued.
U.S. Appl. No. 14/129,240, filed Dec. 24, 2013, U.S. Pat. No. 9,566,318, Issued.
U.S. Appl. No. 14/218,935, filed Mar. 18, 2014, US 2014-0323693, Abandoned.
U.S. Appl. No. 14/456,898, filed Aug. 11, 2014, U.S. Pat. No. 9,428,587, Issued.
U.S. Appl. No. 14/726,391, filed May 29, 2015, U.S. Pat. No. 9,663,584, Issued.
U.S. Appl. No. 14/877,715, filed Oct. 7, 2015, U.S. Pat. No. 9,944,701, Issued.
U.S. Appl. No. 15/085,929, filed Mar. 30, 2016, US 2016-0199442, Pending.
U.S. Appl. No. 15/387,421, filed Dec. 21, 2016, US 2017-0232085, Pending.
U.S. Appl. No. 15/399,337, filed Jan. 5, 2017, US 2017-0157229, Pending.
U.S. Appl. No. 15/498,301, filed Nov. 16, 2017, US 2017/0327592, Pending.
U.S. Appl. No. 15/910,987, filed Mar. 2, 2018, US 2018-0265580, Pending.

\* cited by examiner

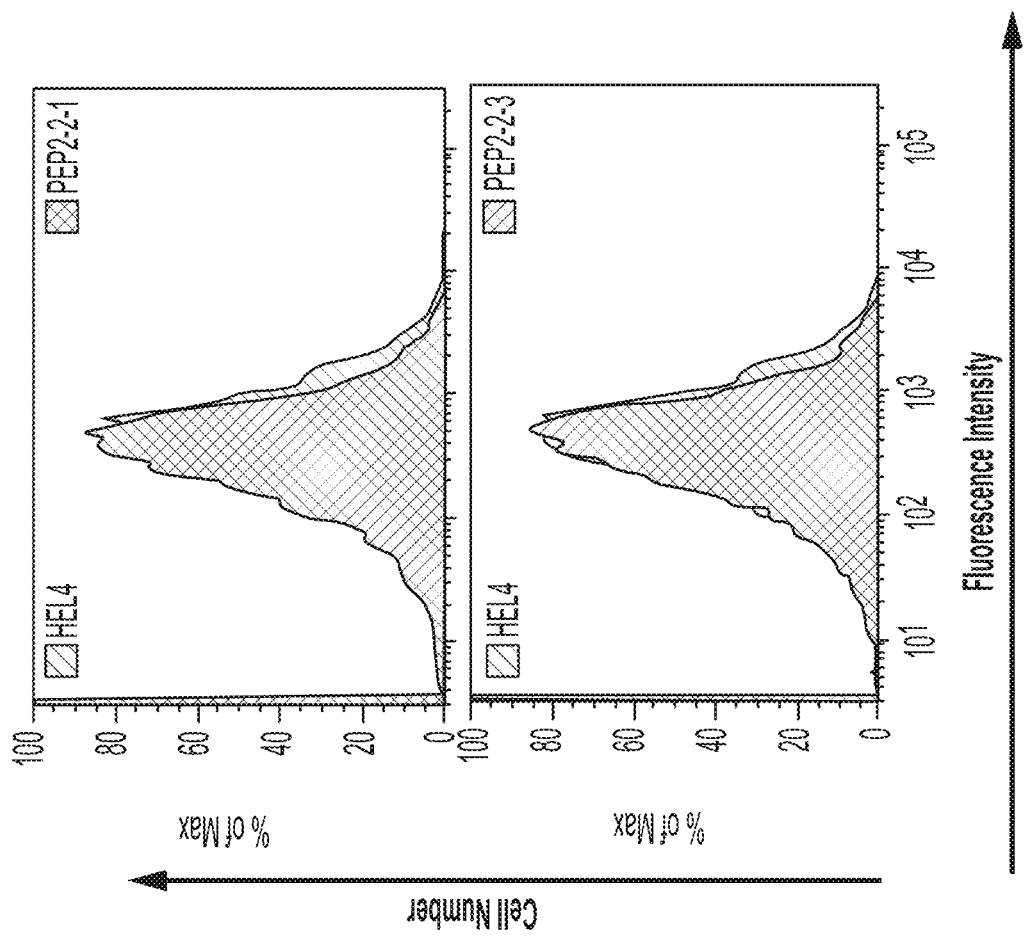
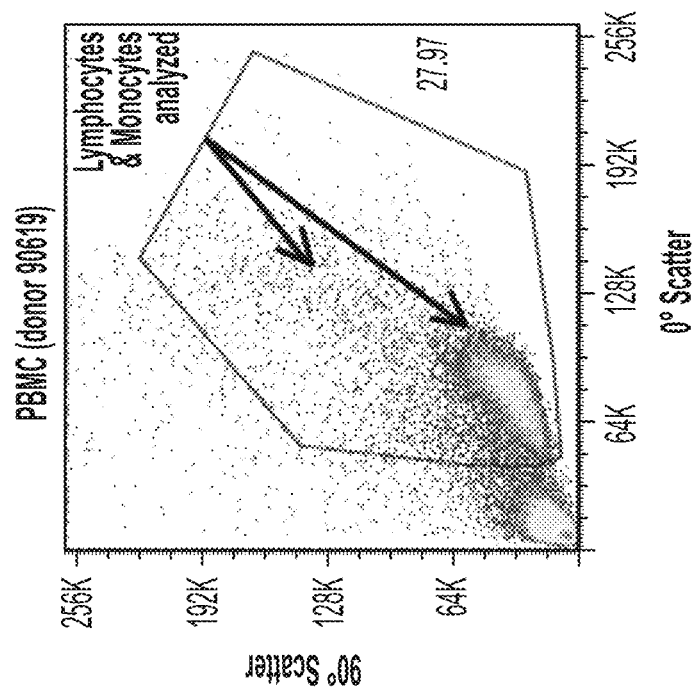
Fig. 32

Fig. 41

SEQ ID NO:1

```
1    MPACCSCSDV FQYETNKVTR IQSMNYGTIK WFFHVIIFSY VCFALVSDKL YQRKEPVISS
61   VHTKVKGIAE VKEEIVENGV KKLVHSVFDT ADYTFPLQGN SFFVMTNFLK TEGQEQRLCP
121  EYPTRRTLCS SDRGCKKGWM DPQSKGIQTG RCVVHEGNQK TCEVSAWCPI EAVEEAPRPA
181  LLNSAENFTV LIKNNIDFPG HNYTTRNILP GLNITCTFHK TQNPQCPIFR LGDIFRETGD
241  NFSDVAIQGG IMGIEIYWDC NLDRWFHHCR PKYSFRRLDD KTTNVSLYPG YNFRYAKYYK
301  ENNVEKRTLI KVFGIRFDIL VFGTGGKFDI IQLVVYIGST LSYFGLAAVF IDFLIDTYSS
361  NCCRSHIYPW CKCCQPCVVN EYYYRKKCES IVEPKPTLKY VSFVDESHIR MVNQQLLGRS
421  LQDVKGQEVP RPAMDFTDLS RLPLALHDTP PIPGQPEEIQ LLRKEATPRS RDSPVWCQCG
481  SCLPSQLPES HRCLEELCCR KKPGACITTS ELFRKLVLSR HVLQFLLLYQ EPLLALDVDS
541  TNSRLRHCAY RCYATWRFGS QDMADFAILP SCCRWRIRKE FPKSEGQYSG FKSPY
```

Fig. 42

SEQ ID NO:2

```
1    MPACCSCSDV FQYETNKVTR IQSMNYGTIK WFFHVIIFSY VCFALVSDKL YQRKEPVISS
61   VHTKVKGIAE VKEEIVENGV KKLVHSVFDT ADYTFPLQGN SFFVMTNFLK TEGQEQRLCP
121  EYPTRRTLCS SDRGCKKGWM DPQSKGIQTG RCVVHEGNQK TCEVSAWCPI EAVEEAPRPA
181  LLNSAENFTV LIKNNIDFPG HNYTTRNILP GLNITCTFHK TQNPQCPIFR LGDIFRETGD
241  NFSDVAIQGG IMGIEIYWDC NLDRWFHHCR PKYSFRRLDD KTTNVSLYPG YNFRYAKYYK
301  ENNVEKRTLI KVFGIRFDIL VFGTGGKFDI IQLVVYIGST LSYFGLAAVF IDFLIDTYSS
361  NCCRSHIYPW CKCCQPCVVN EYYYRKKCES IVEPKPTLKY VSFVDESHIR MVNQQLLGRS
421  LQDVKGQEVP RPAMDFTDLS RLPLALHDTP PIPCQPEEIQ LLRKEATPRS RDSPVWCQCG
481  SCLPSQLPES HRCLEELCCR KKPGACITTS ELFRKLVLSR HVLQFLLLYQ EPLLALDVDS
541  TNSRLRHCAY RCYATWRFGS QDMADFAILP SCCRWRIRKE FPKSEGQYSG FKSPY
```

Fig. 43

SEQ ID NO:3

```
  1    MPACCSCSDV FQYETNKVTR IQSMNYGTIK WFFHVIIFSY VCFALVSDKL YQRKEPVISS
 61    VHTKVKGIAE VKEEIVENGV KKLVHSVFDT ADYTFPLQGN SFFVMTNFLK TEGQEQRLCP
121    EYPTRRTLCS SDRGCKKGWM DPQSKGIQTG RCVVHEGNQK TCEVSAWCPI EAVEEAPRPA
181    LLNSAENFTV LIKNNIDFPG HNYTTRNILP GLNITCTFHK TQNPQCPIFR LGDIFRETGD
241    NFSDVAIQGG IMGIEIYWDC NLDRWFHHCR PKYSFRRLDD KTTNVSLYPG YNFRYAKYYK
301    ENNVEKRTLI KVFGIRFDIL VFGTGGKFDI IQLVVYIGST LSYFGLAAVF IDFLIDTYSS
361    NCCRSHIYPW CKCCQPCVVN EYYYRKKCES IVEPKPTLKY VSFVDESHIR MVNQQLLGRS
421    LQDVKGQEVP RPAMDFTDLS RLPLALHDTP PIPCQPEEIQ LLRKEATPRS RDSPVWCQCG
481    SCLPSQLPES HRCLEELCCR KKPCACITTS ELFRKLVLSR HVLQFLLLYQ EPLLALDVDS
541    TNSRLRHCAY RCYATWRFGS QDMADFAILP SCCRWRIRKE FPKSEGQYSG FKSPY
```

Fig. 45A aattcgccgccaccatggagaccgacaccctgctgctgtgggtgctgctgctgtgggtgcccggatccaccggcgag
gtgcagctgttggagtctgggggaggcttggtacagcctggggggtccctgcgtctctcctgtgcagcctccggatt
cacctttcgtaatcatgatatgggggtgggtccgccaggctccagggaagggtctagagtgggtctcagctattagtg
gtagtggtggtagcacatactacgcaaactccgtgaagggccggttcaccatctcccgcgacaattccaagaacacg
ctgtatctgcaaatgaacagcctgcgtgccgaggacaccgcggtatattctgtgcggaaccgaagcctatggatac
ggagtttgactacaggagtccgggaaccctggtcaccgtctcgagcgctagcacccacacctgcccccctgccctg
ccccgagctgctgggcggacctagcgtgttcctgttccccccaagcctaaggacaccctgatgatcagcaggacc
cccgaagtgacctgcgtggtggtggatgtgagccacgaggaccctgaagtgaagttcaactggtacgtggacggcgt
ggaagtgcacaacgccaagaccaagcccagagaggagcagtacaacagcacctaccgcgtggtgtctgtgctgaccg
tgctgcaccaggattggctgaacggcaaggagtacaagtgcaaagtgagcaacaaggccctgcctgcccctatcgag
aaaaccatcagcaaggccaagggccagcctagagagcccaggtctacaccctgcctccctccagagatgagctgac
caagaaccaggtgtccctgacctgtctggtgaagggcttctaccccagcgacatcgccgtggagtgggagagcaacg
gccagcccgagaacaactacaagaccacccccctgtgctggacagcgatggcagcttcttcctgtactccaagctg
accgtggacaagagcagatggcagcagggcaacgtgttcagctgcagcgtgatgcacgaggccctgcacaatcacta
cacccagaagagtctgagcctgtcccctggcaagtgatagcggccgctcgagtctagagggcccgtttaaacccgct
gatcagcctcgactgtgccttctagttgccagccatctgttgtttgccctccccgtgccttccttgaccctggaa
ggtgccactcccactgtcctttcctaataaaatgaggaaattgcatcgcattgtctgagtaggtgtcattctattct
ggggggtggggtggggcaggacagcaaggggggaggattgggaagacaatagcaggcatgctggggatgcggtgggct
ctatggcttctgaggcggaaagaaccagctggggctctagggggtatcccacgcgccctgtagcggcgcattaagc
gcggcgggtgtggtggttacgcgcagcgtgaccgctacacttgccagcgccctagcgcccgctcctttcgctttctt
cccttcctttctcgccacgttcgccggcttccccgtcaagctctaaatcggggggctcccttagggttccgattta
gtgctttacggcacctcgaccccaaaaaacttgattagggtgatggttcacgtagtgggccatcgccctgatagacg
gtttttcgccctttgacgttggagtccacgttctttaatagtggactcttgttccaaactggaacaacactcaaccc
tatctcggtctattcttttgatttataagggattttgccgatttcggcctattggttaaaaaatgagctgatttaac
aaaaatttaacgcgaattaattctgtggaatgtgtgtcagttagggtgtggaaagtccccaggctccccagcaggca
gaagtatgcaaagcatgcatctcaattagtcagcaaccaggtgtggaaagtccccaggctccccagcaggcagaagt
atgcaaagcatgcatctcaattagtcagcaaccatagtcccgcccctaactccgcccatcccgcccctaactccgcc
cagttccgcccattctccgccccatggctgactaattttttttatttatgcagaggccgaggccgcctctgcctctg
agctattccagaagtagtgaggaggcttttttggaggcctaggcttttgcaaaaagctcccgggagcttgtatatcc
attttcggatctgatcaagagacaggatgaggatcgtttcgcatgattgaacaagatggattgcacgcaggttctcc
ggccgcttggtggagaggctattcggctatgactgggcacaacagacaatcggctgctctgatgccgccgtgttcc
ggctgtcagcgcaggggcgcccggttcttttttgtcaagaccgacctgtccggtgccctgaatgaactgcaggacgag
gcagcgcggctatcgtggctggccacgacgggcgttccttgcgcagctgtgctcgacgttgtcactgaagcgggaag
ggactggctgctattgggcgaagtgccggggcaggatctcctgtcatctcaccttgctcctgccgagaaagtatcca
tcatggctgatgcaatgcggcggctgcatacgcttgatccggctacctgcccattcgaccaccaagcgaaacatcgc

Fig. 45B atcgagcgagcacgtactcggatggaagccggtcttgtcgatcaggatgatctggacgaagagcatcaggggctcgc
gccagccgaactgtccgccaggctcaaggcgcgcatgcccgacggcgaggatctcgtcgtgacccatggcgatgcct
gcttgccgaatatcatggtggaaaatggccgcttttctggattcatcgactgtggccggctggtgtggcggaccgc
tatcaggacatagcgttggctaccgtgatattgctgaagagcttggcggcgaatgggctgaccgcttcctcgtgct
ttacggtatcgccgctcccgattcgcagcgcatcgccttctatcgccttcttgacgagttcttctgagcgggactct
ggggttcgaaatgaccgaccaagcgacgcccaacctgccatcacgagatttcgattccaccgccgccttctatgaaa
ggttgggcttcggaatcgttttccgggacgccggctggatgatcctccagcgcggggatctcatgctggagttcttc
gcccaccccaacttgtttattgcagcttataatggttacaaataaagcaatagcatcacaaatttcacaaataaagc
attttttttcactgcattctagttgtggtttgtccaaactcatcaatgtatcttatcatgtctgtataccgtcgacct
ctagctagagcttggcgtaatcatggtcatagctgtttcctgtgtgaaattgttatccgctcacaattccacacaac
atacgagccggaagcataaagtgtaaagcctggggtgcctaatgagtgagctaactcacattaattgcgttgcgctc
actgcccgctttccagtcgggaaacctgtcgtgccagctgcattaatgaatcggccaacgcgcggggagaggcggtt
tgcgtattgggcgctcttccgcttcctcgctcactgactcgctgcgctcggtcgttcggctgcggcgagcggtatca
gctcactcaaaggcggtaatacggttatccacagaatcaggggataacgcaggaaagaacatgtgagcaaaaggcca
gcaaaaggccaggaaccgtaaaaaggccgcgttgctggcgttttttccataggctccgcccccctgacgagcatcaca
aaaatcgacgctcaagtcagaggtggcgaaacccgacaggactataaagataccaggcgtttccccctggaagctcc
ctcgtgcgctctcctgttccgaccctgccgcttaccggatacctgtccgcctttctcccttcgggaagcgtggcgct
ttctcatagctcacgctgtaggtatctcagttcggtgtaggtcgttcgctccaagctgggctgtgtgcacgaacccc
ccgttcagcccgaccgctgcgccttatccggtaactatcgtcttgagtccaacccggtaagacacgacttatcgcca
ctggcagcagccactggtaacaggattagcagagcgaggtatgtaggcggtgctacagagttcttgaagtggtggcc
taactacggctacactagaagaacagtatttggtatctgcgctctactgaagccagttaccttcggaaaaagagttg
gtagctcttgatccggcaaacaaaccaccgctggtagcggttttttgtttgcaagcagcagattacgcgcagaaaa
aaaggatctcaagaagatcctttgatcttttctacggggtctgacgctcagtggaacgaaaactcacgttaagggat
tttggtcatgagattatcaaaaaggatcttcacctagatccttttaaattaaaaatgaagttttaaatcaatctaaa
gtatatatgagtaaacttggtctgacagttaccaatgcttaatcagtgaggcacctatctcagcgatctgtctattt
cgttcatccatagttgcctgactccccgtcgtgtagataactacgatacgggagggcttaccatctggccccagtgc
tgcaatgataccgcgagacccacgctcaccggctccagatttatcagcaataaaccagccagccggaagggccgagc
gcagaagtggtcctgcaactttatccgcctccatccagtctattaattgttgccgggaagctagagtaagtagttcg
ccagttaatagtttgcgcaacgttgttgccattgctacaggcatcgtggtgtcacgctcgtcgtttggtatggcttc
attcagctccggttcccaacgatcaaggcgagttacatgatccccatgttgtgcaaaaaagcggttagctccttcg
gtcctccgatcgttgtcagaagtaagttggccgcagtgttatcactcatggttatggcagcactgcataattctctt
actgtcatgccatccgtaagatgcttttctgtgactggtgagtactcaaccaagtcattctgagaatagtgtatgcg
gcgaccgagttgctcttgcccggcgtcaatacgggataataccgcgccacatagcagaactttaaaagtgctcatca
ttggaaaacgttcttcggggcgaaaactctcaaggatcttaccgctgttgagatccagttcgatgtaacccactcgt
gcacccaactgatcttcagcatcttttactttcaccagcgtttctgggtgagcaaaaacaggaaggcaaaatgccgc
aaaaaagggaataagggcgacacggaaatgttgaatactcatactcttcctttttcaatattattgaagcatttatc
agggttattgtctcatgagcggatacatatttgaatgtatttagaaaaataaacaaataggggttccgcgcacattt

Fig. 45C cccagaaaagtgccacctgacgtcgacggatcgggagatctcccgatcccctatggtgcactctcagtacaatctgc
tctgatgccgcatagttaagccagtatctgctccctgcttgtgtgttggaggtcgctgagtagtgcgcgagcaaaat
ttaagctacaacaaggcaaggcttgaccgacaattgcatgaagaatctgcttagggttaggcgttttgcgctgcttc
gcgatgtacgggccagatatacgcgttgacattgattattgactagttattaatagtaatcaattacggggtcatta
gttcatagcccatatatggagttccgcgttacataacttacggtaaatggcccgcctggctgaccgcccaacgaccc
ccgcccattgacgtcaataatgacgtatgttcccatagtaacgccaatagggactttccattgacgtcaatgggtgg
agtatttacggtaaactgcccacttggcagtacatcaagtgtatcatatgccaagtacgccccctattgacgtcaat
gacggtaaatggcccgcctggcattatgcccagtacatgaccttatgggactttcctacttggcagtacatctacgt
attagtcatcgctattaccatggtgatgcggttttggcagtacatcaatgggcgtggatagcggtttgactcacggg
gatttccaagtctccaccccattgacgtcaatgggagtttgttttggcaccaaaatcaacgggactttccaaaatgt
cgtaacaactccgccccattgacgcaaatgggcggtaggcgtgtacggtggaggtctatataagcagagctctctg
gctaactagagaacccactgcttactggcttatcgaaattaatacgactcactatagggagacccaagctggctagc
gtttaaacttaagcttggtaccgagctcggatccactagtccagtgtggtgg

SEQUENCE LISTING

```
<160> NUMBER OF SEQ ID NOS: 224

<210> SEQ ID NO 1
<211> LENGTH: 595
<212> TYPE: PRT
<213> ORGANISM: Homo sapiens

<400> SEQUENCE: 1

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140
```

-continued

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
            195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
            260                 265                 270

Tyr Ser Phe Arg Arg Leu Asp Asp Lys Thr Thr Asn Val Ser Leu Tyr
            275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg Ser His Ile Tyr
    355                 360                 365

Pro Trp Cys Lys Cys Gln Pro Cys Val Val Asn Glu Tyr Tyr Tyr
370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
            435                 440                 445

Thr Pro Pro Ile Pro Gly Gln Pro Glu Glu Ile Gln Leu Leu Arg Lys
    450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
            515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
            580                 585                 590

Ser Pro Tyr
        595

<210> SEQ ID NO 2
<211> LENGTH: 270
<212> TYPE: PRT
<213> ORGANISM: Homo sapiens

<400> SEQUENCE: 2

Ile Phe Ser Tyr Val Cys Phe Ala Leu Val Ser Asp Lys Leu Tyr Gln
1               5                   10                  15

Arg Lys Glu Pro Val Ile Ser Ser Val His Thr Lys Val Lys Gly Ile
            20                  25                  30

Ala Glu Val Lys Glu Glu Ile Val Glu Asn Gly Val Lys Lys Leu Val
        35                  40                  45

His Ser Val Phe Asp Thr Ala Asp Tyr Thr Phe Pro Leu Gln Gly Asn
    50                  55                  60

Ser Phe Phe Val Met Thr Asn Phe Leu Lys Thr Glu Gly Gln Glu Gln
65                  70                  75                  80

Arg Leu Cys Pro Glu Tyr Pro Thr Arg Arg Thr Leu Cys Ser Ser Asp
                85                  90                  95

Arg Gly Cys Lys Lys Gly Trp Met Asp Pro Gln Ser Lys Gly Ile Gln
            100                 105                 110

Thr Gly Arg Cys Val Val His Glu Gly Asn Gln Lys Thr Cys Glu Val
        115                 120                 125

Ser Ala Trp Cys Pro Ile Glu Ala Val Glu Glu Ala Pro Arg Pro Ala
    130                 135                 140

Leu Leu Asn Ser Ala Glu Asn Phe Thr Val Leu Ile Lys Asn Asn Ile
145                 150                 155                 160

Asp Phe Pro Gly His Asn Tyr Thr Thr Arg Asn Ile Leu Pro Gly Leu
                165                 170                 175

Asn Ile Thr Cys Thr Phe His Lys Thr Gln Asn Pro Gln Cys Pro Ile
            180                 185                 190

Phe Arg Leu Gly Asp Ile Phe Arg Glu Thr Gly Asp Asn Phe Ser Asp
        195                 200                 205

Val Ala Ile Gln Gly Gly Ile Met Gly Ile Glu Ile Tyr Trp Asp Cys
    210                 215                 220

Asn Leu Asp Arg Trp Phe His His Cys Arg Pro Lys Tyr Ser Phe Arg
225                 230                 235                 240

Arg Leu Asp Asp Lys Thr Thr Asn Val Ser Leu Tyr Pro Gly Tyr Asn
                245                 250                 255

Phe Arg Tyr Ala Lys Tyr Tyr Lys Glu Asn Asn Val Glu Lys
            260                 265                 270

<210> SEQ ID NO 3
<211> LENGTH: 296
<212> TYPE: PRT
<213> ORGANISM: Homo sapiens

<400> SEQUENCE: 3

Ile Phe Ser Tyr Val Cys Phe Ala Leu Val Ser Asp Lys Leu Tyr Gln
1               5                   10                  15

```
Arg Lys Glu Pro Val Ile Ser Ser Val His Thr Lys Val Lys Gly Ile
             20                  25                  30

Ala Glu Val Lys Glu Glu Ile Val Glu Asn Gly Val Lys Lys Leu Val
         35                  40                  45

His Ser Val Phe Asp Thr Ala Asp Tyr Thr Phe Pro Leu Gln Gly Asn
     50                  55                  60

Ser Phe Phe Val Met Thr Asn Phe Leu Lys Thr Gly Gln Glu Gln
 65                  70                  75                  80

Arg Leu Cys Pro Glu Tyr Pro Thr Arg Arg Thr Leu Cys Ser Ser Asp
                 85                  90                  95

Arg Gly Cys Lys Lys Gly Trp Met Asp Pro Gln Ser Lys Gly Ile Gln
            100                 105                 110

Thr Gly Arg Cys Val Val His Glu Gly Asn Gln Lys Thr Cys Glu Val
            115                 120                 125

Ser Ala Trp Cys Pro Ile Glu Ala Val Glu Glu Ala Pro Arg Pro Ala
        130                 135                 140

Leu Leu Asn Ser Ala Glu Asn Phe Thr Val Leu Ile Lys Asn Asn Ile
145                 150                 155                 160

Asp Phe Pro Gly His Asn Tyr Thr Thr Arg Asn Ile Leu Pro Gly Leu
                165                 170                 175

Asn Ile Thr Cys Thr Phe His Lys Thr Gln Asn Pro Gln Cys Pro Ile
            180                 185                 190

Phe Arg Leu Gly Asp Ile Phe Arg Glu Thr Gly Asp Asn Phe Ser Asp
            195                 200                 205

Val Ala Ile Gln Gly Gly Ile Met Gly Ile Glu Ile Tyr Trp Asp Cys
        210                 215                 220

Asn Leu Asp Arg Trp Phe His His Cys Arg Pro Lys Tyr Ser Phe Arg
225                 230                 235                 240

Arg Leu Asp Asp Lys Thr Thr Asn Val Ser Leu Tyr Pro Gly Tyr Asn
                245                 250                 255

Phe Arg Tyr Ala Lys Tyr Tyr Lys Glu Asn Asn Val Glu Lys Arg Thr
            260                 265                 270

Leu Ile Lys Val Phe Gly Ile Arg Phe Asp Ile Leu Val Phe Gly Thr
            275                 280                 285

Gly Gly Lys Phe Asp Ile Ile Gln
            290                 295

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Asn Glu Pro Met Gly
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

```
Ser Ile Ala Asp Ser Gly Asn His Thr Tyr Tyr Ala Asp Ser Val Lys
1               5                   10                  15

Gly

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Gln Arg Gly Leu Asn Arg Tyr Arg Ala Gln Phe Asp Tyr
1               5                   10

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Asn His Asp Met Gly
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ile Ser Gly Ser Gly Gly Ser Thr Tyr Tyr Ala Asp Ser Val Lys
1               5                   10                  15

Gly

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Pro Lys Pro Met Asp Thr Glu Phe Asp Tyr
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Gly Tyr Ala Met Ala
1               5

<210> SEQ ID NO 11
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Ile Leu Ser Asp Gly Ser Arg Thr Tyr Tyr Ala Asp Ser Val Lys
1               5                   10                  15
Gly

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Ile Lys Thr Phe Arg Asn His Ser Val Gln Phe Asp Tyr
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Met Tyr Asn Met Ser
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Ile Asn Ala Thr Gly Gly Arg Thr Tyr Tyr Ala Asp Ser Val Lys
1               5                   10                  15
Gly

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Phe Asn Gly Phe Ser His Arg Gln Tyr Asn Phe Asp Tyr
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 16

Pro Ala Ser Asn Met Ser
1               5

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ile Thr Ala Ser Gly Tyr Arg Thr Tyr Tyr Ala Asp Ser Val Lys
1               5                   10                  15
Gly

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Gln Gly Gln Ile Ser Asn Phe Pro Arg Phe Asp Tyr
1               5                   10

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Ser Tyr Ala Met Ala
1               5

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Ile Ser Thr Ser Gly Ser Ser Thr Tyr Tyr Ala Asp Ser Val Lys
1               5                   10                  15
Gly

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Val Arg Phe Ala Thr Ser Lys Ser Ile Asn Phe Asp Tyr
```

```
1               5                  10

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ala Tyr Ala Met Ser
1               5

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Ile Asn Gly Ser Gly Leu Ala Thr Tyr Tyr Ala Asp Ser Val Lys
1               5                   10                  15

Gly

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Cys Ser Ser Cys Thr Ser Leu Asn Ala Asn Phe Asp Tyr
1               5                   10

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Gly Tyr Asn Met Ser
1               5

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Ile Thr Ala Asn Gly Asn Ser Thr Tyr Tyr Ala Asp Ser Val Lys
1               5                   10                  15

Gly

<210> SEQ ID NO 27
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Ala Ser Tyr Ser Arg Pro Tyr Asn Phe Gln Phe Asp Tyr
1               5                   10

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Tyr Asp Met Ala Trp
1               5

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Ile Ala Ala Ala Gly Ser Arg Thr Tyr Tyr Ala Asp Ser Val Lys
1               5                   10                  15

Gly

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Gln Arg Ser Ile Ser Ile Arg Pro Met Phe Asp Tyr
1               5                   10

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Glu Tyr Gly Met Gly
1               5

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32
```

Ser Ile Thr Pro Ser Gly Asp Lys Thr Tyr Tyr Ala Asp Ser Val Lys
1               5                   10                  15

Gly

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Val Arg Ser Met Ser Tyr Ala His Phe Asp Phe Asp Tyr
1               5                   10

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Arg Tyr Pro Met Ala
1               5

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Ile Asp Gly Gly Gly Leu Gln Thr Tyr Tyr Ala Asp Ser Val Lys
1               5                   10                  15

Gly

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Ala Ser Ala Pro Lys Tyr Phe Arg Phe Asp Tyr
1               5                   10

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Ser Tyr Ala Met Ala
1               5

-continued

```
<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Ile Asp Gly Asn Gly Leu Ile Thr Tyr Tyr Ala Asp Ser Val Lys
1               5                   10                  15
Gly

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Leu Gln Arg Tyr Asp Arg Tyr Thr Leu Asn Phe Asp Tyr
1               5                   10

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Lys Tyr Pro Met Val
1               5

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Ile Gly Pro Gly Gly Ala Arg Thr Tyr Tyr Ala Asp Ser Val Lys
1               5                   10                  15
Gly

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Pro Trp Arg Val Tyr Ser Tyr Asp Arg Phe Asp Tyr
1               5                   10

<210> SEQ ID NO 43
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 43

Ser Ser Tyr Ala Met Ser
1               5

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Ile Thr Ser Asp Gly Leu Arg Thr Tyr Tyr Ala Asp Ser Val Lys
1               5                   10                  15

Gly

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Val His Thr Phe Ala Asn Arg Ser Leu Asn Phe Asp Tyr
1               5                   10

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Asn Val Glu Met Ser
1               5

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Ile Gly Ser Lys Gly Glu Asp Thr Tyr Tyr Ala Asp Ser Val Lys
1               5                   10                  15

Gly

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48
```

Gln Thr Val Asn Val Pro Glu Pro Ala Phe Ala Tyr
1               5                   10

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Pro Met Lys Asp Met Gly
1               5

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Ile Ser Gly Ser Gly Gly Ser Thr Tyr Tyr Ala Asp Ser Val Lys
1               5                   10                  15

Gly

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Pro Ser His Phe Asp Arg Pro Phe Asp Tyr
1               5                   10

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Asn His Asp Met Gly
1               5

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Ile Ser Gly Ser Gly Gly Ser Thr Tyr Tyr Ala Asn Ser Val Lys
1               5                   10                  15

Gly

<210> SEQ ID NO 54

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Pro Lys Pro Met Asp Thr Glu Phe Asp Tyr
1               5                   10

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Asn His Asp Met Gly
1               5

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Ile Ser Gly Ser Gly Gly Ser Thr Tyr Tyr Ala Asp Ser Val Lys
1               5                   10                  15

Gly

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Pro Lys Pro Met Asp Thr Glu Phe Asp Tyr
1               5                   10

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Asn His Asp Met Gly
1               5

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 59

Ala Ile Ser Gly Ser Gly Gly Ser Thr Tyr Tyr Ala Asp Ser Val Lys
1               5                   10                  15

Gly

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Pro Lys Pro Met Asp Thr Glu Phe Asp Tyr
1               5                   10

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Asn His Asp Met Gly
1               5

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Ile Ser Gly Ser Gly Gly Ser Thr Tyr Tyr Ala Asn Ser Val Lys
1               5                   10                  15

Gly

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Glu Pro Lys Pro Met Asp Thr Glu Phe Asp Tyr
1               5                   10

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Asn His Asp Met Gly
1               5
```

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ile Ser Gly Ser Gly Gly Ser Thr Tyr Tyr Ala Asn Ser Val Lys
1               5                   10                  15

Gly

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu Pro Lys Pro Met Asp Thr Glu Phe Asp Tyr
1               5                   10

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Asn His Asp Met Gly
1               5

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Ile Ser Gly Ser Gly Gly Ser Thr Tyr Tyr Ala Asp Ser Val Lys
1               5                   10                  15

Gly

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Glu Pro Lys Pro Met Asp Thr Glu Phe Asp Tyr
1               5                   10

<210> SEQ ID NO 70
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 70

Arg Asn His Asp Met Gly
1               5

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Ile Ser Gly Ser Gly Gly Ser Thr Tyr Tyr Ala Asp Ser Val Lys
1               5                   10                  15

Gly

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Pro Lys Pro Met Asp Thr Glu Phe Asp Tyr
1               5                   10

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Asn His Asp Met Gly
1               5

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Ile Ser Gly Ser Gly Gly Ser Thr Tyr Tyr Ala Asp Ser Val Lys
1               5                   10                  15

Gly

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75
```

Glu Pro Lys Pro Met Asp Thr Glu Phe Asp Tyr
1               5                   10

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Asn His Asp Met Gly
1               5

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Ile Ser Gly Ser Gly Gly Ser Thr Tyr Tyr Ala Asp Ser Val Lys
1               5                   10                  15
Gly

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Glu Pro Lys Pro Met Asp Thr Glu Phe Asp Tyr
1               5                   10

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Asn His Asp Met Gly
1               5

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Ile Ser Gly Ser Gly Gly Ser Thr Tyr Tyr Ala Asp Ser Val Lys
1               5                   10                  15
Gly

```
<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Glu Pro Lys Pro Met Asp Thr Glu Phe Asp Tyr
1               5                   10

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Asn His Asp Met Gly
1               5

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Ile Ser Gly Ser Gly Gly Ser Thr Tyr Tyr Ala Asp Ser Val Lys
1               5                   10                  15

Gly

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Pro Lys Pro Met Asp Thr Glu Phe Asp Tyr
1               5                   10

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Asn His Asp Met Gly
1               5

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 86

Ala Ile Ser Gly Ser Gly Gly Ser Thr Tyr Tyr Ala Asp Ser Val Lys
1               5                   10                  15

Gly

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Glu Pro Lys Pro Met Asp Thr Glu Phe Asp Tyr
1               5                   10

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Asn His Asp Met Gly
1               5

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Ile Ser Gly Ser Gly Gly Ser Thr Tyr Tyr Ala Asp Ser Val Lys
1               5                   10                  15

Gly

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Glu Pro Lys Pro Met Asp Thr Glu Phe Asp Tyr
1               5                   10

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Asn His Asp Met Gly
1               5
```

```
<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala Ile Ser Gly Ser Gly Gly Ser Thr Tyr Tyr Ala Asp Ser Val Lys
1               5                   10                  15

Gly

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Glu Pro Lys Pro Met Asp Thr Glu Phe Asp Tyr
1               5                   10

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Asn His Asp Met Gly
1               5

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ala Ile Ser Gly Ser Gly Gly Ser Thr Tyr Tyr Ala Asp Ser Val Lys
1               5                   10                  15

Gly

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Glu Pro Lys Pro Met Asp Thr Glu Phe Asp Tyr
1               5                   10

<210> SEQ ID NO 97
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 97

Arg Asn His Asp Met Gly
1               5

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Ile Ser Gly Ser Gly Gly Ser Thr Tyr Tyr Ala Asp Ser Val Lys
1               5                   10                  15
Gly

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Glu Pro Lys Pro Met Asp Thr Glu Phe Asp Tyr
1               5                   10

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Asn His Asp Met Gly
1               5

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Ile Ser Gly Ser Gly Gly Ser Thr Tyr Tyr Ala Asp Ser Val Lys
1               5                   10                  15
Gly

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 102

Glu Pro Lys Pro Met Asp Thr Glu Phe Asp Tyr
1               5                   10

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Asn His Asp Met Gly
1               5

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ala Ile Ser Gly Ser Gly Gly Ser Thr Tyr Tyr Ala Asp Ser Val Lys
1               5                   10                  15

Gly

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Glu Pro Lys Pro Met Asp Thr Glu Phe Asp Tyr
1               5                   10

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Asn His Asp Met Gly
1               5

<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Ile Ser Gly Ser Gly Gly Ser Thr Tyr Tyr Ala Asp Ser Val Lys
1               5                   10                  15

Gly
```

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Glu Pro Lys Pro Met Asp Thr Glu Phe Asp Tyr
1               5                   10

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Asn His Asp Met Gly
1               5

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Ile Ser Gly Ser Gly Gly Thr Tyr Tyr Ala Asp Ser Val Lys
1               5                   10                  15

Gly

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Glu Pro Ser His Phe Asp Arg Pro Phe Asp Tyr
1               5                   10

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Asn His Asp Met Gly
1               5

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 113

Ala Ile Ser Gly Ser Gly Gly Ser Thr Tyr Tyr Ala Asn Ser Val Lys
1               5                   10                  15

Gly

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Glu Pro Ser His Phe Asp Arg Pro Phe Asp Tyr
1               5                   10

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Pro Met Lys Asp Met Gly
1               5

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ala Ile Ser Gly Ser Gly Gly Thr Tyr Tyr Ala Asp Ser Val Lys
1               5                   10                  15

Gly

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Glu Pro Lys Pro Met Asp Thr Glu Phe Asp Tyr
1               5                   10

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Pro Met Lys Asp Met Gly

```
<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Ile Ser Gly Ser Gly Gly Gly Thr Tyr Tyr Ala Asp Ser Val Lys
1               5                   10                  15
Gly

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Glu Pro Lys Pro Met Asp Thr Glu Phe Asp Tyr
1               5                   10

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Pro Met Lys Asp Met Gly
1               5

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Ile Ser Gly Ser Gly Gly Gly Thr Tyr Tyr Ala Asp Ser Val Lys
1               5                   10                  15
Gly

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Glu Pro Lys Pro Met Asp Thr Glu Phe Asp Tyr
1               5                   10

<210> SEQ ID NO 124
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Pro Met Lys Asp Met Gly
1               5

<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Ile Ser Gly Ser Gly Gly Thr Tyr Tyr Ala Asp Ser Val Lys
1               5                   10                  15
Gly

<210> SEQ ID NO 126
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Glu Pro Lys Pro Met Asp Thr Glu Phe Asp Tyr
1               5                   10

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Asp Asn Val Glu Met Ser
1               5

<210> SEQ ID NO 128
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser Ile Gly Thr Lys Gly Glu Tyr Thr Tyr Tyr Ala Asp Ser Val Lys
1               5                   10                  15
Gly

<210> SEQ ID NO 129
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 129

Gln Thr Val Asn Val Pro Glu Pro Ala Phe Ala Tyr
1               5                   10

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp Asn Val Glu Met Ser
1               5

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Ile Gly Ser Lys Gly Glu Tyr Thr Tyr Tyr Ala Asp Ser Val Lys
1               5                   10                  15

Gly

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Thr Val Asn Val Pro Glu Pro Ala Phe Ala Tyr
1               5                   10

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Pro Met Lys Asp Met Gly
1               5

<210> SEQ ID NO 134
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Ile Ser Gly Ser Gly Gly Thr Tyr Tyr Ala Asp Ser Val Lys
1               5                   10                  15

Gly
```

```
<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Glu Pro Ser His Phe Asp Arg Pro Phe Asp Tyr
1               5                   10

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Pro Met Lys Asp Met Gly
1               5

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ala Ile Ser Gly Ser Gly Gly Gly Thr Tyr Tyr Ala Asn Ser Val Lys
1               5                   10                  15

Gly

<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Glu Pro Ser His Phe Asp Arg Pro Phe Asp Tyr
1               5                   10

<210> SEQ ID NO 139
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe
                20                  25

<210> SEQ ID NO 140
<211> LENGTH: 29
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Arg Ile
            20                  25

<210> SEQ ID NO 141
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu
            20                  25

<210> SEQ ID NO 142
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Phe
            20                  25

<210> SEQ ID NO 143
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Glu Val Gln Leu Leu Glu Ser Gly Gly Gly Leu Val Gln Pro Gly Gly
1               5                   10                  15

Ser Leu Arg Leu Thr Cys Ala Ala Ser Gly Phe Ser Phe
            20                  25

<210> SEQ ID NO 144
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Glu Val Gln Met Leu Glu Ser Gly Gly Gly Leu Val Gln Pro Gly Glu
1               5                   10                  15
```

Ser Leu Arg Leu Ser Cys Ala Ala Ser Gly Phe Thr Phe
            20                  25

<210> SEQ ID NO 145
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Trp Val Arg Gln Ala Pro Gly Lys Gly Leu Glu Trp Val Ser
1               5                   10

<210> SEQ ID NO 146
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Trp Val Arg Gln Ala Pro Gly Lys Gly Leu Glu Trp Ala Ser
1               5                   10

<210> SEQ ID NO 147
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Trp Ala Arg Gln Ala Pro Gly Lys Gly Leu Glu Trp Val Ser
1               5                   10

<210> SEQ ID NO 148
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala
            20                  25                  30

<210> SEQ ID NO 149
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Arg Phe Thr Ile Ser Arg Asp Asn Ser Arg Asn Thr Leu Tyr Leu Gln
1               5                   10                  15

Met Asn Ser Leu Arg Ala Glu Asp Thr Ala Val Tyr Tyr Cys Ala
            20                  25                  30

```
<210> SEQ ID NO 150
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Arg Phe Thr Ile Ser Arg Asp Asn Ser Lys Asn Thr Leu Tyr Leu Gln
1               5                   10                  15

Met Asn Ser Met Arg Ala Glu Asp Thr Ala Val Tyr Tyr Cys Ala
            20                  25                  30

<210> SEQ ID NO 151
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Arg Phe Thr Ile Ser Arg Asp Asn Ser Lys Asn Thr Leu Tyr Leu Gln
1               5                   10                  15

Met Asn Ser Pro Arg Ala Glu Asp Thr Ala Val Tyr Tyr Cys Ala
            20                  25                  30

<210> SEQ ID NO 152
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Arg Phe Thr Ile Ser Arg Asp Asp Ser Lys Asn Thr Leu Tyr Leu Gln
1               5                   10                  15

Met Asn Ser Leu Arg Ala Glu Asp Thr Ala Val Tyr Tyr Cys Ala
            20                  25                  30

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Trp Gly Gln Gly Thr Leu Val Thr Val Ser Ser
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Trp Gly Gln Gly Thr Leu Val Thr Val Leu Ser
1               5                   10
```

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Arg Ser Pro Gly Thr Leu Val Thr Val Ser Ser
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Pro Ser Pro Gly Thr Gln Val Thr Val Ser Ser
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Pro Ser Pro Gly Thr Leu Val Thr Val Ser Ser
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Arg Ser Gln Gly Thr Leu Val Thr Val Ser Ser
1               5                   10

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Trp Ser Gln Gly Thr Leu Val Thr Val Ser Ser
1               5                   10

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 160

Arg Gly Gln Gly Thr Leu Val Thr Val Ser Ser
1               5                   10

<210> SEQ ID NO 161
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Arg Phe Gln Gly Thr Leu Val Thr Val Ser Ser
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Trp Ser Pro Gly Thr Leu Val Thr Val Ser Ser
1               5                   10

<210> SEQ ID NO 163
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Ser Pro Gly Thr Leu Val Thr Val Ser Ser
1               5                   10

<210> SEQ ID NO 164
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Trp Gly Pro Gly Thr Leu Val Thr Val Ser Ser
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Arg Gly Pro Gly Thr Leu Val Thr Val Ser Ser
1               5                   10

<210> SEQ ID NO 166
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 166

Cys Gly Pro Gly Thr Leu Val Thr Val Ser Ser
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Ser Cys Gly Thr Leu Val Thr Val Ser Ser
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Arg Ser Pro Gly Thr Leu Val Thr Val Leu Glu
1               5                   10

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Pro Ser Pro Gly Thr Leu Val Thr Val Leu Glu
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Arg Ser Gln Gly Thr Leu Val Thr Val Ser Ser
1               5                   10

<210> SEQ ID NO 171
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Arg Ile Arg Asn His
        20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Trp Gly Gln Gly
            100                 105                 110

Thr Leu Val Thr Val Ser Ser
            115
```

```
<210> SEQ ID NO 172
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asn Val
            20                  25                  30

Glu Met Ser Trp Val Arg Gln Ala Pro Gly Lys Gly Leu Glu Trp Val
        35                  40                  45

Ser Ser Ile Gly Ser Lys Gly Glu Asp Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gln Thr Val Asn Val Pro Glu Pro Ala Phe Ala Tyr Trp Gly Gln
            100                 105                 110

Gly Thr Leu Val Thr Val Ser Ser
        115                 120
```

```
<210> SEQ ID NO 173
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Met Lys
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Ser His Phe Asp Arg Pro Phe Asp Tyr Trp Gly Gln Gly
            100                 105                 110

Thr Leu Val Thr Val Ser Ser
            115

<210> SEQ ID NO 174
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Arg Ser Pro Gly
            100                 105                 110

Thr Leu Val Thr Val Ser Ser
            115

<210> SEQ ID NO 175
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Arg Ser Pro Gly
            100                 105                 110

Thr Leu Val Thr Val Ser Ser
        115

<210> SEQ ID NO 176
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Arg Ser Gln Gly
            100                 105                 110

Thr Leu Val Thr Val Ser Ser
        115

<210> SEQ ID NO 177
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Pro Ser Pro Gly
            100                 105                 110

Thr Gln Val Thr Val Ser Ser
        115

<210> SEQ ID NO 178
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Pro Ser Pro Gly
            100                 105                 110

Thr Leu Val Thr Val Ser Ser
        115

<210> SEQ ID NO 179
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Arg Ser Gln Gly
            100                 105                 110

Thr Leu Val Thr Val Ser Ser
        115

<210> SEQ ID NO 180
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Glu Val Gln Leu Leu Glu Ser Gly Gly Gly Leu Val Gln Pro Gly Gly
1               5                   10                  15

```
Ser Leu Arg Leu Thr Cys Ala Ala Ser Gly Phe Ser Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Arg Ser Pro Gly
            100                 105                 110

Thr Leu Val Thr Val Ser Ser
            115
```

<210> SEQ ID NO 181
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Arg Ser Pro Gly
            100                 105                 110

Thr Leu Val Thr Val Ser Ser
            115
```

<210> SEQ ID NO 182
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Glu Pro Lys Pro Met Asp Thr Glu Phe Asp Tyr Phe Ser Gln Gly
            100                 105                 110

Thr Leu Val Thr Val Ser Ser
            115
```

<210> SEQ ID NO 183
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Asn His
             20                  25                  30

Asp Met Gly Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Glu Pro Lys Pro Met Asp Thr Glu Phe Asp Tyr Arg Phe Gln Gly
            100                 105                 110

Thr Leu Val Thr Val Ser Ser
            115
```

<210> SEQ ID NO 184
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Asn His
             20                  25                  30

Asp Met Gly Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Glu Pro Lys Pro Met Asp Thr Glu Phe Asp Tyr Trp Ser Pro Gly
            100                 105                 110
```

Thr Leu Val Thr Val Ser Ser
        115

<210> SEQ ID NO 185
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Arg Phe Pro Gly
            100                 105                 110

Thr Leu Val Thr Val Ser Ser
        115

<210> SEQ ID NO 186
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Arg Gly Pro Gly
            100                 105                 110

Thr Leu Val Thr Val Ser Ser
        115

<210> SEQ ID NO 187
<211> LENGTH: 119
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 187

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Cys Gly Pro Gly
            100                 105                 110

Thr Leu Val Thr Val Ser Ser
        115

<210> SEQ ID NO 188
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Phe Pro Met Lys
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Arg Ser Gln Gly
            100                 105                 110

Thr Leu Val Thr Val Ser Ser
        115

<210> SEQ ID NO 189
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Phe Pro Met Lys

```
            20                  25                  30
Asp Met Gly Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Arg Ser Cys Gly
            100                 105                 110

Thr Leu Val Thr Val Ser Ser
            115

<210> SEQ ID NO 190
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Phe Pro Met Lys
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Arg Ser Pro Gly
            100                 105                 110

Thr Leu Val Thr Val Ser Ser
            115

<210> SEQ ID NO 191
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Phe Pro Met Lys
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
```

```
65                  70                  75                  80
Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Pro Ser Pro Gly
            100                 105                 110

Thr Leu Val Thr Val Ser Ser
        115

<210> SEQ ID NO 192
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Ser His Phe Asp Arg Pro Phe Asp Tyr Arg Ser Gln Gly
            100                 105                 110

Thr Leu Val Thr Val Ser Ser
        115

<210> SEQ ID NO 193
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Ser His Phe Asp Arg Pro Phe Asp Tyr Arg Ser Gln Gly
            100                 105                 110

Thr Leu Val Thr Val Ser Ser
```

115

<210> SEQ ID NO 194
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Glu Val Gln Met Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asn Val
            20                  25                  30

Glu Met Ser Trp Val Arg Gln Ala Pro Gly Lys Gly Leu Glu Trp Val
        35                  40                  45

Ser Ser Ile Gly Thr Lys Gly Glu Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Met Arg Ala Glu Asp Thr Ala Val Tyr Tyr Cys
                85                  90                  95

Ala Gln Thr Val Asn Val Pro Glu Pro Ala Phe Ala Tyr Trp Gly Gln
            100                 105                 110

Gly Thr Leu Val Thr Val Leu Ser
        115                 120

<210> SEQ ID NO 195
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Val Gln Met Leu Glu Ser Gly Gly Gly Leu Val Gln Pro Gly Glu
1               5                   10                  15

Ser Leu Arg Leu Ser Cys Ala Ala Ser Gly Phe Thr Phe Asp Asn Val
            20                  25                  30

Glu Met Ser Trp Val Arg Gln Ala Pro Gly Lys Gly Leu Glu Trp Val
        35                  40                  45

Ser Ser Ile Gly Ser Lys Gly Glu Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Pro Arg Ala Glu Asp Thr Ala Val Tyr Tyr Cys
                85                  90                  95

Ala Gln Thr Val Asn Val Pro Glu Pro Ala Phe Ala Tyr Trp Gly Gln
            100                 105                 110

Gly Thr Leu Val Thr Val Ser Ser
        115                 120

<210> SEQ ID NO 196
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 196

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Tyr Thr Phe Pro Met Lys
            20                  25                  30
Asp Met Gly Trp Val Arg Gln Ala Pro Gly Lys Gly Leu Glu Trp Val
        35                  40                  45
Ser Ala Ile Ser Gly Ser Gly Gly Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Glu Pro Ser His Phe Asp Arg Pro Phe Asp Tyr Arg Ser Gln Gly
            100                 105                 110
Thr Leu Val Thr Val Ser Ser
        115
```

<210> SEQ ID NO 197
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Tyr Thr Phe Pro Met Lys
            20                  25                  30
Asp Met Gly Trp Val Arg Gln Ala Pro Gly Lys Gly Leu Glu Trp Val
        35                  40                  45
Ser Ala Ile Ser Gly Ser Gly Gly Thr Tyr Tyr Ala Asn Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Glu Pro Ser His Phe Asp Arg Pro Phe Asp Tyr Arg Ser Gln Gly
            100                 105                 110
Thr Leu Val Thr Val Ser Ser
        115
```

<210> SEQ ID NO 198
<211> LENGTH: 6520
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198

```
aattcgccgc caccatggag accgacaccc tgctgctgtg ggtgctgctg ctgtgggtgc      60
ccggatccac cggcgaggtg cagctgttgg agtctggggg aggcttggta cagcctgggg     120
ggtccctgcg tctctcctgt gcagcctccg gattcacctt tcgtaatcat gatatgggt      180
```

```
gggtccgcca ggctccaggg aagggtctag agtgggtctc agctattagt ggtagtggtg      240
gtagcacata ctacgcaaac tccgtgaagg gccggttcac catctcccgc gacaattcca      300
agaacacgct gtatctgcaa atgaacagcc tgcgtgccga ggacaccgcg gtatattact      360
gtgcggaacc gaagcctatg gatacggagt ttgactacag gagtccggga accctggtca      420
ccgtctcgag cgctagcacc cacacctgcc ccccctgccc tgccccgag ctgctgggcg       480 gacctagcgt gttcctgttc ccccccaagc ctaaggacac cctgatgatc agcaggaccc      540
ccgaagtgac ctgcgtggtg gtggatgtga gccacgagga ccctgaagtg aagttcaact      600
ggtacgtgga cggcgtggaa gtgcacaacg ccaagaccaa gccagagag gagcagtaca      660 acagcaccta ccgcgtggtg tctgtgctga ccgtgctgca ccaggattgg ctgaacggca      720
aggagtacaa gtgcaaagtg agcaacaagg ccctgcctgc ccctatcgag aaaaccatca      780
gcaaggccaa gggccagcct agagagcccc aggtctacac cctgcctccc tccagagatg      840
agctgaccaa gaaccaggtg tccctgacct gtctggtgaa gggcttctac cccagcgaca      900
tcgccgtgga gtgggagagc aacggccagc ccgagaacaa ctacaagacc ccccccctg       960 tgctggacag cgatggcagc ttcttcctgt actccaagct gaccgtggac aagagcagat     1020
ggcagcaggg caacgtgttc agctgcagcg tgatgcacga ggccctgcac aatcactaca     1080
cccagaagag tctgagcctg tcccctggca agtgatagcg gccgctcgag tctagagggc     1140
ccgtttaaac ccgctgatca gcctcgactg tgccttctag ttgccagcca tctgttgttt     1200
gcccctcccc cgtgccttcc ttgaccctgg aaggtgccac tcccactgtc ctttcctaat     1260
aaaatgagga aattgcatcg cattgtctga gtaggtgtca ttctattctg gggggtgggg     1320
tggggcagga cagcaagggg gaggattggg aagacaatag caggcatgct ggggatgcgg     1380
tgggctctat ggcttctgag gcggaaagaa ccagctgggg ctctagggg tatccccacg     1440 cgccctgtag cggcgcatta agcgcggcgg gtgtggtggt tacgcgcagc gtgaccgcta     1500
cacttgccag cgccctagcg cccgctcctt tcgctttctt cccttccttt ctcgccacgt     1560
tcgccggctt tccccgtcaa gctctaaatc ggggctccc tttagggttc cgatttagtg      1620
ctttacggca cctcgacccc aaaaaacttg attagggtga tggttcacgt agtgggccat     1680
cgccctgata cggttttt cgcccttga cgttggagtc cacgttcttt aatagtggac       1740
tcttgttcca aactggaaca acactcaacc ctatctcggt ctattctttt gatttataag     1800
ggattttgcc gatttcggcc tattggttaa aaaatgagct gatttaacaa aaatttaacg     1860
cgaattaatt ctgtggaatg tgtgtcagtt agggtgtgga aagtccccag gctcccagc      1920 aggcagaagt atgcaaagca tgcatctcaa ttagtcagca accaggtgtg gaaagtcccc     1980
aggctcccca gcaggcagaa gtatgcaaag catgcatctc aattagtcag caaccatagt     2040
cccgccccta actccgccca tcccgcccct aactccgccc agttccgccc attctccgcc     2100
ccatggctga ctaattttttt ttatttatgc agaggccgag gccgcctctg cctctgagct     2160
attccagaag tagtgaggag gcttttttgg aggcctaggc ttttgcaaaa agctcccggg     2220
agcttgtata tccattttcg gatctgatca agagacagga tgaggatcgt ttcgcatgat     2280
tgaacaagat ggattgcacg caggttctcc ggccgcttgg gtggagaggc tattcggcta     2340
tgactgggca acacagacaa tcggctgctc tgatgccgcc gtgttccggc tgtcagcgca     2400
ggggcgcccg gttcttttg tcaagaccga cctgtccggt gccctgaatg aactgcagga     2460
cgaggcagcg cggctatcgt ggctggccac gacgggcgtt ccttgcgcag ctgtgctcga     2520
```

```
cgttgtcact gaagcgggaa gggactggct gctattgggc gaagtgccgg ggcaggatct    2580
cctgtcatct caccttgctc ctgccgagaa agtatccatc atggctgatg caatgcggcg    2640
gctgcatacg cttgatccgg ctacctgccc attcgaccac caagcgaaac atcgcatcga    2700
gcgagcacgt actcggatgg aagccggtct tgtcgatcag gatgatctgg acgaagagca    2760 tcagggctc gcgccagccg aactgttcgc caggctcaag gcgcgcatgc ccgacggcga     2820
ggatctcgtc gtgacccatg gcgatgcctg cttgccgaat atcatggtgg aaaatggccg    2880
cttttctgga ttcatcgact gtggccggct gggtgtggcg gaccgctatc aggacatagc    2940
gttggctacc cgtgatattg ctgaagagct tggcggcgaa tgggctgacc gcttcctcgt    3000
gctttacggt atcgccgctc ccgattcgca gcgcatcgcc ttctatcgcc ttcttgacga    3060
gttcttctga gcgggactct ggggttcgaa atgaccgacc aagcgacgcc caacctgcca    3120
tcacgagatt tcgattccac cgccgccttc tatgaaaggt tgggcttcgg aatcgttttc    3180
cgggacgccg gctggatgat cctccagcgc ggggatctca tgctggagtt cttcgcccac    3240
cccaacttgt ttattgcagc ttataatggt tacaaataaa gcaatagcat cacaaatttc    3300
acaaataaag cattttttc actgcattct agttgtggtt tgtccaaact catcaatgta     3360
tcttatcatg tctgtatacc gtcgacctct agctagagct tggcgtaatc atggtcatag    3420
ctgtttcctg tgtgaaattg ttatccgctc acaattccac acaacatacg agccggaagc    3480
ataaagtgta aagcctgggg tgcctaatga gtgagctaac tcacattaat tgcgttgcgc    3540
tcactgcccg ctttccagtc gggaaacctg tcgtgccagc tgcattaatg aatcggccaa    3600
cgcgcgggga gaggcggttt gcgtattggg cgctcttccg cttcctcgct cactgactcg    3660
ctgcgctcgg tcgttcggct gcggcgagcg gtatcagctc actcaaaggc ggtaatacgg    3720
ttatccacag aatcagggga taacgcagga agaacatgtg agcaaaaggc cagcaaaag     3780 gccaggaacc gtaaaaaggc cgcgttgctg gcgtttttcc ataggctccg ccccccctgac   3840 gagcatcaca aaaatcgacg ctcaagtcag aggtggcgaa acccgacagg actataaaga    3900
taccaggcgt ttccccctgg aagctccctc gtgcgctctc ctgttccgac cctgccgctt    3960
accggatacc tgtccgcctt tctcccttcg ggaagcgtgg cgctttctca tagctcacgc    4020
tgtaggtatc tcagttcggt gtaggtcgtt cgctccaagc tgggctgtgt gcacgaaccc    4080
cccgttcagc ccgaccgctg cgccttatcc ggtaactatc gtcttgagtc aacccggta    4140 agacacgact tatcgccact ggcagcagcc actggtaaca ggattagcag agcgaggtat    4200
gtaggcggtg ctacagagtt cttgaagtgg tggcctaact acggctacac tagaagaaca    4260
gtatttggta tctgcgctct gctgaagcca gttaccttcg aaaaagagt tggtagctct     4320 tgatccggca aacaaaccac cgctggtagc ggttttttg tttgcaagca gcagattacg     4380
cgcagaaaaa aaggatctca agaagatcct ttgatctttt ctacggggtc tgacgctcag    4440
tggaacgaaa actcacgtta agggattttg gtcatgagat tatcaaaaag gatcttcacc    4500
tagatccttt taaattaaaa atgaagtttt aaatcaatct aaagtatata tgagtaaact    4560
tggtctgaca gttaccaatg cttaatcagt gaggcaccta tctcagcgat ctgtctattt    4620
cgttcatcca tagttgcctg actccccgtc gtgtagataa ctacgatacg ggagggctta    4680
ccatctggcc ccagtgctgc aatgataccg cgagacccac gctcaccggc tccagattta    4740
tcagcaataa accagccagc cggaagggcc gagcgcagaa gtggtcctgc aactttatcc    4800
gcctccatcc agtctattaa ttgttgccgg gaagctagag taagtagttc gccagttaat    4860
agtttgcgca acgttgttgc cattgctaca ggcatcgtgg tgtcacgctc gtcgtttggt    4920
```

-continued

```
atggcttcat tcagctccgg ttcccaacga tcaaggcgag ttacatgatc ccccatgttg    4980
tgcaaaaaag cggttagctc cttcggtcct ccgatcgttg tcagaagtaa gttggccgca    5040
gtgttatcac tcatggttat ggcagcactg cataattctc ttactgtcat gccatccgta    5100
agatgctttt ctgtgactgg tgagtactca accaagtcat tctgagaata gtgtatgcgg    5160
cgaccgagtt gctcttgccc ggcgtcaata cgggataata ccgcgccaca tagcagaact    5220
ttaaaagtgc tcatcattgg aaaacgttct tcggggcgaa aactctcaag gatcttaccg    5280
ctgttgagat ccagttcgat gtaacccact cgtgcaccca actgatcttc agcatctttt    5340
actttcacca gcgtttctgg gtgagcaaaa acaggaaggc aaaatgccgc aaaaaaggga    5400
ataagggcga cacggaaatg ttgaatactc atactcttcc tttttcaata ttattgaagc    5460
atttatcagg gttattgtct catgagcgga tacatatttg aatgtattta gaaaaataaa    5520
caaatagggg ttccgcgcac atttccccga aaagtgccac ctgacgtcga cggatcggga    5580
gatctcccga tcccctatgg tgcactctca gtacaatctg ctctgatgcc gcatagttaa    5640
gccagtatct gctccctgct tgtgtgttgg aggtcgctga gtagtgcgcg agcaaaattt    5700
aagctacaac aaggcaaggc ttgaccgaca attgcatgaa gaatctgctt agggttaggc    5760
gttttgcgct gcttcgcgat gtacgggcca gatatacgcg ttgacattga ttattgacta    5820
gttattaata gtaatcaatt acggggtcat tagttcatag cccatatatg gagttccgcg    5880
ttacataact tacggtaaat ggcccgcctg gctgaccgcc caacgacccc cgcccattga    5940
cgtcaataat gacgtatgtt cccatagtaa cgccaatagg gactttccat tgacgtcaat    6000
gggtggagta tttacggtaa actgcccact tggcagtaca tcaagtgtat catatgccaa    6060
gtacgccccc tattgacgtc aatgacggta aatggcccgc ctggcattat gcccagtaca    6120
tgaccttatg ggactttcct acttggcagt acatctacgt attagtcatc gctattacca    6180
tggtgatgcg gttttggcag tacatcaatg ggcgtggata gcggtttgac tcacggggat    6240
ttccaagtct ccaccccatt gacgtcaatg ggagtttgtt ttggcaccaa aatcaacggg    6300
actttccaaa atgtcgtaac aactccgccc cattgacgca aatgggcggt aggcgtgtac    6360
ggtgggaggt ctatataagc agagctctct ggctaactag agaacccact gcttactggc    6420
ttatcgaaat taatacgact cactataggg agacccaagc tggctagcgt ttaaacttaa    6480
gcttggtacc gagctcggat ccactagtcc agtgtggtgg                          6520
```

```
<210> SEQ ID NO 199
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pro or Arg
<220> FEATURE:
<221> NAME/KEY: MOD_RES
<222> LOCATION: (2)..(2)
<223> OTHER INFORMATION: Asn or Met
<220> FEATURE:
<221> NAME/KEY: MOD_RES
<222> LOCATION: (3)..(3)
<223> OTHER INFORMATION: His or Lys

<400> SEQUENCE: 199

Xaa Xaa Xaa Asp Met Gly
```

<210> SEQ ID NO 200
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ser or Gly
<220> FEATURE:
<221> NAME/KEY: MOD_RES
<222> LOCATION: (13)..(13)
<223> OTHER INFORMATION: Asp or Asn

<400> SEQUENCE: 200

Ala Ile Ser Gly Ser Gly Gly Xaa Thr Tyr Tyr Ala Xaa Ser Val Lys
1               5                   10                  15

Gly

<210> SEQ ID NO 201
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys or Ser
<220> FEATURE:
<221> NAME/KEY: MOD_RES
<222> LOCATION: (4)..(4)
<223> OTHER INFORMATION: Pro or His
<220> FEATURE:
<221> NAME/KEY: MOD_RES
<222> LOCATION: (5)..(5)
<223> OTHER INFORMATION: Met or Phe
<220> FEATURE:
<221> NAME/KEY: MOD_RES
<222> LOCATION: (7)..(7)
<223> OTHER INFORMATION: Thr or Arg
<220> FEATURE:
<221> NAME/KEY: MOD_RES
<222> LOCATION: (8)..(8)
<223> OTHER INFORMATION: Glu or Pro

<400> SEQUENCE: 201

Glu Pro Xaa Xaa Xaa Asp Xaa Xaa Phe Asp Tyr
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp, Arg, Pro, Gly or Cys
<220> FEATURE:
<221> NAME/KEY: MOD_RES
<222> LOCATION: (2)..(2)
<223> OTHER INFORMATION: Gly, Ser or Phe
<220> FEATURE:
<221> NAME/KEY: MOD_RES
<222> LOCATION: (3)..(3)

```
<223> OTHER INFORMATION: Gln, Pro or Cys
<220> FEATURE:
<221> NAME/KEY: MOD_RES
<222> LOCATION: (6)..(6)
<223> OTHER INFORMATION: Leu or Gln
<220> FEATURE:
<221> NAME/KEY: MOD_RES
<222> LOCATION: (10)..(10)
<223> OTHER INFORMATION: Ser or Leu
<220> FEATURE:
<221> NAME/KEY: MOD_RES
<222> LOCATION: (11)..(11)
<223> OTHER INFORMATION: Ser or Glu

<400> SEQUENCE: 202

Xaa Xaa Xaa Gly Thr Xaa Val Thr Val Xaa Xaa
1               5                   10

<210> SEQ ID NO 203
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ser or Pro
<220> FEATURE:
<221> NAME/KEY: MOD_RES
<222> LOCATION: (27)..(27)
<223> OTHER INFORMATION: Tyr, Phe or Val
<220> FEATURE:
<221> NAME/KEY: MOD_RES
<222> LOCATION: (28)..(28)
<223> OTHER INFORMATION: Arg, Thr or Asn
<220> FEATURE:
<221> NAME/KEY: MOD_RES
<222> LOCATION: (29)..(29)
<223> OTHER INFORMATION: Ile, Phe or Val

<400> SEQUENCE: 203

Glu Val Gln Leu Leu Glu Xaa Gly Gly Gly Leu Val Gln Pro Gly Gly
1               5                   10                  15

Ser Leu Arg Leu Ser Cys Ala Ala Ser Gly Xaa Xaa Xaa
            20                  25

<210> SEQ ID NO 204
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or Ala
<220> FEATURE:
<221> NAME/KEY: MOD_RES
<222> LOCATION: (13)..(13)
<223> OTHER INFORMATION: Val or Ala

<400> SEQUENCE: 204

Trp Xaa Arg Gln Ala Pro Gly Lys Gly Leu Glu Trp Xaa Ser
1               5                   10

<210> SEQ ID NO 205
<211> LENGTH: 31
<212> TYPE: PRT
<213> ORGANISM: Artificial Sequence
```

-continued

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Arg or Lys
<220> FEATURE:
<221> NAME/KEY: MOD_RES
<222> LOCATION: (20)..(20)
<223> OTHER INFORMATION: Leu or Met

<400> SEQUENCE: 205

Arg Phe Thr Ile Ser Arg Asp Asn Ser Xaa Asn Thr Leu Tyr Leu Gln
1               5                   10                  15

Met Asn Ser Xaa Arg Ala Glu Asp Thr Ala Val Tyr Tyr Cys Ala
            20                  25                  30

<210> SEQ ID NO 206
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala or Ser
<220> FEATURE:
<221> NAME/KEY: MOD_RES
<222> LOCATION: (3)..(3)
<223> OTHER INFORMATION: Ser or Gly
<220> FEATURE:
<221> NAME/KEY: MOD_RES
<222> LOCATION: (4)..(4)
<223> OTHER INFORMATION: Gly, Ser or Thr
<220> FEATURE:
<221> NAME/KEY: MOD_RES
<222> LOCATION: (5)..(5)
<223> OTHER INFORMATION: Ser or Lys
<220> FEATURE:
<221> NAME/KEY: MOD_RES
<222> LOCATION: (7)..(7)
<223> OTHER INFORMATION: Gly or Glu
<220> FEATURE:
<221> NAME/KEY: MOD_RES
<222> LOCATION: (8)..(8)
<223> OTHER INFORMATION: Ser, Gly, Asp or Tyr
<220> FEATURE:
<221> NAME/KEY: MOD_RES
<222> LOCATION: (13)..(13)
<223> OTHER INFORMATION: Asp or Asn

<400> SEQUENCE: 206

Xaa Ile Xaa Xaa Xaa Gly Xaa Xaa Thr Tyr Tyr Ala Xaa Ser Val Lys
1               5                   10                  15

Gly

<210> SEQ ID NO 207
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Leu or Met

<400> SEQUENCE: 207
```

```
Arg Phe Thr Ile Ser Arg Asp Asn Ser Lys Asn Thr Leu Tyr Leu Gln
1               5                   10                  15

Met Asn Ser Xaa Arg Ala Glu Asp Thr Ala Val Tyr Tyr Cys Ala
            20                  25                  30
```

<210> SEQ ID NO 208
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 208

```
His His His His His His
1               5
```

<210> SEQ ID NO 209
<211> LENGTH: 6
<212> TYPE: PRT
<213> ORGANISM: Homo sapiens

<400> SEQUENCE: 209

```
Ser Ser Tyr Ala Met Ser
1               5
```

<210> SEQ ID NO 210
<211> LENGTH: 17
<212> TYPE: PRT
<213> ORGANISM: Homo sapiens

<400> SEQUENCE: 210

```
Ala Ile Ser Gly Ser Gly Gly Ser Thr Tyr Tyr Ala Asp Ser Val Lys
1               5                   10                  15

Gly
```

<210> SEQ ID NO 211
<211> LENGTH: 10
<212> TYPE: PRT
<213> ORGANISM: Homo sapiens

<400> SEQUENCE: 211

```
Cys Ala Lys Ser Tyr Gly Ala Phe Asp Tyr
1               5                   10
```

<210> SEQ ID NO 212
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

```
Cys Ala Glu Pro Lys Pro Met Asp Thr Glu Phe Asp Tyr
1               5                   10
```

<210> SEQ ID NO 213
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Cys Ala Glu Pro Ser His Phe Asp Arg Pro Phe Asp Tyr
1               5                   10

<210> SEQ ID NO 214
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Cys Ala Gln Thr Val Asn Val Pro Glu Pro Ala Phe Ala Tyr
1               5                   10

<210> SEQ ID NO 215
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Cys Ala Lys Gln Arg Gly Leu Asn Arg Tyr Arg Ala Gln Phe Asp Tyr
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Cys Ala Lys Gln Gly Gln Ile Ser Asn Phe Pro Arg Phe Asp Tyr
1               5                   10                  15

<210> SEQ ID NO 217
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Cys Ala Lys Phe Asn Arg Phe Ser His Arg Gln Tyr Asn Phe Asp Tyr
1               5                   10                  15

<210> SEQ ID NO 218
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Cys Ala Lys Val His Thr Phe Ala Asn Arg Ser Leu Asn Phe Asp Tyr
1               5                   10                  15

<210> SEQ ID NO 219
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 219

Gly Ala Tyr Ser Met Ser
1               5

<210> SEQ ID NO 220
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Cys Ala Lys Cys Ser Ser Cys Thr Ser Leu Asn Ala Asn Phe Asp Tyr
1               5                   10                  15

<210> SEQ ID NO 221
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Cys Ala Lys Ala Ser Ala Pro Lys Tyr Phe Arg Phe Asp Tyr
1               5                   10

<210> SEQ ID NO 222
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Cys Ala Lys Pro Trp Arg Val Tyr Ser Tyr Asp Arg Phe Asp Tyr
1               5                   10                  15

<210> SEQ ID NO 223
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Cys Ala Lys Leu Gln Arg Tyr Asp Arg Tyr Thr Leu Asn Phe Asp Tyr
1               5                   10                  15

<210> SEQ ID NO 224
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Glu Val Gln Leu Leu Glu Pro Gly Gly Gly Leu Val Gln Pro Gly Gly
1               5                   10                  15
```

```
Ser Leu Arg Leu Ser Cys Ala Ala Ser Gly Val Asn Val Ser His Asp
            20                  25                  30

Ser Met Thr Trp Val Arg Gln Ala Pro Gly Lys Gly Leu Glu Trp Val
        35                  40                  45

Ser Ala Ile Arg Gly Pro Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Ser Gly Ala Arg His Ala Asp Thr Glu Arg Pro Pro Ser Gln Gln
                100                 105                 110

Thr Met Pro Phe Trp Gly Gln Gly Thr Leu Val Thr Val Ser Ser
            115                 120                 125
```

ANTI P2X7 RECEPTOR ANTIBODIES AND FRAGMENTS THEREOF

CROSS-REFERENCE TO RELATED APPLICATIONS

The present application is a continuation of U.S. application Ser. No. 16/032,973 filed Jul. 11, 2018, which is a continuation of U.S. application Ser. No. 15/599,396 filed May 18, 2017 now U.S. Pat. No. 10,053,508, which is a continuation of U.S. application Ser. No. 14/671,254 filed Mar. 27, 2015 now U.S. Pat. No. 9,688,771, which is a continuation of U.S. application Ser. No. 13/391,619 filed Feb. 21, 2012 now U.S. Pat. No. 9,688,771, which is the national stage of PCT/AU2010/001070 filed Aug. 20, 2010, each incorporated by reference in its entirety for all purposes, which claims priority to Australian Application No. 2009903928 filed Aug. 20, 2009.

REFERENCE TO SEQUENCE LISTING

This application includes an electronic sequence listing in a file named 554704SEQLST.TXT, created on Mar. 10, 2021 and containing 104,241 bytes, which is incorporated by reference.

FIELD OF THE INVENTION

The invention relates to purinergic receptors, to antibodies and related fragments thereof for binding to said receptors, to production of said antibodies and fragments and to use of said antibodies and fragments for cancer detection and therapy.

BACKGROUND OF THE INVENTION

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

Purinergic (P2X) receptors are ATP-gated cation-selective channels. Each receptor is made up of three protein subunits or monomers. To date seven separate genes encoding P2X monomers have been identified: P2X1, P2X2, P2X3, P2X4, P2X5, P2X6, $P2X_7$.

$P2X_7$ receptors are of particular interest as the expression of these receptors is understood to be limited to cells having potential to undergo programmed cell death, such as thymocytes, dendritic cells, lymphocytes, macrophages and monocytes. There is some expression of $P2X_7$ receptors in normal homeostasis, such as on erythrocytes.

Interestingly, a $P2X_7$ receptor containing one or more monomers having a cis isomerisation at Pro210 (according to SEQ ID NO: 1) and which is devoid of ATP binding function has been found on cells that are understood to be unable to undergo programmed cell death, such as preneoplastic cells and neoplastic cells. This isoform of the receptor has been referred to as a "non functional" receptor.

Antibodies generated from immunisation with a peptide including Pro210 in cis bind to non functional $P2X_7$ receptors. However, they do not bind to $P2X_7$ receptors capable of binding ATP. Accordingly, these antibodies are useful for selectively detecting many forms of carcinoma and haemopoietic cancers and to treatment of some of these conditions.

WO02/057306A1 and WO03/020762A1 both discuss a probe for distinguishing between functional $P2X_7$ receptors and non functional $P2X_7$ receptors in the form of a monoclonal antibody.

WO2009./033233 discusses an epitope present on non functional receptors but not functional receptors and antibodies for binding thereto.

To date it has been very difficult to obtain serological reagents that bind to non functional $P2X_7$ receptors on live cells with desirable affinity. Higher affinity reagents are generally desirable in applications for the detection and treatment of cancer.

There is a need for improved reagents for binding to $P2X_7$ receptors, particularly for new antibodies and fragments thereof that are capable of discriminating between ATP and non-ATP binding $P2X_7$ receptors on live cells.

SUMMARY OF THE INVENTION

In one embodiment there is provided an antigen binding site for binding to a $P2X_7$ receptor, the antigen binding site being defined by general formula 1:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has a sequence selected from the group consisting of: DNEPMG, RNHDMG, SGYAMA, GMYNMS, PASNMS, GSYAMA, GAYAMS, DGYNMS, TYDMAW, QEYGMG, ARYPMA, SSYAMA, AKYPMV, SSYAMS, DNVEMS and PMKDMG.

In one embodiment there is provided an antigen binding site for binding to a $P2X_7$ receptor, the antigen binding site being defined by general formula 2:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR2 has a sequence selected from the group consisting of:

```
SIADSGNHTYYADSVKG,  AISGSGGSTYYADSVKG,
TILSDGSRTYYADSVKG,  SINATGGRTYYADSVKG,
SITASGYRTYYADSVKG,  TISTSGSSTYYADSVKG,
TINGSGLATYYADSVKG,  SITANGNSTYYADSVKG,
SIAAAGSRTYYADSVKG,  SITPSGDKTYYADSVKG,
SIDGGGLQTYYADSVKG,  TIDGNGLITYYADSVKG,
SIGPGGARTYYADSVKG,  TITSDGLRTYYADSVKG,
SIGSKGEDTYYADSVKG,  AISGSGGSTYYANSVKG,
```

-continued

```
AISGSGGGTYYADSVKG, SIGTKGEYTYYADSVKG,

SIGSKGEYTYYADSVKG
and

AISGSGGGTYYANSVKG.
```

In one embodiment there is provided an antigen binding site for binding to a P2X$_7$ receptor, the antigen binding site being defined by general formula 3:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has a sequence selected from the group consisting of:

```
KQRGLNRYRAQFDY, EPKPMDTEFDY, KIKTFRNHSVQFDY,

KFNGFSHRQYNFDY, KQGQISNFPRFDY, KVRFATSKSINFDY,

KCSSCTSLNANFDY, KASYSRPYNFQFDY, KQRSISIRPMFDY,

KVRSMSYAHFDFDY, KASAPKYFRFDY, KLQRYDRYTLNFDY,

KPWRVYSYDRFDY, KVHTFANRSLNFDY, QTVNVPEPAFAY
and

EPSHFDRPFDY.
```

In one embodiment there is provided an antigen binding site for binding to a P2X$_7$ receptor, the antigen binding site being defined by general formula 4:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has a sequence selected from the group consisting of: (P/R)(N/M)(H/K)DMG.

In one embodiment there is provided an antigen binding site for binding to a P2X$_7$ receptor, the antigen binding site being defined by general formula 5:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR2 has a sequence selected from the group consisting of:

```
           AISGSGG(S/G)TYYA(D/N)SVKG.
```

In one embodiment there is provided an antigen binding site for binding to a P2X$_7$ receptor, the antigen binding site being defined by general formula 6:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has a sequence selected from the group consisting of:

```
           EP(K/S)(P/H)(M/F)D(T/R)(E/P)FDY.
```

In one embodiment there is provided an antigen binding site for binding to a P2X$_7$ receptor, the antigen binding site being defined by general formula 7:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:

```
CDR3 has a sequence:
EP(K/S)(P/H)(M/F)D(T/R)(E/P)FDY;
and

FR4 has a sequence:
(W/R/P/G/C)(G/S/F)(Q/P/C)GT(L/Q)VTV(S/L)(S/E).
```

In one embodiment there is provided an antigen binding site for binding to a P2X$_7$ receptor, the antigen binding site being defined by general formula 8:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:

```
CDR1 has a sequence:
(P/R)(N/M)(H/K)DMG;

CDR2 has a sequence:
AISGSGG(S/G)TYYA(D/N)SVKG;

CDR3 has a sequence:
EP(K/S)(P/H)(M/F)D(T/R)(E/P)FDY;
and

FR4 has a sequence:
(W/R/P/G/C)(G/S/F)(Q/P/C)GT(L/Q)VTV(S/L)(S/E).
```

In one embodiment there is provided an antigen binding site for binding to a P2X$_7$ receptor, the antigen binding site being defined by general formula 9:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:

```
CDR1 has a sequence:
(P/R)(N/M)(H/K)DMG;

CDR2 has a sequence:
AISGSGG(S/G)TYYA(D/N)SVKG;

CDR3 has a sequence:
EP(K/S)(P/H)(M/F)D(T/R)(E/P)FDY;
```

-continued

```
FR1 has a sequence:
EVQLLE(S/P)GGGLVQPGGSLRLSCAASG(Y/F/V)(R/T/N)

(I/F/V);

FR2 has a sequence:
W(V/A)RQAPGKGLEW(V/A)S;

FR3 has a sequence:
RFTISRDNS(R/K)NTLYLQMNS(L/M)RAEDTAVYYCA;

FR4 has a sequence:
(W/R/P/G/C)(G/S/F)(Q/P/C)GT(L/Q)VTV(S/L)(S/E).
```

In one embodiment there is provided an antigen binding site for binding to a P2X$_7$ receptor, the antigen binding site being defined by general formula 10:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:

```
CDR1 has a sequence:
PMKDMG;

CDR2 has a sequence:
AISGSGGGTYYADSVKG;

CDR3 has a sequence:
EPKPMDTEFDY;

FR1 has a sequence:
EVQLLESGGGLVQPGGSLRLSCAASGYTF;

FR2 has a sequence:
WVRQAPGKGLEWVS;

FR3 has a sequence:
RFTISRDNSKNTLYLQMNSLRAEDTAVYYCA;

FR4 has a sequence:
PSPGTLVTVLE, WGQGTLVTVSS, WGQGTLVTVLS,

RSPGTLVTVSS, PSPGTQVTVSS, PSPGTLVTVSS,

RSQGTLVTVSS, WSQGTLVTVSS, RGQGTLVTVSS,

RFQGTLVTVSS, WSPGTLVTVSS, GSPGTLVTVSS,

WGPGTLVTVSS, RGPGTLVTVSS, CGPGTLVTVSS,

RSCGTLVTVSS,
or

RSPGTLVTVLE.
```

In other embodiments there is provided an antigen binding site having a sequence as described herein, or including a CDR and/or FR sequence as described herein and including one or more mutations for increasing the affinity of said site for binding to a P2X$_7$ receptor.

In another embodiment there is provided an antigen binding site as described herein wherein an amino acid sequence forming one or more of FR1, CDR1, FR2, CDR2, FR3, CDR3 and FR4 is a human sequence.

In another embodiment there is provided an anti P2X$_7$ receptor immunoglobulin variable domain, antibody, Fab, dab, scFv including an antigen binding site having a sequence as described herein, or including a CDR and/or FR sequence as described herein.

In another embodiment there is provided a diabody or triabody including an antigen binding site having a sequence as described herein, or including a CDR and/or FR sequence as described herein.

In another embodiment there is provided a fusion protein including an antigen binding site, immunoglobulin variable domain, antibody, Fab, dab, scFv, diabody or triabody as described herein.

In another embodiment there is provided a conjugate in the form of an antigen binding site, immunoglobulin variable domain, antibody, Fab, dab, scFv, diabody, triabody or fusion protein as described herein conjugated to a label or a cytotoxic agent.

In another embodiment there is provided an antibody for binding to an antigen binding site of an immunoglobulin variable domain, antibody, Fab, dab, scFv, diabody, triabody, fusion protein, or conjugate as described herein.

In another embodiment there is provided a nucleic acid encoding an antigen binding site, or a CDR and/or FR sequence as described herein, or an immunoglobulin variable domain, antibody, Fab, dab, scFv, diabody, triabody, fusion protein or conjugate as described herein.

In another embodiment there is provided a vector including a nucleic acid described herein.

In another embodiment there is provided a cell including a vector or nucleic acid described herein.

In another embodiment there is provided an animal or tissue derived therefrom including a cell described herein.

In another embodiment there is provided a pharmaceutical composition including an antigen binding site, or including a CDR and/or FR sequence as described herein, or an immunoglobulin variable domain, antibody, Fab, dab, scFv, diabody, triabody, fusion protein, or conjugate as described herein and a pharmaceutically acceptable carrier, diluent or excipient.

In another embodiment there is provided a diagnostic composition including an antigen binding site, or including a CDR and/or FR sequence as described herein, or an immunoglobulin variable domain, antibody, Fab, dab, scFv, diabody, triabody, fusion protein or conjugate as described herein, a diluent and optionally a label.

In another embodiment there is provided a kit or article of manufacture including an antigen binding site, or including a CDR and/or FR sequence as described herein or an immunoglobulin variable domain, antibody, Fab, dab, scFv, diabody, triabody, fusion protein or conjugate as described herein.

In another embodiment there is provided a use of a sequence according to one or more of CDR1, CDR2, FR1, FR2, FR3 and FR4 as described herein to produce an antigen binding site for binding to a P2X$_7$ receptor.

In another embodiment there is provided a use of an antigen binding site or a CDR and/or FR sequence as described herein to produce an anti P2X$_7$ receptor antigen binding site having increased affinity for P2X$_7$ receptor.

In another embodiment there is provided a library of nucleic acid molecules produced from the mutation of an antigen binding site or a CDR and/or FR sequence as described herein, wherein at least one nucleic acid molecule in said library encodes an antigen binding site for binding to an a P2X$_7$ receptor.

In another embodiment there is provided a method for producing an anti P2X$_7$ antigen binding site as described herein including expressing a nucleic acid as described herein in a cell or animal as described herein.

In another embodiment there is provided a method for the treatment of cancer or a condition or disease associated with expression of non functional P2X$_7$ receptor in an individual including the step of providing an antigen binding site, immunoglobulin variable domain, antibody, Fab, dab, scFv, diabody, triabody, fusion protein, conjugate or pharmaceutical composition as described herein to an individual requiring treatment for cancer or said condition or disease.

In another embodiment there is provided a use of an antigen binding site, immunoglobulin variable domain, antibody, Fab, dab, scFv, diabody, triabody, fusion protein, conjugate or pharmaceutical composition as described herein in the manufacture of a medicament for the treatment of cancer or a condition or disease associated with expression of non functional P2X$_7$ receptor.

In another embodiment there is provided a method for the diagnosis of cancer or disease or condition associated with expression of non functional P2X$_7$ receptor, including the step of contacting tissues or cells for which the presence or absence of cancer is to be determined with a reagent in the form of an antigen binding site, immunoglobulin variable domain, antibody, Fab, dab, scFv, diabody, triabody, fusion protein, conjugate or diagnostic composition as described herein and detecting for the binding of the reagent with the tissues or cells. The method may be operated in vivo or in vitro.

Typically the antigen binding sites according to the invention bind to non functional P2X$_7$ receptors, especially receptors wherein Pro210 of P2X$_7$ is in cis conformation. In certain embodiments the antigen binding sites according to the invention do not bind to functional P2X$_7$ receptors, especially receptors wherein Pro210 of P2X$_7$ is in trans conformation.

Typically the antigen binding sites according to the invention bind to non functional P2X$_7$ receptors on live cells. In other embodiments, the antigen binding site does not bind to receptors on dead or fixed cells tissues, such as those as studied in histology or cytology.

In one embodiment, the antigen binding sites according to the invention bind to P2X$_7$ receptors on live cells with affinities in the range of 0.1 to 5 nM.

In one embodiment, there is provided a single domain antibody including an antigen binding site for binding to a P2X$_7$ receptor, preferably to a non functional P2X$_7$ receptor.

BRIEF DESCRIPTION OF THE DRAWINGS

FIG. 32. Flow cytometry of human lymphocytes and monocytes from PBMC showing no binding by PEP2-2-1 Fc or PEP2-2-3 Fc.

FIG. 41. (SEQ ID NO:1) Sequence of $P2X_7$.

FIG. 42. (SEQ ID NO:2) Sequence of ECD2

FIG. 43 (SEQ ID NO:3) Sequence of ECD1.

FIGS. 45A-C(SEQ ID NO: 198) Sequence of pcDNA3.1 PEP2-2-1 dAb-FC.

DETAILED DESCRIPTION OF THE EMBODIMENTS

Figure 1:
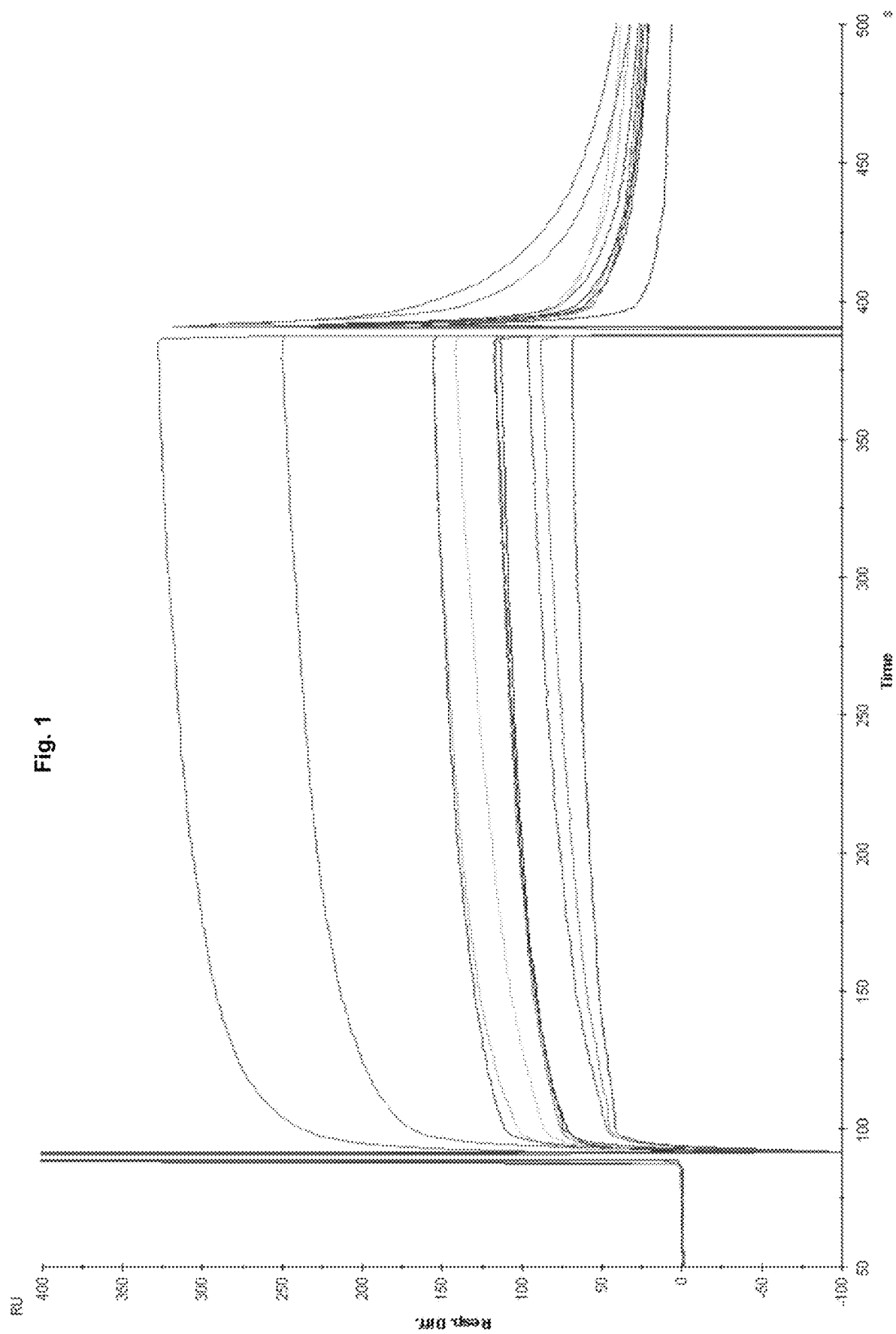
FIG. 1. Round 2 dAb ELISA positives screened on Biacore from the Round 2 phage

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

As used herein, except where the context requires otherwise, the term "comprise" and variations of the term, such as "comprising", "comprises" and "comprised", are not intended to exclude further additives, components, integers or steps.

For purposes of interpreting this specification, the following definitions will apply and whenever appropriate, terms used in the singular will also include the plural and vice versa. In the event that any definition set forth conflicts with any document incorporated herein by reference, the definition set forth below shall prevail.

"Purinergic receptor" generally refers to a receptor that uses a purine (such as ATP) as a ligand.

"$P2X_7$ receptor" generally refers to a purinergic receptor formed from three protein subunits or monomers, with at least one of the monomers having an amino acid sequence substantially as shown in SEQ ID NO:1. "$P2X_7$ receptor" may be a functional or non functional receptor as described below. "$P2X_7$ receptor" encompasses naturally occurring variants of $P2X_7$ receptor, e.g., wherein the $P2X_7$ monomers are splice variants, allelic variants and isoforms including naturally-occurring truncated or secreted forms of the monomers forming the $P2X_7$ receptor (e.g., a form consisting of the extracellular domain sequence or truncated form of it), naturally-occurring variant forms (e.g., alternatively spliced forms) and naturally-occurring allelic variants. In certain embodiments of the invention, the native sequence $P2X_7$ monomeric polypeptides disclosed herein are mature or full-length native sequence polypeptides comprising the full-length amino acids sequence shown in SEQ ID NO:1. In certain embodiments the $P2X_7$ receptor may have an amino acid sequence that is modified, for example various of the amino acids in the sequence shown in SEQ ID NO:1 may be substituted, deleted, or a residue may be inserted.

"Functional $P2X_7$ receptor" generally refers to a form of the $P2X_7$ receptor having a binding site or cleft for binding to ATP. When bound to ATP, the receptor forms a pore—like structure that enables the ingress of calcium ions into the cytosol, one consequence of which may be programmed cell death. In normal homeostasis, expression of functional $P2X_7$ receptors is generally limited to cells that undergo programmed cell death such as thymocytes, dendritic cells, lymphocytes, macrophages and monocytes. There may also be some expression of functional $P2X_7$ receptors on erythrocytes.

"Non functional $P2X_7$ receptor" generally refers to a form of a $P2X_7$ receptor in which one or more of the monomers has a cis isomerisation at Pro210 (according to SEQ ID NO:1). The isomerisation may arise from any molecular event that leads to misfolding of the monomer, including for example, mutation of monomer primary sequence or abnormal post translational processing. One consequence of the isomerisation is that the receptor is unable to bind to ATP, or otherwise binds ATP with a lower affinity than observed between ATP and receptors which do not contain an isomerisation at Pro210. In the circumstances, the receptor cannot form a pore and this limits the extent to which calcium ions may enter the cytosol. Non functional $P2X_7$ receptors are expressed on a wide range of epithelial and haematopoietic cancers.

"Extracellular domain" (ECD) used herein are $P2X_7$ receptor (47-306) (SEQ ID NO: 2) (ECD2) and $P2X_7$ receptor (47-332) (SEQ ID NO:3) (ECD1). $P2X_7$ receptor (47-306) (SEQ ID NO: 2) is amino acids 47 to 306 of SEQ ID NO: 1. $P2X_7$ receptor (47-332) (SEQ ID NO:3) is amino acids 47 to 332 of SEQ ID NO: 1.

"Antibodies" or "immunoglobulins" or "Igs" are gamma globulin proteins that are found in blood, or other bodily fluids of verterbrates that function in the immune system to bind antigen, hence identifying and neutralizing foreign objects.

Antibodies are generally a heterotetrameric glycoprotein composed of two identical light (L) chains and two identical heavy (H) chains. Each L chain is linked to a H chain by one covalent disulfide bond. The two H chains are linked to each other by one or more disulfide bonds depending on the H chain isotype. Each H and L chain also has regularly spaced intrachain disulfide bridges.

H and L chains define specific Ig domains. More particularly, each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H 1$).

Antibodies can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2. The L chain from any vertebrate species can be assigned to one of two clearly distinct types, called kappa and lambda, based on the amino acid sequences of their constant domains.

The constant domain includes the Fc portion which comprises the carboxy-terminal portions of both H chains held together by disulfides. The effector functions of antibodies such as ADCC are determined by sequences in the Fc region, which region is also the part recognized by Fc receptors (FcR) found on certain types of cells.

The pairing of a $V_H$ and $V_L$ together forms a "variable region" or "variable domain" including the amino-terminal domains of the heavy or light chain of the antibody. The variable domain of the heavy chain may be referred to as "VH." The variable domain of the light chain may be referred to as "VL." The V domain contains an antigen binding site which affects antigen binding and defines specificity of a particular antibody for its particular antigen. V regions span about 110 amino acid residues and consist of relatively invariant stretches called framework regions (FRs) (generally about 4) of 15-30 amino acids separated by shorter regions of extreme variability called "hypervariable regions" (generally about 3) that are each 9-12 amino acids long. The FRs largely adopt a β-sheet configuration and the hypervariable regions form loops connecting, and in some cases forming part of, the β-sheet structure.

"Hypervariable region", "HVR", or "HV" refers to the regions of an antibody variable domain which are hypervariable in sequence and/or form structurally defined loops. Generally, antibodies comprise six hypervariable regions; three in the VH (HI, H2, H3), and three in the VL (LI, L2, L3). A number of hypervariable region delineations are in use and are encompassed herein. The Kabat Complementarity Determining Regions (CDRs) are based on sequence variability and are the most commonly used (Kabat et al, Sequences of Proteins of Immunological Interest, 5th Ed. Public Health Service, National Institutes of Health, Bethesda, Md. (1991)).

"Framework" or "FR" residues are those variable domain residues other than the hypervariable region residues herein defined.

"A peptide for forming an antigen binding site" generally refers to a peptide that may form a conformation that confers the specificity of an antibody for antigen. Examples include whole antibody or whole antibody related structures, whole antibody fragments including a variable domain, variable domains and fragments thereof, including light and heavy chains, or fragments of light and heavy chains that include some but not all of hypervariable regions or constant regions.

An "intact" or "whole" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof.

"Whole antibody related structures" include multimerized forms of whole antibody.

"Whole antibody fragments including a variable domain" include Fab, Fab', F(ab')$_2$, and Fv fragments; diabodies; linear antibodies, single-chain antibody molecules; and multispecific antibodies formed from antibody fragments.

The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site.

A Fab' fragment differs from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group.

A F(ab')2 fragment roughly corresponds to two disulfide linked Fab fragments having divalent antigen-binding activity and is still capable of cross-linking antigen.

An "Fv" is the minimum antibody fragment which contains a complete antigen-recognition and—binding site. This fragment consists of a dimer of one heavy- and one light-chain variable region domain in tight, non-covalent association.

In a single-chain Fv (scFv) species, one heavy- and one light-chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody.

"Single-chain Fv" also abbreviated as "sFv" or "scFv" are antibody fragments that comprise the $V_H$ and $V_L$ antibody domains connected to form a single polypeptide chain. Preferably, the scFv polypeptide further comprises a polypeptide linker between the $V_H$ and $V_L$ domains which enables the scFv to form the desired structure for antigen binding.

A "single variable domain" is half of an Fv (comprising only three CDRs specific for an antigen) that has the ability to recognize and bind antigen, although at a lower affinity than the entire binding site "Diabodies" refers to antibody fragments with two antigen-binding sites, which fragments comprise a heavy-chain variable domain (VH) connected to a light-chain variable domain (VL) in the same polypeptide chain (VH-VL). The small antibody fragments are prepared by constructing sFv fragments (see preceding paragraph) with short linkers (about 5-10 residues) between the $V_H$ and $V_L$ domains such that interchain but not intra-chain pairing of the V domains is achieved, resulting in a bivalent fragment, i.e., fragment having two antigen-binding sites.

Diabodies may be bivalent or bispecific. Bispecific diabodies are heterodimers of two "crossover" sFv fragments in which the $V_H$ and $V_L$ domains of the two antibodies are present on different polypeptide chains. Triabodies and tetrabodies are also generally know in the art.

An "isolated antibody" is one which has been identified and separated and/or recovered from a component of its pre-existing environment. Contaminant components are materials that would interfere with therapeutic uses for the antibody, and may include enzymes, hormones, and other proteinaceous or nonproteinaceous solutes.

A "human antibody" refers to an antibody which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Human antibodies can be prepared by administering the antigen to a transgenic animal that has been modified to produce such antibodies in response to antigenic challenge, but whose endogenous loci have been disabled.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

"Monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site or determinant on the antigen. In addition to their specificity, the monoclonal antibodies are advantageous in that they may be synthesized uncontaminated by other antibodies. Monoclonal antibodies may be prepared by the hybridoma methodology, or may be made using recombinant DNA methods in bacterial, eukaryotic animal or plant cells. The "monoclonal antibodies" may also be isolated from phage antibody libraries.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. Chimeric antibodies of interest herein include "primatized" antibodies comprising variable domain antigen-binding sequences derived from a non-human primate (e.g. Old World Monkey, Ape etc), and human constant region sequences.

The term "anti-$P2X_7$ receptor antibody" or "an antibody that binds to $P2X_7$ receptor" refers to an antibody that is capable of binding $P2X_7$ receptor with sufficient affinity such that the antibody is useful as a diagnostic and/or therapeutic agent in targeting $P2X_7$ receptor, typically non functional $P2X_7$ receptor. Preferably, the extent of binding of an $P2X_7$ receptor antibody to an unrelated receptor protein is less than about 10% of the binding of the antibody to $P2X_7$ receptor as measured, e.g., by a radioimmunoassay (RIA). In certain embodiments, an antibody that binds to $P2X_7$ receptor has a dissociation constant (Kd) of <1 µM, <100 nM, <10 nM, <1 nM, or <0.1 nM. An anti non functional $P2X_7$ receptor antibody is generally one having some or all of these serological characteristics and that binds to non functional $P2X_7$ receptors but not to functional $P2X_7$ receptors.

An "affinity matured" antibody is one with one or more alterations in one or more HVRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art.

A "blocking" antibody or an "antagonist" antibody is one which inhibits or reduces biological activity of the antigen it binds. Preferred blocking antibodies or antagonist antibodies substantially or completely inhibit the biological activity of the antigen.

An "agonist antibody", as used herein, is an antibody which mimics at least one of the functional activities of a polypeptide of interest.

"Binding affinity" generally refers to the strength of the sum total of noncovalent interactions between a single binding site of a molecule (e.g., an antibody) and its binding partner (e.g., an antigen). Generally, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

The inventors have determined the CDR sequences of a number of variable domain clones that they have found to bind to the ECD target. These CDR sequences are shown in Table 1 below.

In one embodiment there is provided a peptide having a sequence as shown in Table 1. These peptides are particularly useful for constructing antigen binding sites, variable domains, antibodies and related fragments.

TABLE 1

| CDR sequences | | | |
| --- | --- | --- | --- |
| Clone | CDR1 | CDR2 | CDR3 |
| PEP2-1 | SEQ ID NO: 4<br>DNEPMG | SEQ ID NO: 5<br>SIADSGNHTYYADSVKG | SEQ ID NO: 6<br>KQRGLNRYRAQFDY |
| PEP2-2 | SEQ ID NO: 7<br>RNHDMG | SEQ ID NO: 8<br>AISGSGGSTYYADSVKG | SEQ ID NO: 9<br>EPKPMDTEFDY |

TABLE 1-continued

CDR sequences

| Clone | CDR1 | CDR2 | CDR3 |
|---|---|---|---|
| PEP2-3 | SEQ ID NO: 10<br>SGYAMA | SEQ ID NO: 11<br>TILSDGSRTYYADSVKG | SEQ ID NO: 12<br>KIKTFRNHSVQFDY |
| PEP2-4 | SEQ ID NO: 13<br>GMYNMS | SEQ ID NO: 14<br>SINATGGRTYYADSVKG | SEQ ID NO: 15<br>KFNGFSHRQYNFDY |
| PEP2-5 | SEQ ID NO: 16<br>PASNMS | SEQ ID NO: 17<br>SITASGYRTYYADSVKG | SEQ ID NO: 18<br>KQGQISNFPRFDY |
| PEP2-6 | SEQ ID NO: 19<br>GSYAMA | SEQ ID NO: 20<br>TISTSGSSTYYADSVKG | SEQ ID NO: 21<br>KVRFATSKSINFDY |
| PEP2-7 | SEQ ID NO: 22<br>GAYAMS | SEQ ID NO: 23<br>TINGSGLATYYADSVKG | SEQ ID NO: 24<br>KCSSCTSLNANFDY |
| PEP2-8 | SEQ ID NO: 25<br>DGYNMS | SEQ ID NO: 26<br>SITANGNSTYYADSVKG | SEQ ID NO: 27<br>KASYSRPYNFQFDY |
| PEP2-9 | SEQ ID NO: 28<br>TYDMAW | SEQ ID NO: 29<br>SIAAAGSRTYYADSVKG | SEQ ID NO: 30<br>KQRSISIRPMFDY |
| PEP2-10 | SEQ ID NO: 31<br>QEYGMG | SEQ ID NO: 32<br>SITPSGDKTYYADSVKG | SEQ ID NO: 33<br>KVRSMSYAHFDFDY |
| PEP2-11 | SEQ ID NO: 34<br>ARYPMA | SEQ ID NO: 35<br>SIDGGGLQTYYADSVKG | SEQ ID NO: 36<br>KASAPKYFRFDY |
| PEP2-13 | SEQ ID NO: 37<br>SSYAMA | SEQ ID NO: 38<br>TIDGNGLITYYADSVKG | SEQ ID NO: 39<br>KLQRYDRYTLNFDY |
| PEP2-30 | SEQ ID NO: 40<br>VAKYPMV | SEQ ID NO: 41<br>SIGPGGARTYYADSVKG | SEQ ID NO: 42<br>KPWRVYSYDRFDY |
| PEP2-34 | SEQ ID NO: 43<br>SSYAMS | SEQ ID NO: 44<br>TITSDGLRTYYADSVKG | SEQ ID NO: 45<br>KVHTFANRSLNFDY |
| PEP2-42 | SEQ ID NO: 46<br>DNVEMS | SEQ ID NO: 47<br>SIGSKGEDTYYADSVKG | SEQ ID NO: 48<br>QTVNVPEPAFAY |
| PEP2-47 | SEQ ID NO: 49<br>PMKDMG | SEQ ID NO: 50<br>AISGSGGSTYYADSVKG | SEQ ID NO: 51<br>EPSHFDRPFDY |
| PEP2-2-1 | SEQ ID NO: 52<br>RNHDMG | SEQ ID NO: 53<br>AISGSGGSTYYANSVKG | SEQ ID NO: 54<br>EPKPMDTEFDY |
| PEP2-2-1-1 | SEQ ID NO: 55<br>VRNHDMG | SEQ ID NO: 56<br>AISGSGGSTYYADSVKG | SEQ ID NO: 57<br>EPKPMDTEFDY |
| PEP2-2-1-2 | SEQ ID NO: 58<br>RNHDMG | SEQ ID NO: 59<br>AISGSGGSTYYADSVKG | SEQ ID NO: 60<br>EPKPMDTEFDY |
| PEP2-2-11 | SEQ ID NO: 61<br>RNHDMG | SEQ ID NO: 62<br>AISGSGGSTYYANSVKG | SEQ ID NO: 63<br>EPKPMDTEFDY |
| PEP2-2-12 | SEQ ID NO: 64<br>RNHDMG | SEQ ID NO: 65<br>AISGSGGSTYYANSVKG | SEQ ID NO: 66<br>EPKPMDTEFDY |
| PEP2-2-2 | SEQ ID NO: 67<br>RNHDMG | SEQ ID NO: 68<br>AISGSGGSTYYADSVKG | SEQ ID NO: 69<br>EPKPMDTEFDY |
| PEP2-2-4 | SEQ ID NO: 70<br>RNHDMG | SEQ ID NO: 71<br>AISGSGGSTYYADSVKG | SEQ ID NO: 72<br>EPKPMDTEFDY |
| PEP2-2-5 | SEQ ID NO: 73<br>RNHDMG | SEQ ID NO: 74<br>AISGSGGSTYYADSVKG | SEQ ID NO: 75<br>EPKPMDTEFDY |
| PEP2-2-8 | SEQ ID NO: 76<br>RNHDMG | SEQ ID NO: 77<br>AISGSGGSTYYADSVKG | SEQ ID NO: 78<br>EPKPMDTEFDY |
| PEP2-2-9 | SEQ ID NO: 79<br>RNHDMG | SEQ ID NO: 80<br>AISGSGGSTYYADSVKG | SEQ ID NO: 81<br>EPKPMDTEFDY |

TABLE 1-continued

CDR sequences

| Clone | CDR1 | CDR2 | CDR3 |
|---|---|---|---|
| PEP2-2-81 | SEQ ID NO: 82 RNHDMG | SEQ ID NO: 83 AISGSGGSTYYADSVKG | SEQ ID NO: 84 EPKPMDTEFDY |
| PEP2-2-91 | SEQ ID NO: 85 RNHDMG | SEQ ID NO: 86 AISGSGGSTYYADSVKG | SEQ ID NO: 87 EPKPMDTEFDY |
| PEP2-2-3 | SEQ ID NO: 88 RNHDMG | SEQ ID NO: 89 AISGSGGSTYYADSVKG | SEQ ID NO: 90 EPKPMDTEFDY |
| PEP2-2-31 | SEQ ID NO: 91 RNHDMG | SEQ ID NO: 92 AISGSGGSTYYADSVKG | SEQ ID NO: 93 EPKPMDTEFDY |
| PEP2-2-32 | SEQ ID NO: 94 RNHDMG | SEQ ID NO: 95 AISGSGGSTYYADSVKG | SEQ ID NO: 96 EPKPMDTEFDY |
| PEP2-2-33 | SEQ ID NO: 97 RNHDMG | SEQ ID NO: 98 AISGSGGSTYYADSVKG | SEQ ID NO: 99 EPKPMDTEFDY |
| PEP2-2-10 | SEQ ID NO: 100 RNHDMG | SEQ ID NO: 101 AISGSGGSTYYADSVKG | SEQ ID NO: 102 EPKPMDTEFDY |
| PEP2-2-101 | SEQ ID NO: 103 RNHDMG | SEQ ID NO: 104 AISGSGGSTYYADSVKG | SEQ ID NO: 105 EPKPMDTEFDY |
| PEP2-2-102 | SEQ ID NO: 106 RNHDMG | SEQ ID NO: 107 AISGSGGSTYYADSVKG | SEQ ID NO: 108 EPKPMDTEFDY |
| PEP2-247-1 | SEQ ID NO: 109 RNHDMG | SEQ ID NO: 110 AISGSGGGTYYADSVKG | SEQ ID NO: 111 EPSHFDRPFDY |
| PEP2-247-2 | SEQ ID NO: 112 RNHDMG | SEQ ID NO: 113 AISGSGGSTYYANSVKG | SEQ ID NO: 114 EPSHFDRPFDY |
| PEP2-472-1 | SEQ ID NO: 115 PMKDMG | SEQ ID NO: 116 AISGSGGGTYYADSVKG | SEQ ID NO: 117 EPKPMDTEFDY |
| PEP2-472-11 | SEQ ID NO: 118 PMKDMG | SEQ ID NO: 119 AISGSGGGTYYADSVKG | SEQ ID NO: 120 EPKPMDTEFDY |
| PEP2-472-12 | SEQ ID NO: 121 PMKDMG | SEQ ID NO: 122 AISGSGGGTYYADSVKG | SEQ ID NO: 123 EPKPMDTEFDY |
| PEP2-472-121 | SEQ ID NO: 124 PMKDMG | SEQ ID NO: 125 AISGSGGGTYYADSVKG | SEQ ID NO: 126 EPKPMDTEFDY |
| PEP2-42-1 | SEQ ID NO: 127 DNVEMS | SEQ ID NO: 128 SIGTKGEYTYYADSVKG | SEQ ID NO: 129 QTVNVPEPAFAY |
| PEP2-42-2 | SEQ ID NO: 130 DNVEMS | SEQ ID NO: 131 SIGSKGEYTYYADSVKG | SEQ ID NO: 132 QTVNVPEPAFAY |
| PEP2-47-1 | SEQ ID NO: 133 PMKDMG | SEQ ID NO: 134 AISGSGGGTYYADSVKG | SEQ ID NO: 135 EPSHFDRPFDY |
| PEP2-47-2 | SEQ ID NO: 136 PMKDMG | SEQ ID NO: 137 AISGSGGGTYYANSVKG | SEQ ID NO: 138 EPSHFDRPFDY |

The inventors have determined the FR sequences of a number of variable domain clones that they have found to bind to the ECD target. These FR sequences are shown in Table 2 below. Other known FR sequences could be used with the above described CDRs to form an antigen binding site for binding to a non functional P2X$_7$ receptor.

TABLE 2

Framework regions

| Clone | FR1 |
|---|---|
| PEP2-1, PEP2-2, PEP2-3, PEP2-4, PEP2-5, PEP2-6, PEP2-7, PEP2-8, PEP2-10, PEP2-11, PEP2-13, PEP2-30, PEP2-34, PEP2-42, PEP2-47, PEP2-2-1, PEP2-2-1-1, PEP2-2-1-2, PEP2-2-11, PEP2-2-12, PEP2-2-2, PEP2-2-8, PEP2-2-9, PEP2-2-81, PEP2-2-91, PEP2-2-3, PEP2-2-31, PEP2-2-32, PEP2-2-33, PEP2-2-10, PEP2-2-101, | SEQ ID NO: 139 EVQLLESGGGLVQPGGSLRLSCAASGFTF |

TABLE 2-continued

| Framework regions | |
|---|---|
| PEP2-2-102, PEP2-247-1, PEP2-247-2, PEP2-42, PEP2-42-1; PEP2-2-5 | |
| HEL-4 | SEQ ID NO: 140<br>EVQLLESGGGLVQPGGSLRLSCAASGFRI |
| PEP2-9 | SEQ ID NO: 141<br>EVQLLESGGGLVQPGGSLRLSCAASGFTL |
| PEP2-47-1, PEP2-47-2, PEP2-472-1, PEP2-472-11, PEP2-472-12; PEP2-472-121 | SEQ ID NO: 142<br>EVQLLESGGGLVQPGGSLRLSCAASGYTF |
| PEP2-2-4 | SEQ ID NO: 143<br>EVQLLESGGGLVQPGGSLRLTCAASGFSF |
| PEP2-42-2 | SEQ ID NO: 144<br>EVQMLESGGGLVQPGESLRLSCAASGFTF |

| Clone | FR2 |
|---|---|
| PEP2-1, PEP2-2, PEP2-4, PEP2-5, PEP2-6, PEP2-7, PEP2-9, PEP2-10, PEP2-11, PEP2-13, PEP2-30, PEP2-34, PEP2-42, PEP2-47, PEP2-2-1, PEP2-2-1-1, PEP2-2-1-2, PEP2-2-11, PEP2-2-12, PEP2-2-2, PEP2-2-4, PEP2-2-5, PEP2-2-8, PEP2-2-9, PEP2-2-81, PEP2-2-91, PEP2-2-3, PEP2-2-31, PEP2-2-32, PEP2-2-33, PEP2-2-10, PEP2-2-101, PEP2-2-102, PEP2-472-1, PEP2-472-11, PEP2-472-12, PEP2-472-121, PEP2-247-1, PEP2-247-2, PEP2-42-1, PEP2-42-2, PEP2-47-1, PEP2-47-2 | SEQ ID NO: 145<br>WVRQAPGKGLEWVS |
| PEP2-3 | SEQ ID NO: 146<br>WVRQAPGKGLEWAS |
| PEP2-8 | SEQ ID NO: 147<br>WARQAPGKGLEWVS |

| Clone | FR3 |
|---|---|
| PEP2-1, PEP2-2, PEP2-3, PEP2-4, PEP2-5, PEP2-6, PEP2-7, PEP2-8, PEP2-9, PEP2-10, PEP2-11, PEP2-13, PEP2-30, PEP2-42, PEP2-47, PEP2-2-1, PEP2-2-1-1, PEP2-2-1-2, PEP2-2-11, PEP2-2-12, PEP2-2-2, PEP2-2-4, PEP2-2-8, PEP2-2-9, PEP2-2-81, PEP2-2-91, PEP2-2-3, PEP2-2-31, PEP2-2-32, PEP2-2-33, PEP2-2-10, PEP2-2-101, PEP2-2-102, PEP2-472-1, PEP2-472-11, PEP2-472-12, PEP2-472-121, PEP2-247-1, PEP2-247-2, PEP-2-47-1, PEP-2-47-2 | SEQ ID NO: 148<br>RFTISRDNSKNTLYLQMNSLRAEDTAVYYCA |
| PEP2-34 | SEQ ID NO: 149<br>RFTISRDNSRNTLYLQMNSLRAEDTAVYYCA |
| PEP2-42-1 | SEQ ID NO: 150<br>RFTISRDNSKNTLYLQMNSMRAEDTAVYYCA |
| PEP2-42-2 | SEQ ID NO: 151<br>RFTISRDNSKNTLYLQMNSPRAEDTAVYYCA |
| PEP2-2-5 | SEQ ID NO: 152<br>RFTISRDDSKNTLYLQMNSLRAEDTAVYYCA |

| Clone | FR4 |
|---|---|
| PEP2-1, PEP2-2, PEP2-3, PEP2-4, PEP2-5, PEP2-6, PEP2-7, PEP2-8, PEP2-9, PEP2-10, PEP2-11, PEP2-13, PEP2-30, PEP2-34, PEP2-42, PEP2-47, PEP2-42-2 | SEQ ID NO: 153<br>WGQGTLVTVSS |
| PEP2-42-1 | SEQ ID NO: 154<br>WGQGTLVTVLS |
| PEP2-2-1, PEP2-2-1-1, PEP2-2-32, PEP2-2-4, PEP2-2-5 | SEQ ID NO: 155<br>RSPGTLVTVSS |
| PEP2-2-11 | SEQ ID NO: 156<br>PSPGTQVTVSS |
| PEP2-2-12, PEP2-2-31 | SEQ ID NO: 157<br>PSPGTLVTVSS |

TABLE 2-continued

| Framework regions | |
|---|---|
| PEP2-2-2, PEP2-47-1, PEP2-47-2, PEP2-472-1, PEP2-247-1, PEP2-247-2 | SEQ ID NO: 158<br>RSQGTLVTVSS |
| PEP2-2-8, PEP2-2-81 | SEQ ID NO: 159<br>WSQGTLVTVSS |
| PEP2-2-9, | SEQ ID NO: 160<br>RGQGTLVTVSS |
| PEP2-2-91 | SEQ ID NO: 161<br>RFQGTLVTVSS |
| PEP2-2-3 | SEQ ID NO: 162<br>WSPGTLVTVSS |
| PEP2-2-33 | SEQ ID NO: 163<br>GSPGTLVTVSS |
| PEP2-2-10 | SEQ ID NO: 164<br>WGPGTLVTVSS |
| PEP2-2-101 | SEQ ID NO: 165<br>RGPGTLVTVSS |
| PEP2-2-102 | SEQ ID NO: 166<br>CGPGTLVTVSS |
| PEP2-472-11 | SEQ ID NO: 167<br>RSCGTLVTVSS |
| PEP2-472-12 | SEQ ID NO: 168<br>RSPGTLVTVLE |
| PEP2-472-121 | SEQ ID NO: 169<br>PSPGTLVTVLE |
| PEP2-2-1-2 | SEQ ID NO: 170<br>RSQGTLVTVSS |

In certain embodiments there is provided an antigen binding site having a sequence shown in Table 3 below:

TABLE 3

| Antigen binding sites | |
|---|---|
| Clone | Antigen binding site sequence |
| PEP2-2 | SEQ ID NO: 171<br>PEP2-2<br>EVQLLESGGGLVQPGGSLRLSCAASGFRIRNHDMGWVRQAPGKGLEWVSAISGSGGSTYYADSVKGRFTISRDNSKNTLYLQMNSLRAED<br>TAVYYCAEPKPMDTE-FDYWGQGTLVTVSS |
| PEP2-42 | SEQ ID NO: 172<br>PEP2-42<br>EVQLLESGGGLVQPGGSLRLSCAASGFTFDNVEMSWVRQAPGKGLEWVSSIGSKGEDTYYADSVKGRFTISRDNSKNTLYLQMNSLRAED<br>TAVYYCAQTVNVPEPAFAYWGQGTLVTVSS |
| PEP2-47 | SEQ ID NO: 173<br>PEP2-47<br>EVQLLESGGGLVQPGGSLRLSCAASGFTFPMKDMGWVRQAPGKGLEWVSAISGSGGSTYYADSVKGRFTISRDNSKNTLYLQMNSLRAED<br>TAVYYCAEPSHFDRP-FDYWGQGTLVTVSS |
| PEP2-2-1 | SEQ ID NO: 174<br>PEP2-2-1<br>EVQLLESGGGLVQPGGSLRLSCAASGFTFRNHDMGWVRQAPGKGLEWVSATSGSGGSTYYANSVKGRFTISRDNSKNTLYLQMNSLRAED<br>TAVYYCAEPKPMDTE-FDYRSPGTLVTVSS |
| PEP2-2-1-1 | SEQ ID NO: 175<br>PEP2-2-1-1<br>EVQLLESGGGLVQPGGSLRLSCAASGFTFRNHDMGWVRQAPGKGLEWVSAISGSGGSTYYADSVKGRFTISRDNSKNTLYLQMNSLRAED<br>TAVYYCAEPKPMDTE-FDYRSPGTLVTVSS |

TABLE 3-continued

Antigen binding sites

| Clone | Antigen binding site sequence |
|---|---|
| PEP2-2-1-2 | SEQ ID NO: 176<br>PEP2-2-1-2<br>EVQLLESGGGLVQPGGSLRLSCAASGFTFRNHDMGWVRQAPGKGLEWVSATSGSGGSTYYADSVKGRFTISRDNSKNTLYLQMNSLRAED<br>TAVYYCAEPKPMDTE-FDYRSQGTLVTVSS |
| PEP2-2-11 | SEQ ID NO: 177<br>PEP2-2-11<br>EVQLLESGGGLVQPGGSLRLSCAASGFTFRNHDMGWVRQAPGKGLEWVSATSGSGGSTYYANSVKGRFTISRDNSKNTLYLQMNSLRAED<br>TAVYYCAEPKPMDTE-FDYPSPGTQVTVSS |
| PEP2-2-12 | SEQ ID NO: 178<br>PEP2-2-12<br>EVQLLESGGGLVQPGGSLRLSCAASGFTFRNHDMGWVRQAPGKGLEWVSATSGSGGSTYYANSVKGRFTISRDNSKNTLYLQMNSLRAED<br>TAVYYCAEPKPMDTE-FDYPSPGTLVTVSS |
| PEP2-2-2 | SEQ ID NO: 179<br>PEP2-2-2<br>EVQLLESGGGLVQPGGSLRLSCAASGFTFRNHDMGWVRQAPGKGLEWVSATSGSGGSTYYADSVKGRFTISRDNSKNTLYLQMNSLRAED<br>TAVYYCAEPKPMDTE-FDYRSQGTLVTVSS |
| PEP2-2-4 | SEQ ID NO: 180<br>PEP2-2-4<br>EVQLLESGGGLVQPGGSLRLTCAASGFSFRNHDMGWVRQAPGKGLEWVSATSGSGGSTYYADSVKGRFTISRDNSKNTLYLQMNSLRAED<br>TAVYYCAEPKPMDTE-FDYRSPGTLVTVSS |
| PEP2-2-5 | SEQ ID NO: 181<br>PEP2-2-5<br>EVQLLESGGGLVQPGGSLRLSCAASGFTFRNHDMGWVRQAPGKGLEWVSAISGSGGSTYYADSVKGRFTISRDDSKNTLYLQMNSLRAED<br>TAVYYCAEPKPMDTE-FDYRSPGTLVTVSS |
| PEP2-2-8 | SEQ ID NO: 182<br>PEP2-2-8<br>EVQLLESGGGLVQPGGSLRLSCAASGFTFRNHDMGWVRQAPGKGLEWVSAISGSGGSTYYADSVKGRFTISRDNSKNTLYLQMNSLRAED<br>TAVYYCAEPKPMDTE-FDYFSQGTLVTVSS |
| PEP2-2-9 | SEQ ID NO: 183<br>PEP2-2-9<br>EVQLLESGGGLVQPGGSLRLSCAASGFTFRNHDMGWVRQAPGKGLEWVSAISGSGGSTYYADSVKGRFTISRDNSKNTLYLQMNSLRAED<br>TAVYYCAEPKPMDTE-FDYRFQGTLVTVSS |
| PEP2-2-3 | SEQ ID NO: 184<br>PEP2-2-3<br>EVQLLESGGGLVQPGGSLRLSCAASGFTFRNHDMGWVRQAPGKGLEWVSAISGSGGSTYYADSVKGRFTISRDNSKNTLYLQMNSLRAED<br>TAVYYCAEPKPMDTE-FDYWSPGTLVTVSS |
| PEP2-2-10 | SEQ ID NO: 185<br>PEP2-2-10<br>EVQLLESGGGLVQPGGSLRLSCAASGFTFRNHDMGWVRQAPGKGLEWVSAISGSGGSTYYADSVKGRFTISRDNSKNTLYLQMNSLRAED<br>TAVYYCAEPKPMDTE-FDYRFPGTLVTVSS |
| PEP2-2-101 | SEQ ID NO: 186<br>PEP2-2-101<br>EVQLLESGGGLVQPGGSLRLSCAASGFTFRNHDMGWVRQAPGKGLEWVSAISGSGGSTYYADSVKGRFTISRDNSKNTLYLQMNSLRAED<br>TAVYYCAEPKPMDTE-FDYRGPGTLVTVSS |
| PEP2-2-102 | SEQ ID NO: 187<br>PEP2-2-102<br>EVQLLESGGGLVQPGGSLRLSCAASGFTFRNHDMGWVRQAPGKGLEWVSAISGSGGSTYYADSVKGRFTISRDNSKNTLYLQMNSLRAED<br>TAVYYCAEPKPMDTE-FDYCGPGTLVTVSS |
| PEP2-472-1 | SEQ ID NO: 188<br>PEP2-472-1<br>EVQLLESGGGLVQPGGSLRLSCAASGYTFPMKDMGWVRQAPGKGLEWVSAISGSGGGTYYADSVKGRFTISRDNSKNTLYLQMNSLRAED<br>TAVYYCAEPKPMDTE-FDYRSQGTLVTVSS |
| PEP2-472-11 | SEQ ID NO: 189<br>P2-472-11<br>EVQLLESGGGLVQPGGSLRLSCAASGYTFPMKDMGWVRQAPGKGLEWVSAISGSGGGTYYADSVKGRFTISRDNSKNTLYLQMNSLRAED<br>TAVYYCAEPKPMDTE-FDYRSCGTLVTVSS |
| PEP2-472-12 | SEQ ID NO: 190<br>P2-472-12<br>EVQLLESGGGLVQPGGSLRLSCAASGYTFPMKDMGWVRQAPGKGLEWVSAISGSGGGTYYADSVKGRFTISRDNSKNTLYLQMNSLRAED<br>TAVYYCAEPKPMDTE-FDYRSPGTLVTVSS |

TABLE 3-continued

Antigen binding sites

| Clone | Antigen binding site sequence |
|---|---|
| PEP2-<br>472-121 | SEQ ID NO: 191<br>P2-472-121<br>EVQLLESGGGLVQPGGSLRLSCAASGYTFPMKDMGWVRQAPGKGLEWVSAISGSGGGTYYADSVKGRFTISRDNSKNTLYLQMNSLRAED<br>TAVYYCAEPKPMDTE-FDYPSPGTLVTVSS |
| PEP2-<br>247-1 | SEQ ID NO: 192<br>PEP2-247-1<br>EVQLLESGGGLVQPGGSLRLSCAASGFTFRNHDMGWVRQAPGKGLEWVSAISGSGGGTYYADSVKGRFTISRDNSKNTLYLQMNSLRAED<br>TAVYYCAEPSHFDRP-FDYRSQGTLVTVSS |
| PEP2-<br>247-2 | SEQ ID NO: 193<br>PEP2-247-2<br>EVQLLESGGGLVQPGGSLRLSCAASGFTFRNHDMGWVRQAPGKGLEWVSAISGSGGSTYYANSVKGRFTISRDNSKNTLYLQMNSLRAED<br>TAVYYCAEPSHF DRP-FDYRSQGTLVTVSS |
| PEP2-<br>42-1 | SEQ ID NO: 194<br>PEP2-42-1<br>EVQMLESGGGLVQPGGSLRLSCAASGFTFDNVEMSWVRQAPGKGLEWVSSIGTKGEYTYYADSVKGRFTISRDNSKNTLYLQMNSMRAED<br>TAVYYCAQTVNVPEPAFAYWGQGTLVTVLS |
| PEP2-<br>42-2 | SEQ ID NO: 195<br>PEP2-42-2<br>EVQMLESGGGLVQPGESLRLSCAASGFTFDNVEMSWVRQAPGKGLEWVSSIGSKGEYTYYADSVKGRFTISRDNSKNTLYLQMNSPRAED<br>TAVYYCAQTVNVPEPAFAYWGQGTLVTVSS |
| PEP2-<br>47-1 | SEQ ID NO: 196<br>PEP2-47-1<br>EVQLLESGGGLVQPGGSLRLSCAASGYTFPMKDMGWVRQAPGKGLEWVSAISGSGGGTYYADSVKGRFTISRDNSKNTLYLQMNSLRAED<br>TAVYYCAEPSHFDRP-FDYRSQGTLVTVSS |
| PEP2-<br>47-2 | SEQ ID NO: 197<br>PEP2-47-2<br>EVQLLESGGGLVQPGGSLRLSCAASGYTFPMKDMGWVRQAPGKGLEWVSAISGSGGGTYYANSVKGRFTISRDNSKNTLYLQMNSLRAED<br>TAVYYCAEPSHFDRP-FDYRSQGTLVTVSS |

In one embodiment there is provided an antigen binding site for binding to a $P2X_7$ receptor, the antigen binding site being defined by general formula 11:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has a sequence selected from the group consisting of:

(R/P/D)(N/M)(H/K/V)(D/E)M(G/S)

In one embodiment there is provided an antigen binding site for binding to a $P2X_7$ receptor, the antigen binding site being defined by general formula 12:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR2 has a sequence selected from the group consisting of:

(A/S)I(S/G)(G/S/T)(S/K)G(G/E)(S/G/D/Y)TYYA(D/N)
SVKG.

In one embodiment there is provided an antigen binding site for binding to a $P2X_7$ receptor, the antigen binding site being defined by general formula 13:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has a sequence selected from the group consisting of:

(E/Q)(P/T)(K/S/V)(P/H/N)(M/F/V)(D/P)(T/R/E)(E/P)
$(A^1)$F(A/D)Y wherein $A^1$ refers to no amino acid between (E/P) and F or alanine.

In one embodiment there is provided an antigen binding site for binding to a $P2X_7$ receptor, the antigen binding site being defined by general formula 14:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;

wherein:

CDR3 has a sequence:
(E/Q)(P/T)(K/S/V)(P/H/N)(M/F/V)(D/P)(T/R/E)(E/P)

(A¹)F(A/D)Y
and

FR4 has a sequence:
(W/R/P/G/C)(G/S/F)(Q/C/P)GT(L/Q)VTV(S/L)(S/E).

In one embodiment there is provided an antigen binding site for binding to a P2X₇ receptor, the antigen binding site being defined by general formula 15:

FR1-CDR1-FR2-CDR2-FR3-CDR3-FR4 wherein:

FR1, FR2, FR3 and FR4 are each framework regions;

CDR1, CDR2 and CDR3 are each complementarity determining regions;

wherein:

CDR1 has a sequence:
(R/P/D)(N/M)(H/K/V)(D/E)M(G/S);

CDR2 has a sequence:
(A/S)I(S/G)(G/S/T)(S/K)G(G/E)(S/G/D/Y)TYYA(D/N)
SVKG;

CDR3 has a sequence:
(E/Q)(P/T)(K/S/V)(P/H/N)(M/F/V)(D/P)(T/R/E)(E/P)

(A¹)F(A/D)Y;

wherein A¹ refers to no amino acid between (E/P) and F or alanine.
and

FR4 has a sequence:
(W/R/P/G/C)(G/S/F)(Q/C/P)GT(L/Q)VTV(S/L)(S/E).

In one embodiment there is provided an antigen binding site for binding to a P2X₇ receptor, the antigen binding site being defined by general formula 16:

FR1-CDR1-FR2-CDR2-FR3-CDR3-FR4 wherein:

FR1, FR2, FR3 and FR4 are each framework regions;

CDR1, CDR2 and CDR3 are each complementarity determining regions;

wherein:

CDR1 has a sequence:
(R/P/D)(N/M)(H/K/V)(D/E)M(G/S);

CDR2 has a sequence:
(A/S)I(S/G)(G/S/T)(S/K)G(G/E)(S/G/D/Y)TYYA(D/N)
SVKG;

CDR3 has a sequence:
(E/Q)(P/T)(K/S/V)(P/H/N)(M/F/V)(D/P)(T/R/E)(E/P)

(A¹)F(A/D)Y, wherein A¹ refers to no amino acid between (E/P) and F or alanine;

FR1 has a sequence:
EVQLLE(S/P)GGGLVQPGGSLRLSCAASG(Y/F/V)(R/T/N)
(I/F/V);

FR2 has a sequence:
WVRQAPGKGLEWVS;

FR3 has a sequence:
RFTISRDNSKNTLYLQMNS(L/M)RAEDTAVYYCA;

FR4 has a sequence:
(W/R/P/G/C)(G/S/F)(Q/C/P)GT(L/Q)VTV(S/L)(S/E).

In certain embodiments the antigen binding site is one having at least 75%, preferably 80%, more preferably 85%, more preferably 90%, more preferably 95%, more preferably 98% or 99% identity to an antigen binding site shown in Table 3.

In certain embodiments the CDR is one having at least 75%, preferably 80%, more preferably 85%, more preferably 90%, more preferably 95%, more preferably 98% or 99% identity to a CDR shown in Table 1.

Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis., USA 53711) as disclosed in Needleman, S. B. and Wunsch, C. D., (1970), Journal of Molecular Biology, 48, 443-453, which is hereby incorporated by reference in its entirety. GAP is used with the following settings for polypeptide sequence comparison: GAP creation penalty of 3.0 and GAP extension penalty of 0.1.

Sequence identity of polynucleotide molecules is determined by similar methods using GAP with the following settings for DNA sequence comparison: GAP creation penalty of 5.0 and GAP extension penalty of 0.3.

In other embodiments there is provided an antigen binding site or CDR and/or FR having a sequence as described above and including one or more mutations for increasing the affinity of said site for binding to an anti-P2X₇ receptor. The mutation may result in a substitution, insertion or deletion of a residue in one or more of CDR1, CDR2 or CDR3, or one or more or FR1, FR2, FR3 or FR4.

Marks et al. (1992) BioTechnology 10:779, which describes affinity maturation by VH and VL domain shuffling; Barbas et al. (1994) Proc Nat. Acad. Sci. USA 91:3809; Schier et al. (1995) Gene 169:147-155; Yelton et al. (1995) J. Immunol. 155:1994; Jackson et al (1995), J. Immunol. 154(7):3310; and Hawkins et al, (1992) J. Mol. Biol. 226:889, which describe random mutagenesis of hypervariable region and/or framework residues, are examples of procedures known in the art for affinity maturation of antigen binding sites. In certain embodiments, a nucleic acid encoding one or more of the sequences shown in Table 1 or Table 3 is mutagenized to create a diverse library of sequences. The library is then screened against a target including an epitope of a non functional P2X₇ receptor. An exemplary method is shown in the Examples herein.

In another embodiment there is provided an antigen binding site as described above wherein an amino acid sequence forming one or more of FR1, CDR1, FR2, CDR2, FR3, CDR3 and FR4 is derived from a human sequence or in the form of a human sequence.

The antigen binding site may be presented in a humanized form including non-human (e.g., murine) and human immunoglobulin sequences. Typically all but the CDR sequences of the antigen binding site are from a non-human species such as mouse, rat or rabbit. In some instances, framework residues of the antigen binding site may also be non human. Where the antigen binding site is provided in the form of a whole antibody, typically at least a portion of an immunoglobulin constant region (Fc) is human, thereby allowing various human effector functions.

Methods for humanizing non-human antigen binding sites are well known in the art, examples of suitable processes including those in Jones et al., (1986) Nature, 321:522; Riechmann et al., (1988) Nature, 332:323; Verhoeyen et al., (1988) Science, 239:1534.

Phage display methods described herein using antibody libraries derived from human immunoglobulin sequences are useful for generating human antigen binding sites and human antibodies.

Also, transgenic mammals that are incapable of expressing functional endogenous immunoglobulins, but which can express human immunoglobulin genes can be used. These mice may be generated by random or targeted insertion of the human heavy and light chain immunoglobulin genes into embryonic stem cells. The host heavy and light chain immunoglobulin genes may be rendered non-functional by the insertion or by some other recombination event, for example by homozygous deletion of the host JH region. The transfected embryonic stem cells are expanded and microinjected into blastocysts to produce chimeric mice that are then bred to produce homozygous offspring that express human antigen binding sites. After immunization with a $P2X_7$ epitope, human monoclonal antibodies can be obtained. One benefit of transgenic animal systems is that it is possible to produce therapeutically useful isotypes because the human immunoglobulin transgenes rearrange during B-cell differentiation and subsequently undergo class switching and somatic mutation in the transgenic mice.

Variable domains including CDRs and FRs of the invention may have been made less immunogenic by replacing surface-exposed residues so as to make the antibody appear as self to the immune system. Padlan, E. A., 1991, Mol. Immunol. 28, 489 provides an exemplary method. Generally, affinity is preserved because the internal packing of amino acid residues in the vicinity of the antigen binding site remains unchanged and generally CDR residues or adjacent residues which influence binding characteristics are not to be substituted in these processes.

In another embodiment there is provided an anti $P2X_7$ receptor immunoglobulin variable domain, antibody, Fab, dab or scFv including an antigen binding site as described above. In certain embodiments the antigen binding site has a sequence as shown in Table 3.

Lower molecular weight antibody fragments, as compared with whole antibodies may have improved access to solid tumors and more rapid clearance which may be particularly useful in therapeutic and in vivo diagnostic applications.

Various techniques have been developed for the production of antibody fragments including proteolytic digestion of intact antibodies and recombinant expression in host cells. With regard to the latter, as described below, Fab, Fv and scFv antibody fragments can all be expressed in and secreted from E. coli, antibody fragments can be isolated from the antibody phage libraries and Fab'-SH fragments can be directly recovered from E. coli and chemically coupled to form F(ab')2 fragments. In another approach, F(ab')2 fragments are isolated directly from recombinant host cell culture.

In certain embodiments, the antigen binding site is provided in the form of a single chain Fv fragment (scFv). Fv and scFv are suitable for reduced nonspecific binding during in vivo use as they have intact combining sites that are devoid of constant regions. Fusion proteins including scFv may be constructed to yield fusion of an effector protein at either the amino or the carboxy terminus of an scFv.

In another embodiment there is provided a diabody or triabody or other multispecific antibody including an antigen binding site as described above. Multispecific antibodies may be assembled using polypeptide domains that allow for multimerization. Examples include the CH2 and CH3 regions of the Fc and the CH1 and Ckappa/lambda regions. Other naturally occurring protein multimerization domains may be used including leucine zipper domain (bZIP), helix-loop-helix motif, Src homology domain (SH2, SH3), an EF hand, a phosphotyrosine binding (PTB) domain, or other domains known in the art.

In another embodiment there is provided a fusion domain or heterologous protein including an antigen binding site, immunoglobulin variable domain, antibody, Fab, dab, scFv, diabody or triabody as described above.

A heterologous polypeptide may be recombinantly fused or chemically conjugated to an N- or C-terminus of an antigen binding site or molecule containing same of the invention.

The heterologous polypeptide to which the antibody or antigen binding site is fused may be useful to target to the $P2X_7$ receptor expressing cells, or useful to some other function such as purification, or increasing the in vivo half life of the polypeptides, or for use in immunoassays using methods known in the art.

In preferred embodiments, a marker amino acid sequence such as a hexa-histidine peptide is useful for convenient purification of the fusion protein. Others include, but are not limited to, the "HA" tag, which corresponds to an epitope derived from the influenza hemagglutinin protein and the "flag" tag.

Further, the antigen binding site, immunoglobulin variable domain, antibody, Fab, dab, scFv, diabody or triabody of the invention may be modified by glycosylation, acetylation, pegylation, phosphorylation, amidation, derivatization by known protecting/blocking groups, proteolytic cleavage, linkage to a cellular ligand or other protein, etc.

Antigen binding sites of the invention can be composed of amino acids joined to each other by peptide bonds or modified peptide bonds, i.e., peptide isosteres, and may contain amino acids other than the 20 gene-encoded amino acids. Antigen binding sites of the invention may be modified by natural processes, such as posttranslational processing, or by chemical modification techniques which are well known in the art. Such modifications are well described in basic texts, as well as in research literature. Modifications can occur anywhere in the antigen binding site, including the peptide backbone, the amino acid side-chains and the amino or carboxyl termini, or on moieties such as carbohydrates. It will be appreciated that the same type of modification may be present in the same or varying degrees at several sites in a given antigen binding site. Also, a given antigen binding site may contain many types of modifications. An antigen binding site may be branched, for example, as a result of ubiquitination, and they may be cyclic, with or without branching. Cyclic, branched, and branched cyclic antigen binding sites may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

In another embodiment there is provided a conjugate in the form of an antigen binding site, immunoglobulin variable domain, antibody, Fab, dab, scFsv, diabody, triabody or fusion protein as described above conjugated to a cytotoxic agent such as a chemo therapeutic agent, a drug, a growth inhibitory agent, a toxin (e.g., an enzymatically active toxin of bacterial, fungal, plant, or animal origin, or fragments thereof), or a label such as a radioactive isotope (i.e., a radio conjugate). In another aspect, the invention further provides methods of using the immunoconjugates. In one aspect, an immunoconjugate comprises any of the above variable domains covalently attached to a cytotoxic agent or a detectable agent.

In another embodiment there is provided an antibody for binding to an antigen binding site of an immunoglobulin variable domain, antibody, Fab, dab, scFv, diabody, triabody, fusion protein or conjugate as described above.

In another embodiment there is provided a nucleic acid encoding an antigen binding site, immunoglobulin variable domain, antibody, Fab, dab, scFv, diabody, triabody, fusion protein or conjugate as described above.

A polynucleotide encoding an CDR or FR according to any one of the general formulae described above, or an antigen binding site comprised of same, may be generated from a nucleic acid from any source, for example by chemical synthesis or isolation from a cDNA or genomic library. For example a cDNA library may be generated from an antibody producing cell such as a B cell, plasma cell or hybridoma cell and the relevant nucleic acid isolated by PCR amplification using oligonucleotides directed to the particular clone of interest. Isolated nucleic acids may then be cloned into vectors using any method known in the art. The relevant nucleotide sequence may then be mutagenized using methods known in the art e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N. Y. and Ausubel et al., eds., 1998, Current Protocols in Molecular Biology, John Wiley & Sons, NY), to generate antigen binding sites having a different amino acid sequence, for example to create amino acid substitutions, deletions, and/or insertions.

In another embodiment there is provided a vector including a nucleic acid described above. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The antigen binding site may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the antigen binding site-encoding DNA that is inserted into the vector. The signal sequence may be a prokaryotic signal sequence selected, for example, from the group of the alkaline phosphatase, penicillinase, Ipp, or heat-stable enterotoxin II leaders. For yeast secretion the signal sequence may be, e.g., the yeast invertase leader, alpha factor leader, or acid phosphatase leader or the *C. albicans* glucoamylase leader. In mammalian cell expression, mammalian signal sequences may be used to direct secretion of the protein, such as signal sequences from secreted polypeptides of the same or related species, as well as viral secretory leaders.

Polynucleotide sequences encoding polypeptide components of the antigen binding site of the invention can be obtained using standard recombinant techniques as described above. Polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides.

In general, plasmid vectors containing replicon and control sequences which are derived from species compatible with the host cell are used in connection with these hosts. Both expression and cloning vectors contain a nucleic acid sequence that enables the vector to replicate in one or more selected host cells, as well as marking sequences which are capable of providing phenotypic selection in transformed cells.

Such sequences are well known for a variety of bacteria, yeast, and viruses. The origin of replication from the plasmid pBR322, which contains genes encoding ampicillin (Amp) and tetracycline (Tet) resistance and thus provides easy means for identifying transformed cells, is suitable for most Gram-negative bacteria, the 2 μm plasmid origin is suitable for yeast, and various viral origins (SV40, polyoma, adenovirus, VSV or BPV) are useful for cloning vectors in mammalian cells. pBR322, its derivatives, or other microbial plasmids or bacteriophage may also contain, or be modified to contain, promoters which can be used by the microbial organism for expression of endogenous proteins.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as *E. coli* LE392.

The expression vector of the invention may comprise two or more promoter-cistron (a cistron being segment of DNA that contains all the information for production of single polypeptide) pairs. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters recognized by a variety of potential host cells are well known. Promoters suitable for use with prokaryotic hosts include the PhoA promoter, the β-galactamase and lactose promoter systems, alkaline phosphatase, a tryptophan (trp) promoter system and hybrid promoters such as the tac or the trc promoter. Promoters for use in bacterial systems also will contain a Shine-Dalgarno (S.D.) sequence operably linked to the DNA encoding an antigen binding site of the invention. However, other promoters that are functional in bacteria (such as other known bacterial or phage promoters) are suitable as well. Their nucleotide sequences have been published, thereby enabling a skilled person operably to ligate them to cistrons encoding the target light and heavy chains using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB⁻ strains) provide cytoplasm conditions that are favourable for disulfide bond formation, thereby permitting proper folding and assembly of expressed protein subunits.

The present invention provides an expression system in which the quantitative ratio of expressed polypeptide components can be modulated in order to maximize the yield of secreted and properly assembled antigen binding sites of the invention. Such modulation is accomplished at least in part by simultaneously modulating translational strengths for the polypeptide components.

In terms of expression in eukaryotic host cells, the vector components generally include, but are not limited to, one or more of the following: a signal sequence, an origin of replication, one or more marker genes, an enhancer element, a promoter, and a transcription termination sequence.

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed {i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

Generally, an origin of replication component is not needed for mammalian expression vectors. For example, the SV40 origin may typically be used only because it contains the early promoter.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

An example of suitable selectable markers for mammalian cells are those that enable the identification of cells competent to take up the antigen binding site-encoding nucleic acid, such as DHFR or thymidine kinase, metallothionein-I and -II, preferably primate metallothionein genes, adenosine deaminase, ornithine decarboxylase, etc. An appropriate host cell when wild-type DHFR is employed is the CHO cell line deficient in DHFR activity (e.g., ATCC CRL-9096), prepared and propagated. For example, cells transformed with the DHFR selection gene are first identified by culturing all of the transformants in a culture medium that contains methotrexate (Mtx), a competitive antagonist of DHFR. Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418.

Expression and cloning vectors usually contain a promoter operably linked to the antigen binding site encoding nucleic acid sequence to direct mRNA synthesis. Promoters recognized by a variety of potential host cells are well known.

Eukaryotic genes generally have an AT-rich region located approximately 25 to 30 bases upstream from the site where transcription is initiated. Another sequence found 70 to 80 bases upstream from the start of transcription of many genes is a CNCAAT region where N may be any nucleotide.

At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes including enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization.

Antigen binding site transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the antigen binding site by higher eukaryotes may be increased by inserting an enhancer sequence into the vector. Enhancer sequences include those known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antigen binding site.

In another embodiment there is provided a cell including a vector or nucleic acid described above. The nucleic acid molecule or vector may be present in the genetically modified host cell or host either as an independent molecule outside the genome, preferably as a molecule which is capable of replication, or it may be stably integrated into the genome of the host cell or host.

The host cell of the present invention may be any prokaryotic or eukaryotic cell.

Examples of prokaryotic cells are those generally used for cloning like *E. coli* or *Bacillus subtilis*. Furthermore, eukaryotic cells comprise, for example, fungal or animal cells.

Examples for suitable fungal cells are yeast cells, preferably those of the genus *Saccharomyces* and most preferably those of the species *Saccharomyces cerevisiae*.

Examples of animal cells are, for instance, insect cells, vertebrate cells, preferably mammalian cells, such as e.g. HEK293, NSO, CHO, MDCK, U2-OS, Hela, NIH3T3, MOLT-4, Jurkat, PC-12, PC-3, IMR, NT2N, Sk-n-sh, CaSki, C33A. These host cells, e.g. CHO-cells, may provide post-translational modifications to the antibody molecules of the invention, including leader peptide removal, folding and assembly of H (heavy) and L (light) chains, glycosylation of the molecule at correct sides and secretion of the functional molecule.

Further suitable cell lines known in the art are obtainable from cell line depositories, like the American Type Culture Collection (ATCC).

In another embodiment there is provided an animal including a cell described above. In certain embodiments, animals and tissues thereof containing a transgene are useful in producing the antigen binding sites of the invention. The introduction of the nucleic acid molecules as transgenes into non-human hosts and their subsequent expression may be employed for the production of the antigen binding sites, for example, the expression of such a transgene in the milk of the transgenic animal provide for means of obtaining the antigen binding sites in quantitative amounts. Useful transgenes in this respect comprise the nucleic acid molecules of the invention, for example, coding sequences for the antigen binding sites described herein, operatively linked to promoter and/or enhancer structures from a mammary gland specific gene, like casein or beta-lactoglobulin. The animal may be non-human mammals, most preferably mice, rats, sheep, calves, dogs, monkeys or apes.

In another embodiment there is provided a pharmaceutical composition including an antigen binding site, immunoglobulin variable domain, antibody, Fab, dab, scFv, diabody, triabody, fusion protein or conjugate as described above and a pharmaceutically acceptable carrier, diluent or excipient.

Methods of preparing and administering antigen binding sites thereof to a subject in need thereof are well known to or are readily determined by those skilled in the art. The route of administration of the antigen binding site may be oral, parenteral, by inhalation or topical.

The term parenteral as used herein includes, e.g., intravenous, intraarterial, intraperitoneal, intramuscular, subcutaneous, rectal or vaginal administration.

While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions, in such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating an active compound (e.g., antigen binding site) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture will preferably have labels or package inserts indicating that the associated compositions are useful for treating a subject suffering from, or predisposed disorders.

Effective doses of the compositions of the present invention, for treatment of disorders as described herein vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

For treatment of certain disorders with an antigen binding site, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more antigen binding sites with different binding specificities are administered simultaneously, in which case the dosage of each antigen binding sites administered falls within the ranges indicated.

An antigen binding site disclosed herein can be administered on multiple occasions. Intervals between single dosages can be weekly, monthly or yearly. Intervals can also be irregular as indicated by measuring blood levels of target polypeptide or target molecule in the patient. In some methods, dosage is adjusted to achieve a plasma polypeptide concentration of 1-1000 μg/ml and in some methods 25-300 μg/ml. Alternatively, antigen binding sites can be administered as a sustained release formulation, in which case less frequent administration is required. Dosage and frequency vary depending on the half-life of the antigen binding site in the patient. The half-life of an antigen binding site can also be prolonged via fusion to a stable polypeptide or moiety, e.g., albumin or PEG. In general, humanized antibodies show the longest half-life, followed by chimeric antibodies and nonhuman antibodies. In one embodiment, the antigen binding site of the invention can be administered in unconjugated form. In another embodiment the antigen binding sites for use in the methods disclosed herein can be administered multiple times in conjugated form. In still another embodiment, the antigen binding sites of the invention can be administered in unconjugated form, then in conjugated form, or vice versa.

The dosage and frequency of administration can vary depending on whether the treatment is prophylactic or therapeutic. In prophylactic applications, compositions comprising antibodies or a cocktail thereof are administered to a patient not already in the disease state or in a pre-disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of binding molecule, e.g., antigen binding site per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease. Thereafter, the patent can be administered a prophylactic regime.

In one embodiment, a subject can be treated with a nucleic acid molecule encoding an antigen binding site (e.g., in a vector). Doses for nucleic acids encoding polypeptides range from about 10 ng to 1 g, 100 ng to 100 mg, 1 μg to 10 mg, or 30-300 μg DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment, in some methods, agents are injected directly into a particular tissue where non-functional $P2X_7$ receptor cells have accumulated, for example intracranial injection. Intramuscular injection or intravenous infusion are preferred for administration of antibody, in some methods, particular therapeutic antibodies are injected directly into the cranium, in some methods, antibodies are administered as a sustained release composition or device.

An antigen binding site of the invention can optionally be administered in combination with other agents that are effective in treating the disorder or condition in need of treatment (e.g., prophylactic or therapeutic).

In another embodiment there is provided a pharmaceutical composition including an antigen binding site, immunoglobulin variable domain, antibody, Fab, dab, scFv, diabody, triabody, fusion protein or conjugate as described above, a diluent and optionally a label.

In certain embodiments, the antigen binding sites or molecule including same are detectably labelled. Many different labels can be used including enzymes, radioisotopes, colloidal metals, fluorescent compounds, chemiluminescent compounds, and bioluminescent compounds. Fluorochromes (fluorescein, rhodamine, Texas Red, etc.), enzymes (horse radish peroxidase, β-galactosidase, alkaline phosphatase etc.), radioactive isotopes ($^{32}P$ or $^{125}I$), biotin, digoxygenin, colloidal metals, chemi- or bioluminescent compounds (dioxetanes, luminol or acridiniums) are commonly used.

Detection methods depend on the type of label used and include autoradiography, fluorescence microscopy, direct and indirect enzymatic reactions. Examples include Westernblotting, overlay-assays, RIA (Radioimmuno Assay) and IRMA (Immune Radioimmunometric Assay), EIA (Enzyme Immuno Assay), ELISA (Enzyme Linked Immuno Sorbent Assay), FIA (Fluorescent Immuno Assay), and CLIA (Chemioluminescent Immune Assay).

In another embodiment there is provided a kit or article of manufacture including an antigen binding site, immunoglobulin variable domain, antibody, Fab, dab, scFv, diabody, triabody, fusion protein, conjugate or pharmaceutical composition as described above.

In other embodiments there is provided a kit for use in a therapeutic application mentioned above, the kit including:
a container holding a therapeutic composition in the form of one or more of an antigen binding site, immunoglobulin variable domain, antibody, Fab, dab, scFv, diabody, triabody, fusion protein, conjugate or pharmaceutical composition;
a label or package insert with instructions for use.

In certain embodiments the kit may contain one or more further active principles or ingredients for treatment of a cancer or for preventing a cancer-related complication described above, or a condition or disease associated with non functional $P2X_7$ receptor expression.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic composition can be used to treat a cancer or to prevent a complication stemming from cancer.

The kit may comprise (a) a therapeutic composition; and (b) a second container with a second active principle or ingredient contained therein. The kit in this embodiment of the invention may further comprise a package insert indicating that the and other active principle can be used to treat a disorder or prevent a complication stemming from cancer. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments the therapeutic composition may be provided in the form of a device, disposable or reusable, including a receptacle for holding the therapeutic composition. In one embodiment, the device is a syringe. The device may hold 1-2 mL of the therapeutic composition. The therapeutic composition may be provided in the device in a state that is ready for use or in a state requiring mixing or addition of further components.

In another embodiment there is provided a kit or article of manufacture including an antigen binding site, immunoglobulin variable domain, antibody, Fab, dab, scFv, diabody, triabody, fusion protein, conjugate or a diagnostic composition as described above.

In other embodiments there is provided a kit for use in a diagnostic application mentioned above, the kit including:
a container holding a diagnostic composition in the form of one or more of an antigen binding site, immunoglobulin variable domain, antibody, Fab, dab, scFv, diabody, triabody, fusion protein or conjugate;
a label or package insert with instructions for use.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a diagnostic composition which is effective for detection of cancer and may have a sterile access port (for example the container may be an intravenous solution bag or a vial having a stopper pierceable by a hypodermic injection needle). The label or package insert indicates that the diagnostic composition is used for detecting the condition of choice. In one embodiment, the label or package insert includes instructions for use and indicates that the diagnostic composition can be used to detect a cancer or a disease or condition characterised by non functional $P2X_7$ receptor expression.

The kit may comprise (a) a diagnostic composition; and (b) a second container with a second diagnostic agent or second label contained therein. It may further include other materials desirable from a commercial and user standpoint, including other buffers, diluents, filters etc.

In another embodiment there is provided a method for producing an anti $P2X_7$ antigen binding site as described above including expressing a nucleic acid as described above in a cell or non human animal as described above.

The production of an antigen binding site of the invention generally requires an expression vector containing a polynucleotide that encodes the antigen binding site of the invention. A polynucleotide encoding an antigen binding site of the invention may be obtained and sub cloned into a vector for the production of an antigen binding site by recombinant DNA technology using techniques well-known in the art, including techniques described herein. Many different expression systems are contemplated including the use of mammalian cells including human cells for production and secretion of antigen binding sites. Examples of cells include 293F, CHO and the NSO cell line.

Expression vectors containing protein coding sequences and appropriate transcriptional and translational control signals can be constructed using methods known in the art. These include in vitro recombinant DNA techniques, synthetic techniques and in vivo genetic recombination. In certain embodiments there is provided a replicable vector having a nucleic acid encoding an antigen binding site operably linked to a promoter.

Cells transfected with an expression vector may be cultured by conventional techniques to produce an antigen binding site. Thus, in certain embodiments, there is provided host cells or cell transfectants containing a polynucleotide encoding an antigen binding site of the invention operably linked to a promoter. The promoter may be heterologous. A variety of host-expression vector systems may be utilized and in certain systems the transcription machinery of the vector system is particularly matched to the host cell. For example, mammalian cells such as Chinese hamster ovary cells (CHO) may be transfected with a vector including the major intermediate early gene promoter element from human cytomegalovirus. Additionally or alternatively, a host cell may be used that modulates the expression of inserted sequences, or modifies and processes the gene product as required, including various forms of post translational modification. Examples of mammalian host cells having particular post translation modification processes include CHO, VERY, BHK, Hela, COS, MDCK, 293, 3T3, W138, BT483, Hs578T, HTB2, BT2O and T47D, NSO, CRL7O3O and HsS78Bst cells.

Depending upon the use intended for the protein molecule, a number of bacterial expression vectors may be advantageously selected. In one example, vectors that cause the expression of high levels of fusion protein products that are readily purified, such as the *E. coli* expression vector pUR278 may be used where a large quantity of an antigen binding site is to be produced. The expression product may be produced in the form of a fusion protein with lacZ. Other bacterial vectors include pIN vectors and the like. pGEX vectors may also be used to express foreign polypeptides as fusion proteins with glutathione-S-transferase (GST). These fusion proteins are generally soluble and can easily be purified from lysed cells by adsorption and binding to glutathione-agarose affinity matrix followed by elution in the presence of free glutathione. A thrombin and/or factor Xa protease cleavage site may be provided in the expressed polypeptide so that the cloned target gene product can be released from the GST moiety.

*Autographa californica* nuclear polyhedrosis virus (AcNPV) may be used as a vector to express foreign genes in an insect system including *Spodoptera frugiperda* cells. The particular promoter used may depend on where the protein coding is inserted into the sequence. For example, the sequence may be cloned individually into the polyhedrin gene and placed under control of the polyhedrin promoter.

Virus based expression systems may be utilized with mammalian cells such as an adenovirus whereby the coding sequence of interest may be ligated to the adenoviral late promoter and tripartite leader sequence. In vitro or in vivo recombination may then be used to insert this chimeric gene into the adenoviral genome. Insertions into region E1 or E3 will result in a viable recombinant virus that is capable of expressing the antigen binding site in infected host cells. Specific initiation signals including the ATG initiation codon and adjacent sequences may be required for efficient translation of inserted antigen binding site coding sequences. Initiation and translational control signals and codons can be obtained from a variety of origins, both natural and synthetic. Transcription enhancer elements and transcription terminators may be used to enhance the efficiency of expression of a viral based system.

Where long-term, high-yield production of recombinant proteins is required, stable expression is preferred. Generally a selectable marker gene is used whereby following transfection, cells are grown for 1-2 days in an enriched media and then transferred to a medium containing a selective medium in which cells containing the corresponding selectable marker, for example, antibiotic resistance can be screened. The result is that cells that have stably integrated the plasmid into their chromosomes grow and form foci that in turn can be cloned and expanded into cell lines. The herpes simplex virus thymidine kinase, hypoxanthineguanine phosphoribosyltransferase and adenine phosphoribosyltransferase genes are examples of genes that can be employed in tk$^-$, hgprt$^-$ or aprT$^-$ cells, respectively thereby providing appropriate selection systems. The following genes: dhfr, which confers resistance to methotrexate; gpt, which confers resistance to mycophenolic acid; neo, which confers resistance to the aminoglycoside G-418; and hygro, which confers resistance to hygromycin are examples of genes that can be used in anti metabolite selection systems.

An antigen binding site of the invention may be purified by a recombinant expression system by known methods including ion exchange chromatography, affinity chromatography (especially affinity for the specific antigens Protein A or Protein G) and gel filtration column chromatography), centrifugation, differential solubility, or by any other standard technique for the purification of proteins. Purification may be facilitated by providing the antigen binding site in the form of a fusion protein.

Large quantities of the antigen binding sites of the invention may be produced by a scalable process starting with a pilot expression system in a research laboratory that is scaled up to an analytical scale bioreactor (typically from 5 L to about 50 L bioreactors) or production scale bioreactors (for example, but not limited to 75 L, 100 L, 150 L, 300 L, or 500 L). Desirable scalable processes include those wherein there are low to undetectable levels of aggregation as measured by HPSEC or rCGE, typically no more than 5% aggregation by weight of protein down to no more than 0.5% by weight aggregation of protein. Additionally or alternatively, undetectable levels of fragmentation measured in terms of the total peak area representing the intact antigen binding site may be desired in a scalable process so that at least 80% and as much as 99.5% or higher of the total peak area represents intact antigen binding site. In other embodiments, the scalable process of the invention produces antigen binding sites at production efficiency of about from 10 mg/L to about 300 mg/L or higher.

In another embodiment there is provided a method for the treatment of a disease or condition characterised by non functional P2X$_7$ receptor expression in an individual including the step of providing an antigen binding site, immunoglobulin variable domain, antibody, Fab, dab, scFv, diabody, triabody, fusion protein, conjugate or pharmaceutical composition as described above to an individual requiring treatment for said condition. Typically the condition is cancer, especially an epithelial cancer as described herein.

Pre-neoplastic and neoplastic diseases are particular examples to which the methods of the invention may be applied. Broad examples include breast tumors, colorectal tumors, adenocarcinomas, mesothelioma, bladder tumors, prostate tumors, germ cell tumor, hepatoma/cholongio, carcinoma, neuroendocrine tumors, pituitary neoplasm, small round cell tumor, squamous cell cancer, melanoma, atypical fibroxanthoma, seminomas, nonseminomas, stromal leydig cell tumors, Sertoli cell tumors, skin tumors, kidney tumors, testicular tumors, brain tumors, ovarian tumors, stomach tumors, oral tumors, bladder tumors, bone tumors, cervical tumors, esophageal tumors, laryngeal tumors, liver tumors, lung tumors, vaginal tumors and Wilm's tumor.

Examples of particular cancers include but are not limited to adenocarcinoma, adenoma, adenofibroma, adenolymphoma, adontoma, AIDS related. cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, ameloblastoma, angiokeratoma, angiolymphoid hyperplasia with eosinophilia, angioma sclerosing, angiomatosis, apudoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumors, breast cancer, branchioma, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-cell lymphoma, carcinoma (e.g. Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell), carcinosarcoma, cervical dysplasia, cystosarcoma phyllodies, cementoma, chordoma, choristoma, chondrosarcoma, chondroblastoma, craniopharyngioma, cholangioma, cholesteatoma, cylindroma, cystadenocarcinoma, cystadenoma, dermatofibrosarcoma-protuberans, desmoplastic-small-round-cell-tumor, ductal carcinoma, dysgerminoam, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anaemia, fibroma, fibrosarcoma, gall bladder cancer, gastric cancer, gastrointestinal cancers, gastrointestinal-carcinoid-tumor, genitourinary cancers, germ cell tumors, gestationaltrophoblastic-disease, glioma, gynaecological cancers, giant cell tumors, ganglioneuroma, glioma, glomangioma, granulosa cell tumor, gynandroblastoma, haematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, hamartoma, hemangioendothelioma, hemangioma, hemangiopericytoma, hemangiosarcoma, hemangiosarcoma, histiocytic disorders, histiocytosis malignant, histiocytoma, hepatoma, hidradenoma, hondrosarcoma, immunoproliferative small, opoma, ontraocular melanoma, islet cell cancer, Kaposi's sarcoma, kidney cancer, langerhan's cell-histiocytosis, laryngeal cancer, leiomyosarcoma, leukemia, li-fraumeni syndrome, lip cancer, liposarcoma, liver cancer, lung cancer, lymphedema, lymphoma, Hodgkin's lymphoma, non-Hodgkin's lymphoma, leigomyosarcoma, leukemia (e.g. b-cell, mixed cell, null-cell, t-cell, t-cell chronic, htlv-ii-associated, lymphangiosarcoma, lymphocytic acute, lymphocytic chronic, mast-cell and myeloid), leukosarcoma, leydig cell tumor, liposarcoma, leiomyoma, leiomyosarcoma, lymphangioma, lymphangiocytoma, lymphagioma, lymphagiomyoma, lymphangiosarcoma, male breast cancer, malignant-rhabdoid-tumor-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, malignant carcinoid syndrome carcinoid heart disease, medulloblastoma, meningioma, melanoma, mesenchymoma, mesonephroma, mesothelioma, myoblastoma, myoma, myosarcoma, myxoma, myxosarcoma, nasal cancer, nasopharyngeal cancer, nephroblastoma, neuroblastoma, neurofibromatosis, Nijmegen breakage syndrome, non-melanoma skin cancer, non-small-cell-lung-cancer-(nsclc), neurilemmoma, neuroblastoma, neuroepithelioma, neurofibromatosis, neurofibroma, neuroma, neoplasms (e.g. bone, breast, digestive system, colorectal, liver), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, osteoma, osteosarcoma, ovarian carcinoma, papilloma, paraganglioma, paraganglioma nonchromaffin, pinealoma, plasmacytoma, protooncogene, rare-cancers-and-associated-disorders, renal cell carcinoma, retinoblastoma, rhabdomyosarcoma, Rothmund-Thomson syndrome, reticuloendotheliosis, rhabdomyoma, salivary gland cancer, sarcoma, schwannoma, Sezary syndrome, skin cancer, small cell lung cancer (sclc), small intestine cancer, soft tissue sarcoma, spinal cord tumors, squamous-cell-carcinoma-(skin), stomach cancer, synovial sarcoma, sarcoma (e.g. Ewing's experimental, Kaposi's and mast-cell sarcomas), Sertoli cell tumor, synovioma, testicular cancer, thymus cancer, thyroid cancer, transitional-cell-cancer-(bladder), transitional-cell-cancer-(renal-pelvis-/-ureter), trophoblastic cancer, teratoma, theca cell tumor, thymoma, trophoblastic tumor, urethral cancer, urinary system cancer, uroplakins, uterine sarcoma, uterus cancer, vaginal cancer, vulva cancer, Waldenstrom's-macroglobulinemia and Wilms' tumor.

Other diseases and conditions include various inflammatory conditions. Examples may include a proliferative component. Particular examples include acne, angina, arthritis, aspiration pneumonia, disease, empyema, gastroenteritis, inflammation, intestinal flu, nee, necrotizing enterocolitis, pelvic inflammatory disease, pharyngitis, pid, pleurisy, raw throat, redness, rubor, sore throat, stomach flu and urinary tract infections, chronic inflammatory demyelinating polyneuropathy, chronic inflammatory demyelinating polyradiculoneuropathy, chronic inflammatory demyelinating polyneuropathy or chronic inflammatory demyelinating polyradiculoneuropathy.

In another embodiment there is provided a use of an antigen binding site, immunoglobulin variable domain, antibody, Fab, dab, scFsv, diabody, triabody, fusion protein, conjugate or pharmaceutical composition as described above in the manufacture of a medicament for the treatment of cancer.

Dosage amount, dosage frequency, routes of administration etc are described in detail above.

In another embodiment there is provided a method for the diagnosis of cancer including the step of contacting tissues or cells for which the presence or absence of cancer is to be determined with a reagent in the form of an antigen binding site, immunoglobulin variable domain, antibody, Fab, dab, scFv, diabody, triabody, fusion protein, conjugate or diagnostic composition as described above and detecting for the binding of the reagent with the tissues or cells. The method may be operated in vivo or in vitro.

For in situ diagnosis, the antigen binding site may be administered to the organism to be diagnosed by intravenous, intranasal, intraperitoneal, intracerebral, intraarterial injection or other routes such that a specific binding between an antigen binding site according to the invention with an epitopic region on the non-functional $P2X_7$ receptor may occur.

The antibody/antigen complex may conveniently be detected through a label attached to the antigen binding site or a functional fragment thereof or any other art-known method of detection.

The immunoassays used in diagnostic applications according to the invention and as described herein typically rely on labelled antigens, antibodies, or secondary reagents for detection. These proteins or reagents can be labelled with compounds generally known to those of ordinary skill in the art including enzymes, radioisotopes, and fluorescent, luminescent and chromogenic substances including, but not limited to coloured particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Antibodies useful in these assays include monoclonal antibodies, polyclonal antibodies, and affinity purified polyclonal antibodies.

Alternatively, the antigen binding site may be labelled indirectly by reaction with labelled substances that have an affinity for immunoglobulin, such as protein A or G or second antibodies. The antigen binding site may be conjugated with a second substance and detected with a labelled third substance having an affinity for the second substance conjugated to the antigen binding site. For example, the antigen binding site may be conjugated to biotin and the antigen binding site-biotin conjugate detected using labelled avidin or streptavidin. Similarly, the antigen binding site may be conjugated to a hapten and the antigen binding site-hapten conjugate detected using labelled anti-hapten antibody.

In certain embodiments, immunoassays utilize a double antibody method for detecting the presence of an analyte, wherein, the antigen binding site is labelled indirectly by reactivity with a second antibody that has been labelled with a detectable label. The second antibody is preferably one that binds to antibodies of the animal from which the antigen binding site is derived. In other words, if the antigen binding site is a mouse antibody, then the labelled, second antibody is an anti-mouse antibody. For the antigen binding site to be used in the assay described herein, this label is preferably an antibody-coated bead, particularly a magnetic bead. For the antigen binding site to be employed in the immunoassay described herein, the label is preferably a detectable molecule such as a radioactive, fluorescent or an electrochemiluminescent substance.

An alternative double antibody system, often referred to as fast format systems because they are adapted to rapid determinations of the presence of an analyte, may also be employed within the scope of the present invention. The system requires high affinity between the antigen binding site and the analyte. According to one embodiment of the present invention, the presence of the non-functional $P2X_7$ receptor is determined using a pair of antigen binding sites, each specific for $P2X_7$ receptor protein. One of said pairs of antigen binding sites is referred to herein as a "detector antigen binding site" and the other of said pair of antigen binding sites is referred to herein as a "capture antigen binding site". The antigen binding site of the present invention can be used as either a capture antigen binding site or a detector antigen binding site. The antigen binding site of the present invention can also be used as both capture and detector antigen binding site, together in a single assay. One embodiment of the present invention thus uses the double antigen binding site sandwich method for detecting non-functional $P2X_7$ receptor in a sample of biological fluid. In this method, the analyte (non-functional $P2X_7$ receptor protein) is sandwiched between the detector antigen binding site and the capture antigen binding site, the capture antigen binding site being irreversibly immobilized onto a solid support. The detector antigen binding site would contain a detectable label, in order to identify the presence of the antigen binding site-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antigen binding sites to solid phases are also well known to those of ordinary skill in the art. More recently, a number of porous material such as nylon, nitrocellulose, cellulose acetate, glass fibers and other porous polymers have been employed as solid supports.

The examples that follow are intended to illustrate but in no way limit the present invention.

EXAMPLES

Example 1—Identifying dAB Leads for Binding to Non Functional Receptors on Live Cells Objective: The experiments described here have been to find antigen binding sites that bind the E200 peptide.

Background: Antisera that bind $P2X_7$ have low affinity for $P2X_7$ as expressed on live cancer cells since the conformation of the epitope target on live cancer cells differs. To identify dAb leads for high affinity binders, we first needed to identify a suitable target, knowing that good sequence diversity of binders is required in order to widen the screening of conformational space to encompass suitable lead compounds. We selected the E200 peptide as a suitable target to identify dAb leads.

Materials and methods: The E200 peptide was made by solid phase synthesis at Chiron Mimotopes. A range of conjugates were synthesized to identify those most likely to be useful for screening purposes. These included protein conjugates BSA, DT and ovalbumin linked to the C-terminal Cys reside on E200 peptide via MCS. A fourth variant involved biotinylating the E200 peptide at the C-terminus.

Suitable lead clones were initially identified as ELISA positives in both solid phase and solution phase screens. These were made against both the unconjugated and the conjugated peptides. Additional peptides were synthesized (200-208 and 207-215) in order to differentiate more completely the binding regions of the various lead clones. Solution properties using SEC-MALLS of the lead clones were tested to ensure they were suitable for further development.

Results:

A large number of first generation leads were identified and isolated that initially bound to the E200 peptide with binding affinity in the uM $K_D$ range as measured by Biacore and then bound detectably by flow cytometry to live cancer cells expressing the non-functional $P2X_7$ receptor target on their surface. Single domain antibodies produced from Domantis phage display library screened against the peptide antigen E200 exhibited a $K_D$ of the order of 1 uM using Biacore binding analyses. Lead clones taken forward showed diversity in their binding characteristics. Three lead dAbs, PEP2-2, PEP2-4 and PEP2-5 exhibited the highest affinity when tested on live PC3 human prostate cancer cells by flow cytometry. Additional screening involved the use of standard immunohistochemistry in which normal human and cancer tissue was incubated with the chosen dAb labelled with Myc tag to which a labelled anti-Myc antibody with HRP was added. Diaminobenzoate (DAB) was added to react with any HRP remaining after due washing steps were completed. PEP2-4 and PEP2-5 bound moderately to the tumour tissue but not to normal tissue such as human prostate and skin while PEP2-2 was an example of a dAb lead that showed little effective binding to tissue in the initial screening.

Passive selection was performed using the E200, the E200-BSA conjugate, the E200, ovalbumin conjugate and the E200-DT conjugate peptides while solution screening used the biotinylated peptide then assayed using strepatavidin. Both passive and solution selections of the numerous lead dabs worked well with specific binders demonstrating good sequence diversity in the form of the single $V_H$ domains. Screening against the E200 peptide and smaller parts (200-208 and 207-215) revealed the lead dabs bound to different regions. Those with the best solution properties, being the highest monomer solubility were carried forward. Those demonstrating biphasic Biacore binding characteristics were not carried forward. All showed uM binding to the E200 peptide. Ultimately a total of five screening rounds were undertaken as shown in Example 5. An example of the results in Round 2 are shown in FIG. 1.

Figure 2:
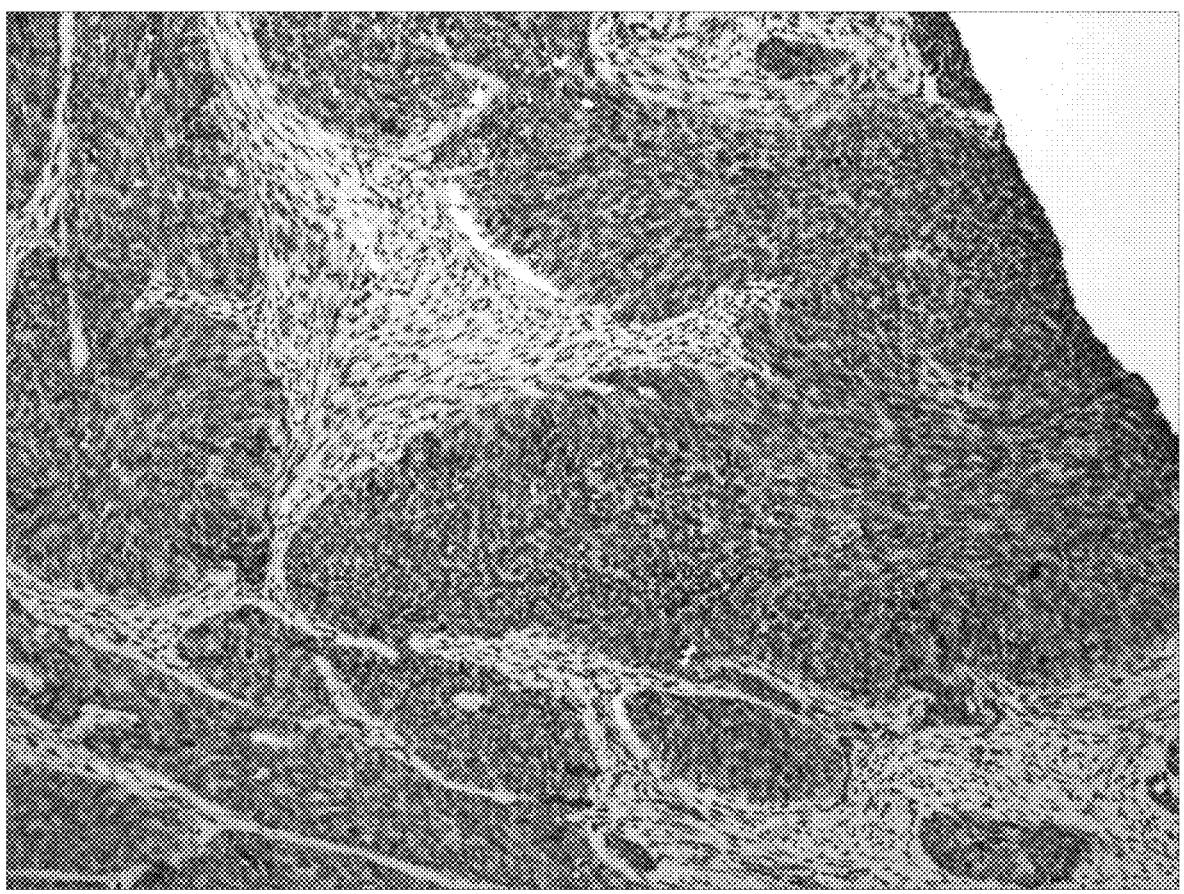
FIG. 2. 20 nM PEP2-4, no peptide, cervical cancer, objective ×10
Figure 3:
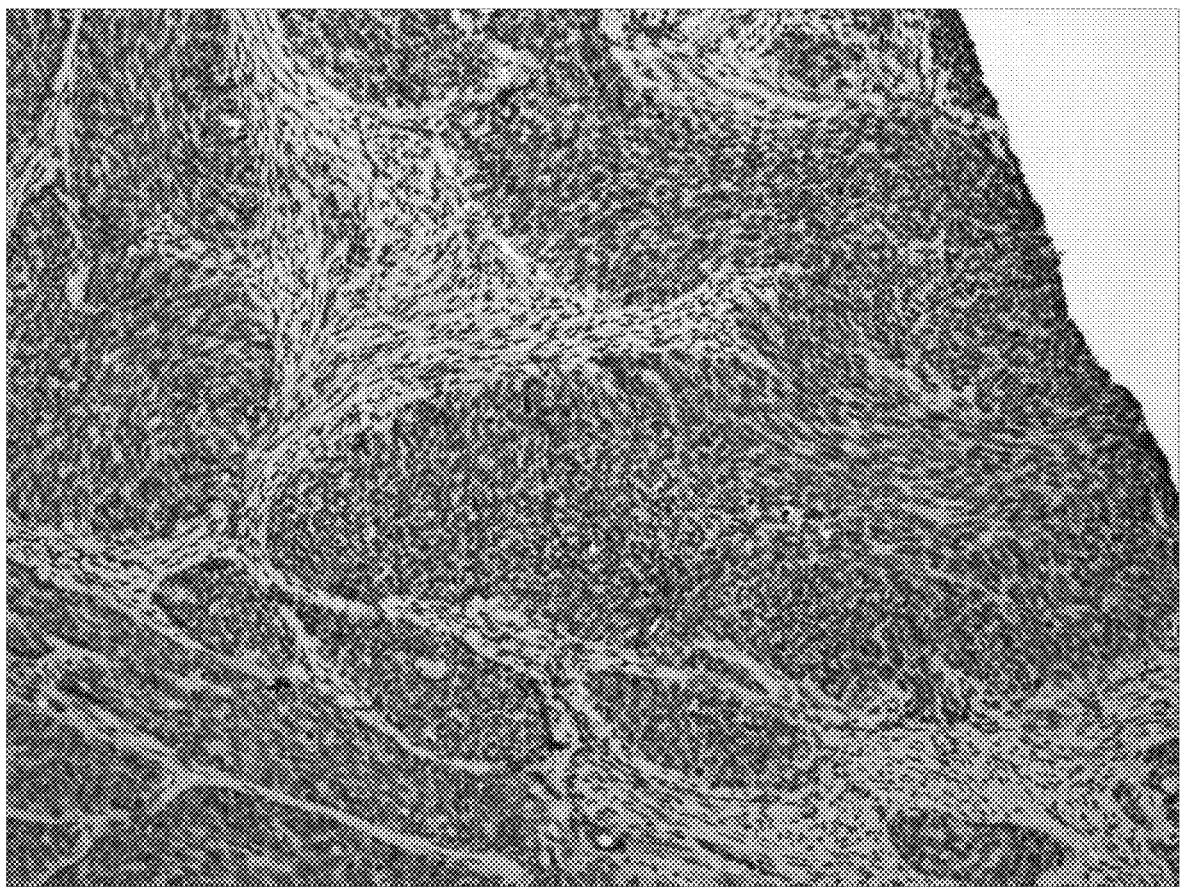
FIG. 3. 20 nM PEP2-4, 0.1 mM peptide, cervical cancer, serial section, limited binding FIG. 4. 20 nM PEP2-4, 1.0 mM peptide, cervical cancer, serial section, no binding FIG. 5. 20 nM PEP2-4, no peptide, cervical cancer, objective ×10
Figure 4:
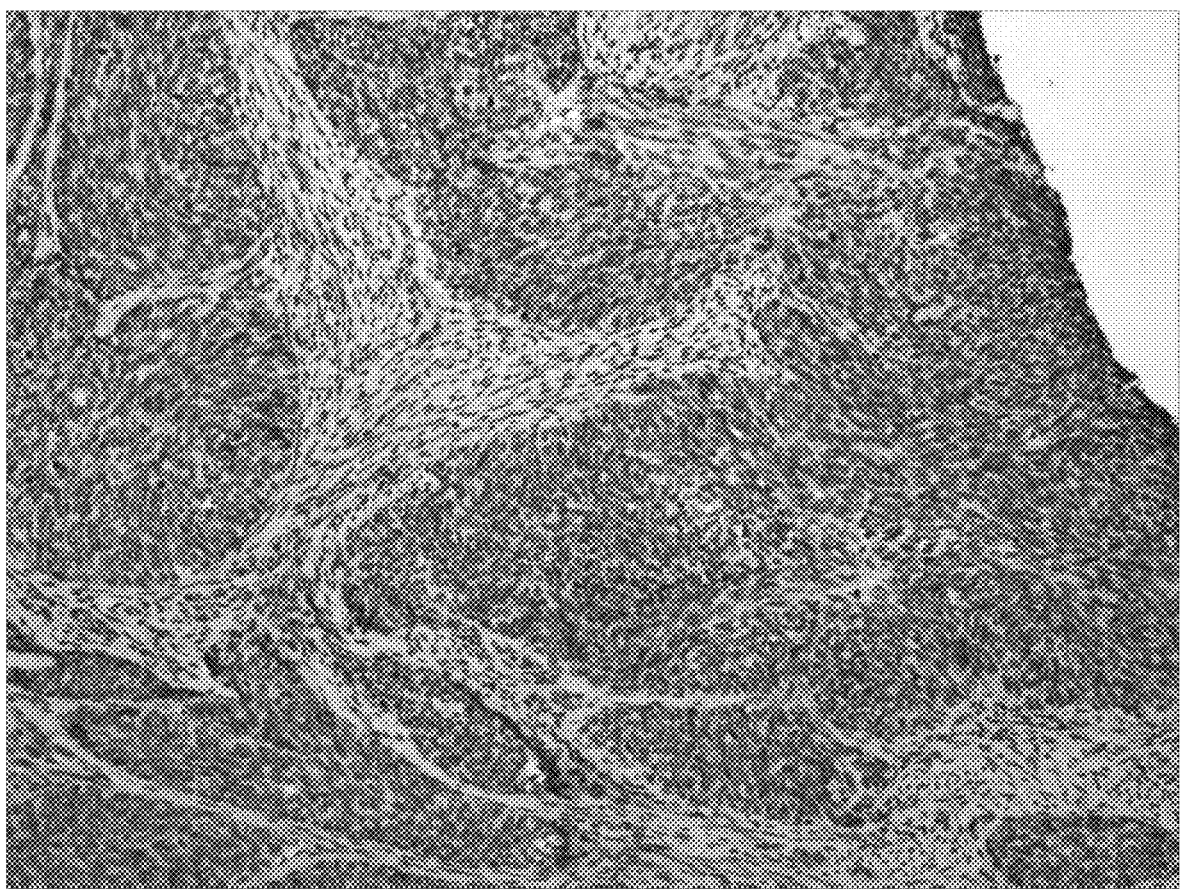

An example of dAb binding to cancer tissue follows in which human cervical cancer tissue was stained with c-Myc-labelled dAb PEP2-4 and then developed using mouse anti-Myc antibody (1:600) followed by the Biocare Medical Mach4 secondary polymer detection system and DAB. To inhibit binding, the peptide substrate was added to the primary at concentrations of 0 (FIG. 2), 25 nM (no loss of binding), 0.25 uM (no loss of binding), 10 uM (no loss of binding), 0.1 mM (FIG. 3) and 1 mM (FIG. 4).

No inhibition of binding was observed at a concentration less than 0.01 mM indicating the ideal for 50% inhibition is about 40-50 uM.

Figure 5:
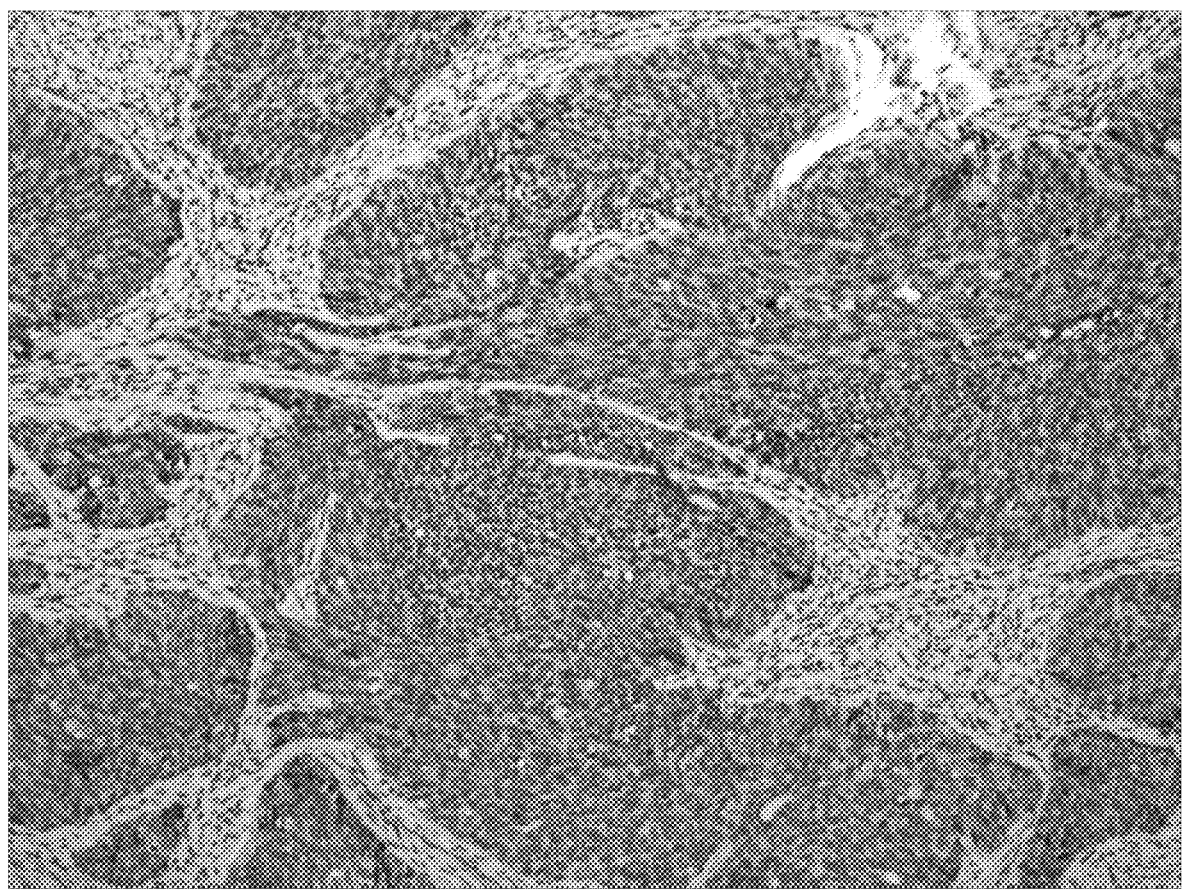
Figure 6:
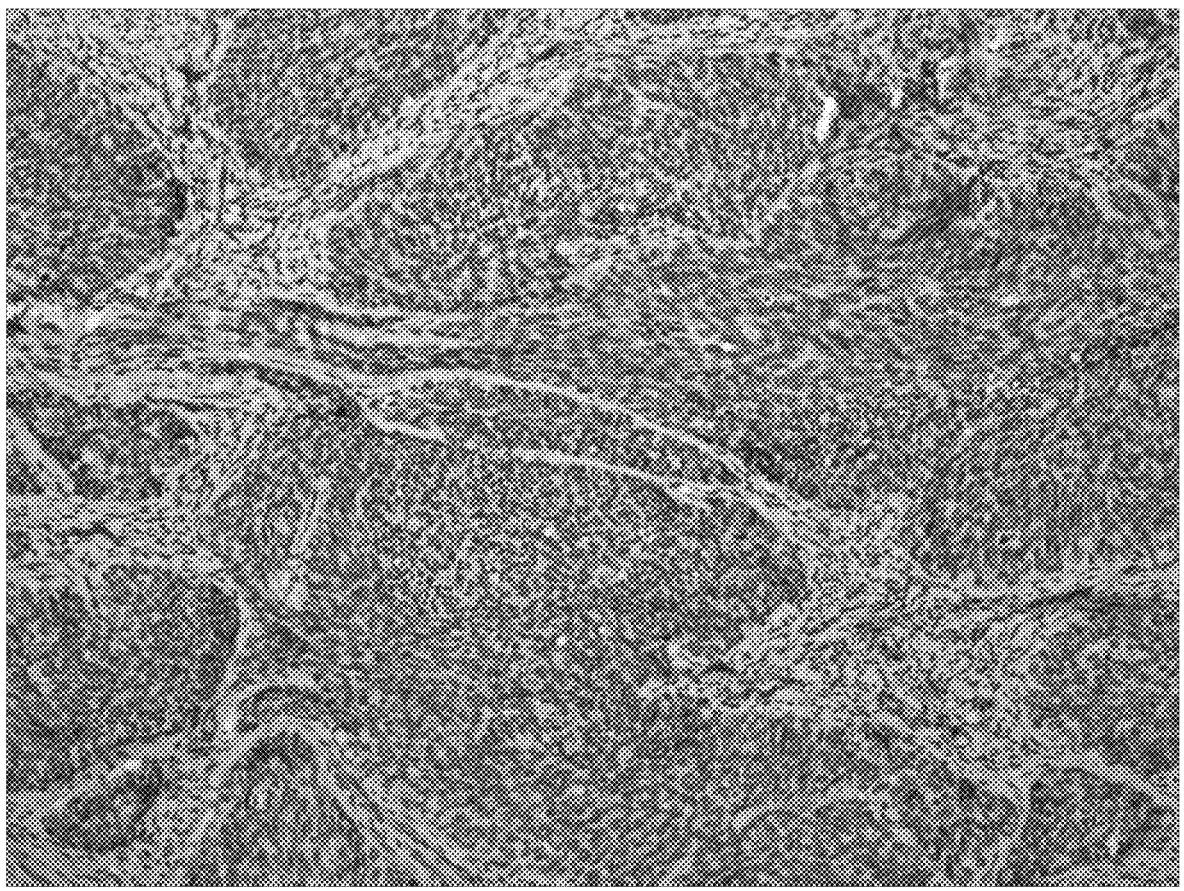
FIG. 6. 20 nM PEP2-4, 0.1 mM peptide, cervical cancer, serial section, limited binding FIG. 7. 20 nM Pep2-4, 1.0 mM peptide, cervical cancer, serial section, no binding FIG. 8. 20 nM Pep2-4, no peptide, cervical cancer FIG. 9. 20 nM Pep2-4, 10 uM peptide, cervical cancer, serial section, binding unaffected FIG. 10. 20 Nm PEP2-4 Melanoma, objective ×20
Figure 7:
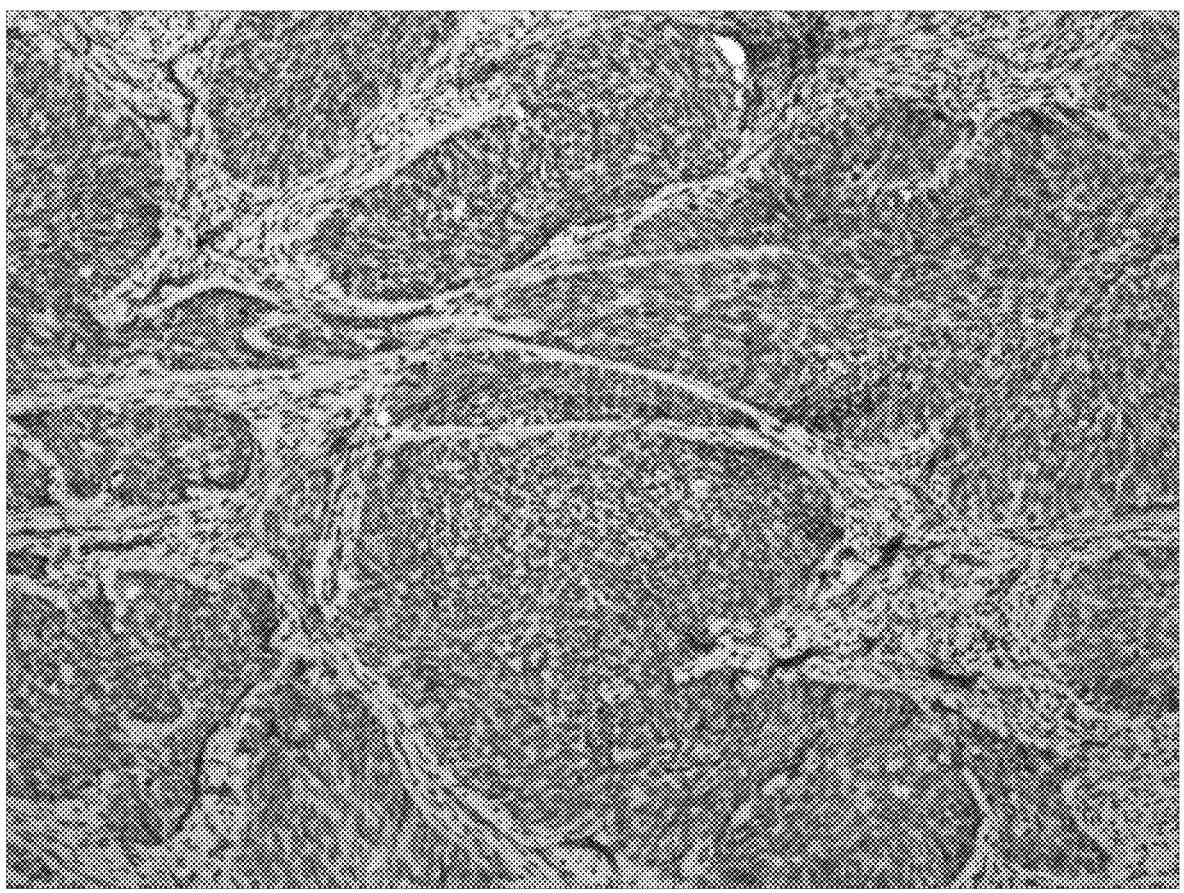

A second set of serial sections is shown in FIGS. 5-7 from different tissue sections, magnification also 10×.

Figure 8:
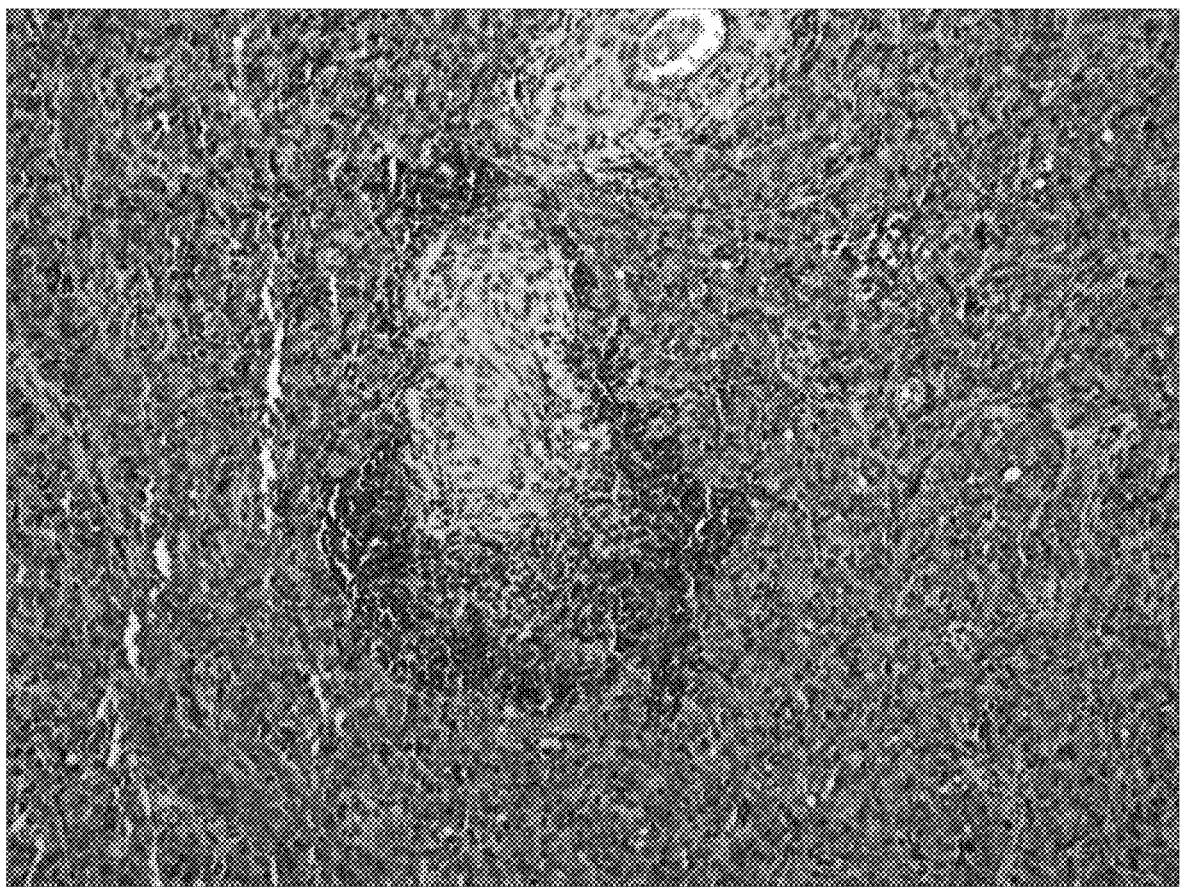
Figure 9:
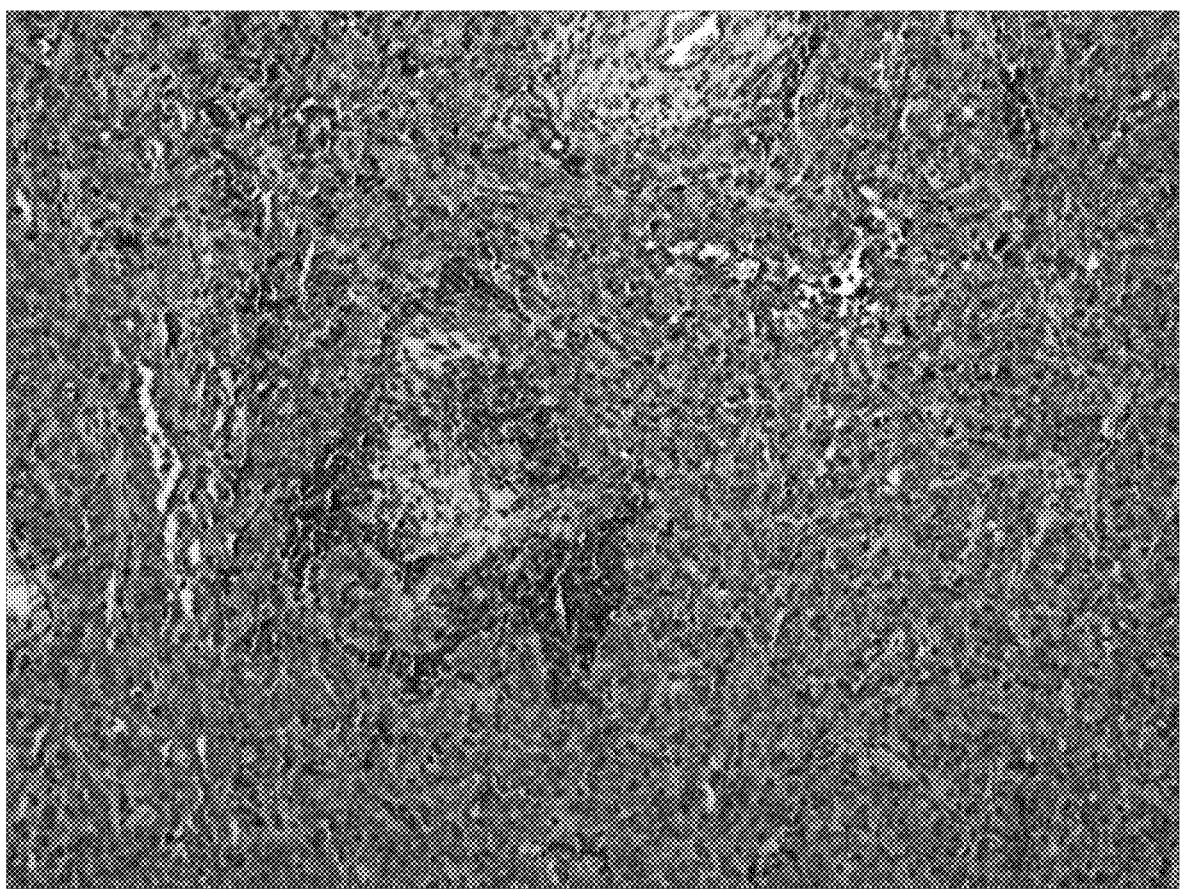

The difference between 0 and 10 uM added competing peptide in contrast was minimal as shown in FIG. 8 (no peptide) and 9 (10 uM peptide).

There is clear inhibition at 100 uM with no inhibition at 10 uM indicating that the binding at 50% inhibition appears to be about 40-50 uM in this system.

Figure 10:
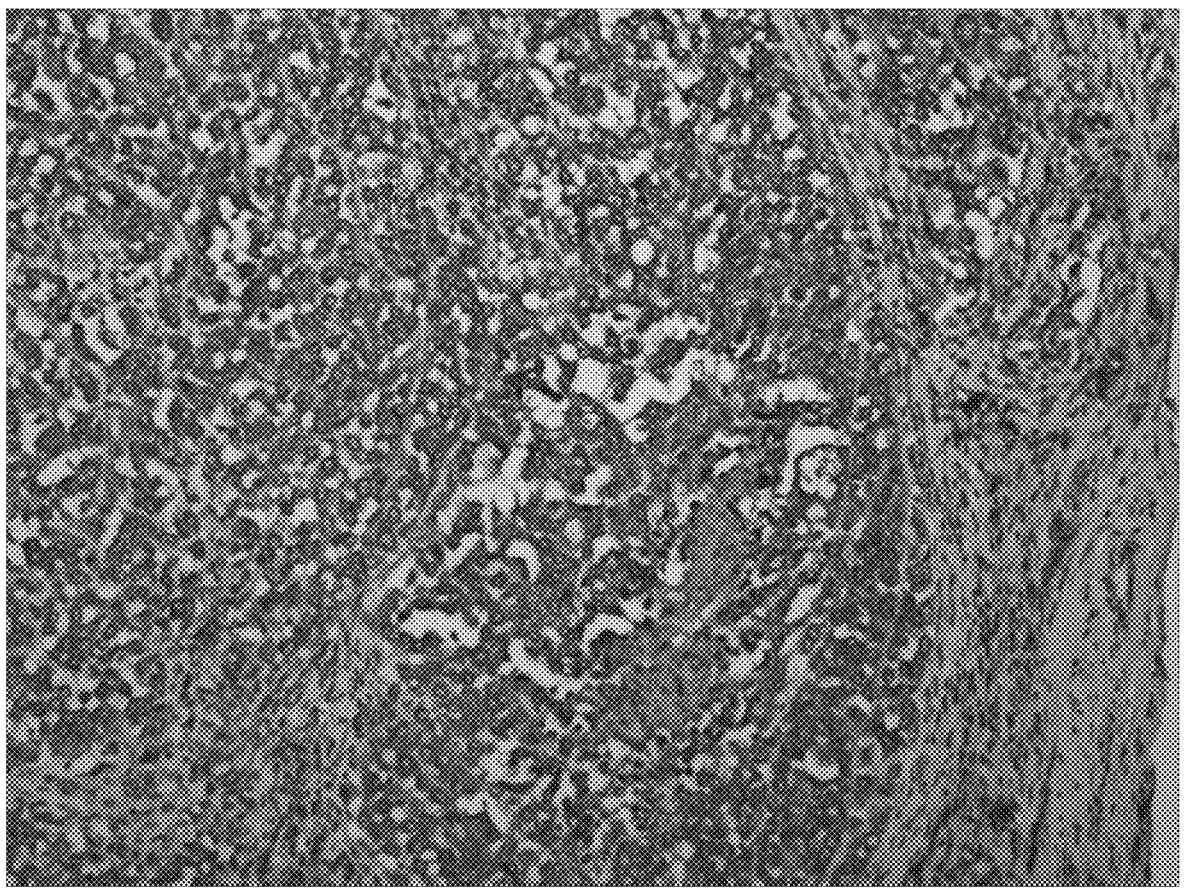

A section of human melanoma tissue similarly stained with 20 nM PEP2-4 dAb is shown in FIG. 10 below:

Conclusion: Antigen binding sites in the form of dAb leads for high affinity $P2X_7$ binding to PC3 cells were identified. Whether these antigen binding sites interact with a linear or conformational epitope was unknown and subsequently investigated. Refinement of the leads required added screening against a conformational epitope representing the shape of the E200 target antigen binding site as expressed on cancer cells Example 2—Determining Activity of dAb Leads in dAb-Fc Format Objective: The experiments described here have been to improve affinity of antigen binding sites that bind the E200 peptide through formatting lead dabs as dAb-Fc.

Background: Co-operative binding of the lead dabs was achieved by producing standard format dAb-Fc with human type IgG1 Fc subtype. These formats enabled more considered screening of the lead dAb clones by enabling the elimination of high affinity lead dabs for which formatting as dAb-Fc provided little benefit due to solubility issues. Favourable conformational solutions would then be selected for additional rounds of screening.

Figure 11:
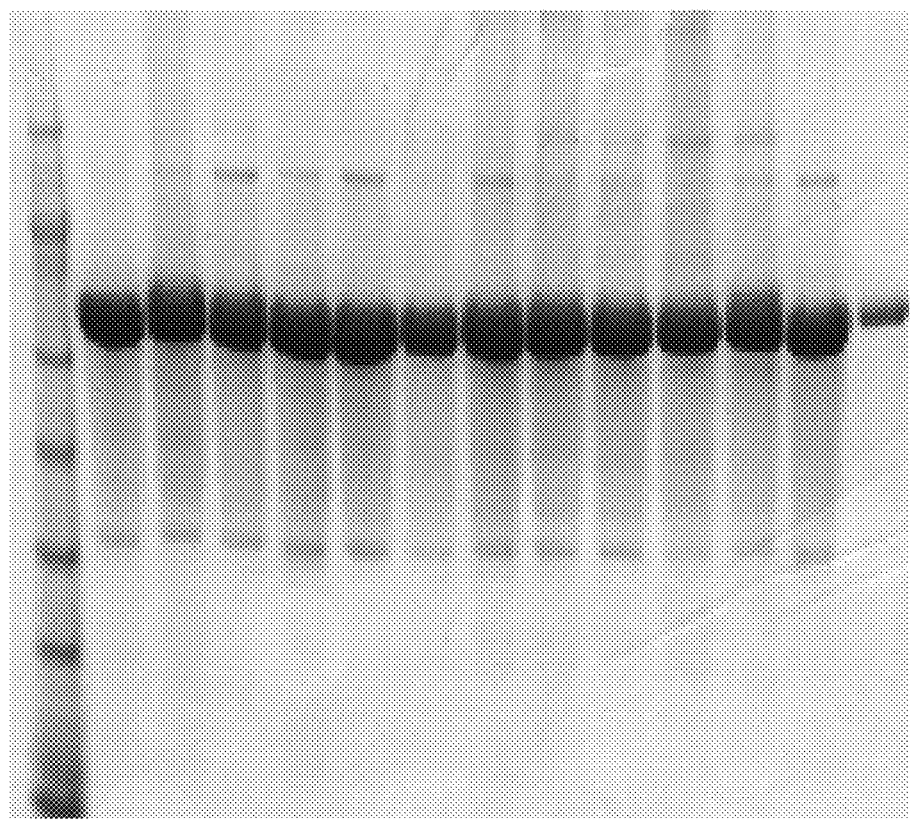
FIG. 11. Lead dAb-Fc expressing at a molecular weight of 75 kDa

Results: The first formatted dabs PEP2-4 and PEP2-5 that had been chosen as high affinity leads from Example 1 showed little additional binding to the E200 peptide whereas PEP2-2 and others (2-47, 2-42) benefited with a typical improvement in $K_D$ of 100-1000 times. Formatting of the various leads resulted in good expression as revealed in the SDS-PAGE gel in FIG. 11.

Figure 12:
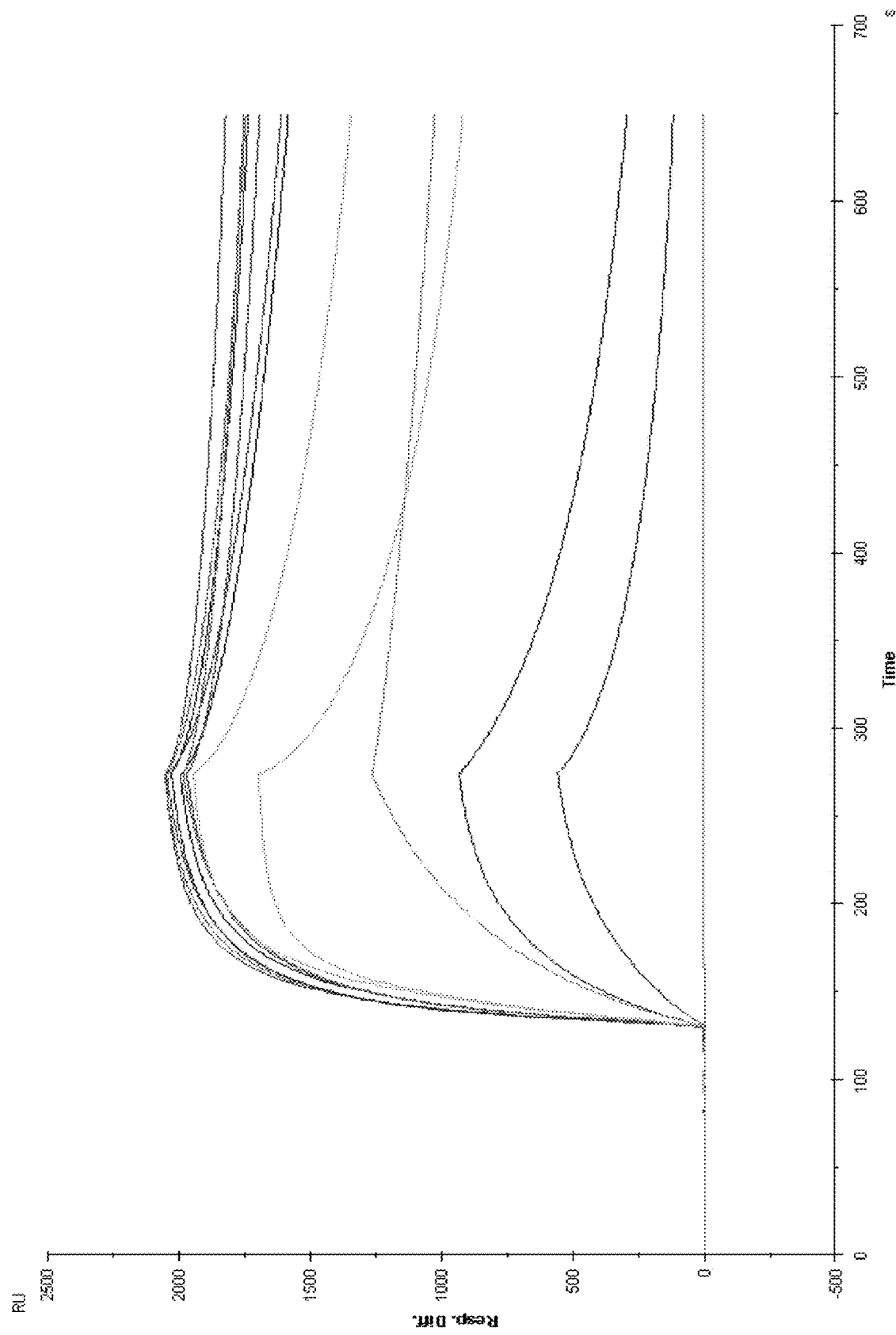
FIG. 12. Traces that can be easily resolved from the bottom include the control dAb, HEL4-Fc (green), PEP2-47, PEP2-42, PEP2-42-1, PEP2-2 (blue) with other higher affinity binders above. Flow rate was 50 uL/min.

The improvement in binding is evident with the leads including PEP2-2, PEP2-42, PEP2-47 shown in FIG. 12 in which the Biacore chip was coated with 100 RU of E200 and each dAb-Fc run at 100 nM.

Example 3—Determination of a Conformational Epitope for Screening dAb Leads Against Objective: The experiments described here have been to determine an appropriate conformational epitope for finding dAbs that bind the E200 peptide and also bind a conformational epitope.

Background: The high affinity binders are to bind to a non functional $P2X_7$ receptor extra cellular domain. The sequence of $P2X_7$ is shown in SEQ ID NO:1. There are a number of possible constructs that could be developed but we had to determine which of these would model the conformational epitopes as observed on a live cancer cell. We particularly needed a target that could be bound to a solid phase for later affinity maturation experiments.

We started with ECD1 that has the structure 47-332 because this constitutes all the amino acids forming the extracellular domain between the transmembrane domains TM1 and TM2 including the putative intramembranous segment at the C-terminus of the segment from 325-332. By including all the residues it was considered likely that the structure around the target E200 would be conserved.

Figure 13:
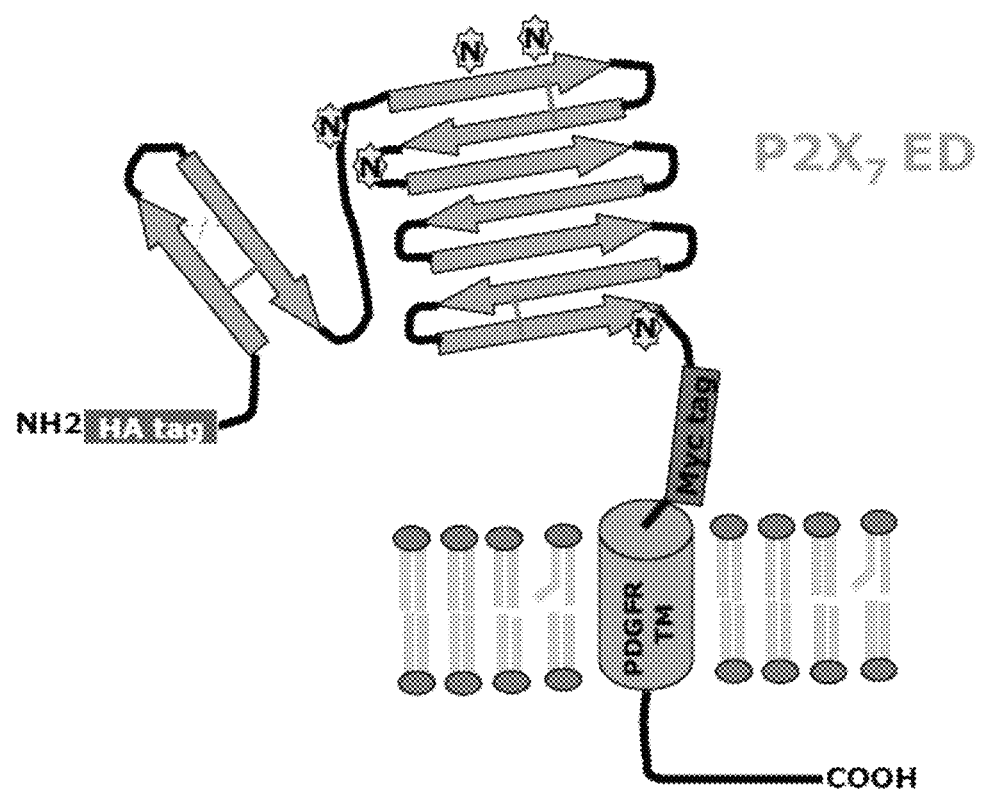
FIG. 13. The P2X$_7$ extracellular domain 47-332 with C-terminal c-Myc tag and N-terminal HA tag attached to PDGFR transmembrane anchorage for use in screening E200 conformational antigen binders expressed on HEK293 cells.

Materials and methods: ECD1 was constructed recombinantly using standard molecular biology procedures and expressed in *E. coli* cells as soluble protein and formatted as ECD-Fc and in pDisplay for immunofluorescence, Western Blotting and flow cytometry. The pDisplay structure had the form shown in the schematic in FIG. 13.

Figure 14:
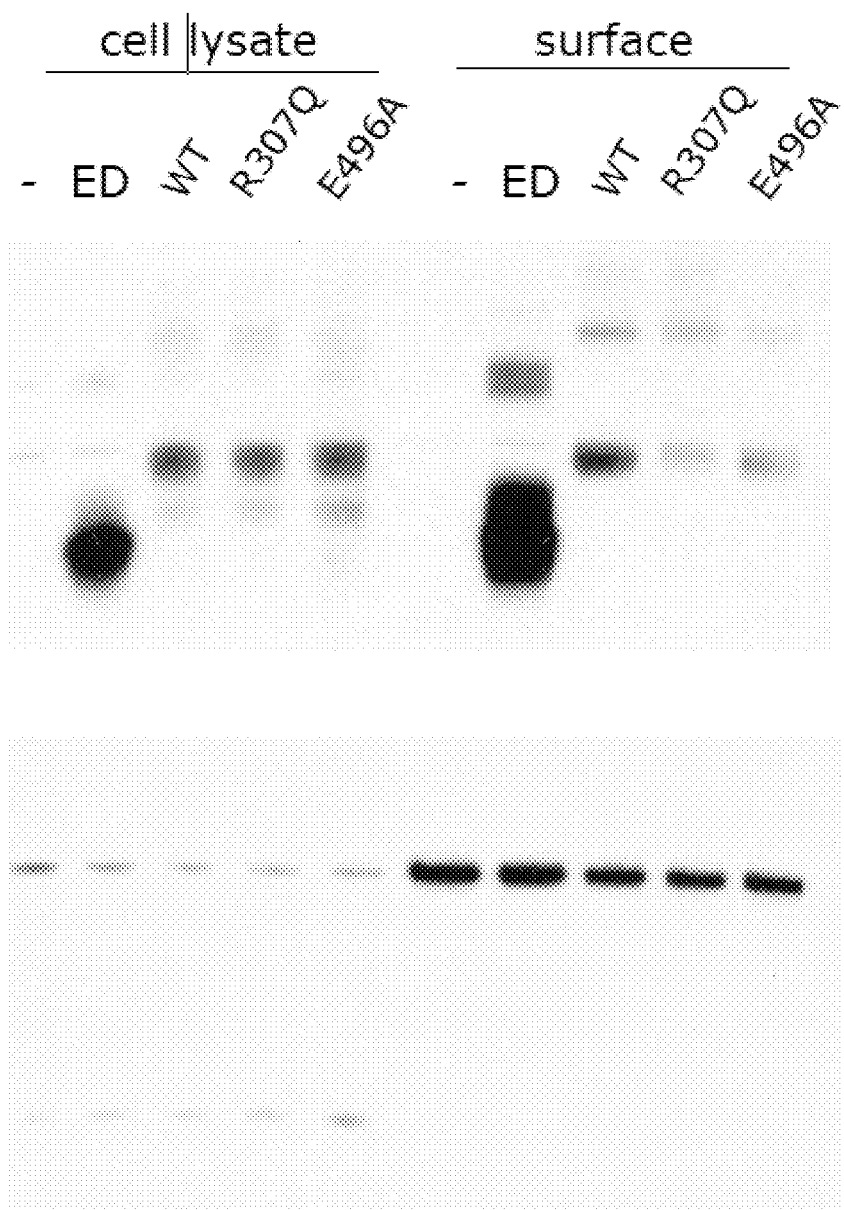
FIG. 14. SDS-PAGE Western blot of cell lystate and surface expressed proteins expressing the ECD1, wild type (WT) P2X$_7$ and the two non-functional P2X$_7$ receptor mutants R307Q and E496A. The ECD1 is expressed at 52 kDa, the three P2X$_7$ receptors at 75 kDa. Anti-cadherin control in the lower section is at 98 kDa and anti-actin in the cell lysate at 42 kDa.

Results: Cell surface expression of P2X$_7$ in the form of the wild type (WT) and in two non-functional full length mutant forms (R307Q and E496A) were compared along with the ECD1 in HEK293E cells and measured with Western Blot. Cell lysates and cell surface expression was compared in all three forms and the labelling to the ECD1 added. Anti-cadherin was used as a standardisation control. The cells were biotinylated with sulfo-NHS-SS-biotin, the reaction quenched and lysis performed with mild detergent. At this stage an aliquot was retained for indication of total cell protein. Biotinylated protein was captured with neutravidin resin that was washed and eluted with 50 mM DTT. The supernatant was retained for an indication of the intracellular pool of specific protein. The samples were then run on standard reducing SDS PAGE/Westerns (FIG. 14).

Cell surface expression indicates a reduction in the levels of the non-functional mutants compared with WT on the cell surface. The ECD1 expression from expressed pDisplay is efficiently high. This form of the protein is labelled by antibodies to the non-functional form of the receptor, the tumour specific form and can therefore be considered a possible tumour representative form. Monocytes, in contrast, expressing the WT form, were unable to bind the dAbs. The efficiency of binding of the dabs to the pDisplayECD1 was lower than the levels of expression indicated should have been the case. This indicates that the target epitope is sterically hindered from binding on live cells and that the structure of ECD1 is sub-optimal.

Conclusion: While ECD1 construct was bound by dAb leads indicating binding to a conformational epitope, binding was suboptimal which raised the questions concerning whether this construct would be useful for affinity maturation studies.

Example 4—Determining a Further Construct for Affinity Maturation of Lead dAbs

Objective: To produce a construct that could be used in affinity maturation studies.

Background: Example 3 revealed that certain ECD isoforms might not reproduce conformational epitopes of P2X$_7$ as observed on live tumours. We decided to pursue a further construct in the form of the structure 47-306 (ECD2).

Materials and methods: ECD2 was constructed recombinantly as in Example 3, in soluble form, Fc format and as pDisplay for immunofluorescence, Western Blotting and flow cytometry.

Figure 15:
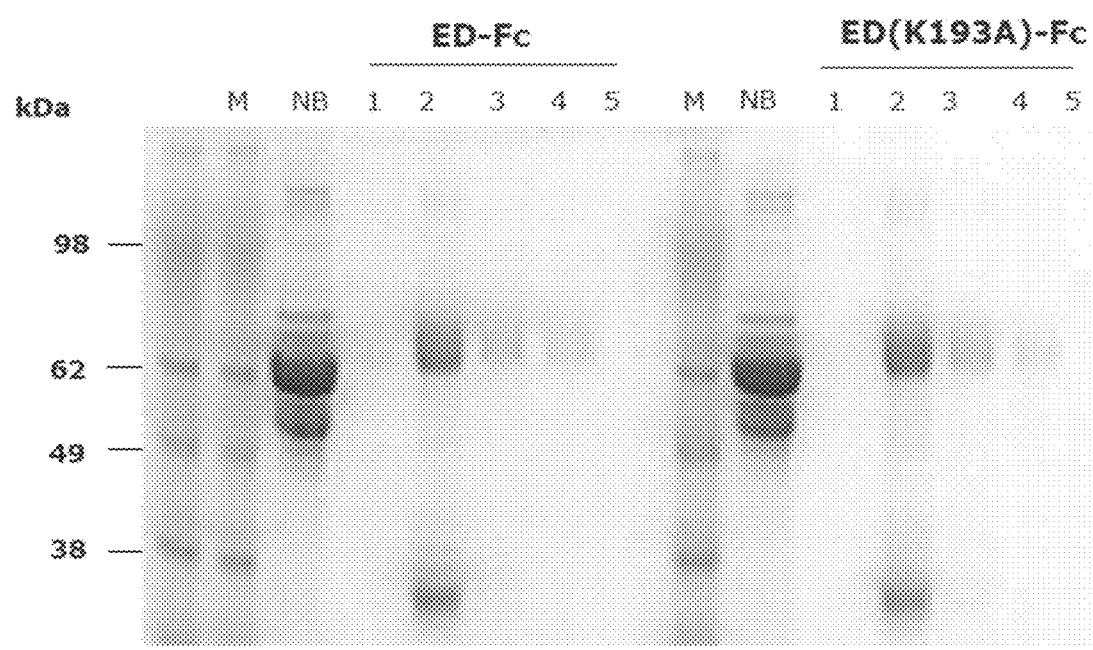
FIG. 15. SDS-PAGE of ECD2 (47-306) and a mutant construct K193A(47-306) showing protein A fractions 1-5 and the supernatant (NB) with molecular weight standards at left.

Results: ECD2 expression as an Fc construct is shown in FIG. 15. A reducing SDS-PAGE with Protein A fractions shown in two forms: WT (functional) and K193A (non functional) mutant forms. dAbs were identified that bind the ECD2 construct. NB is an aliquot of the supernatant representing protein not bound by Protein A.

Figure 16:
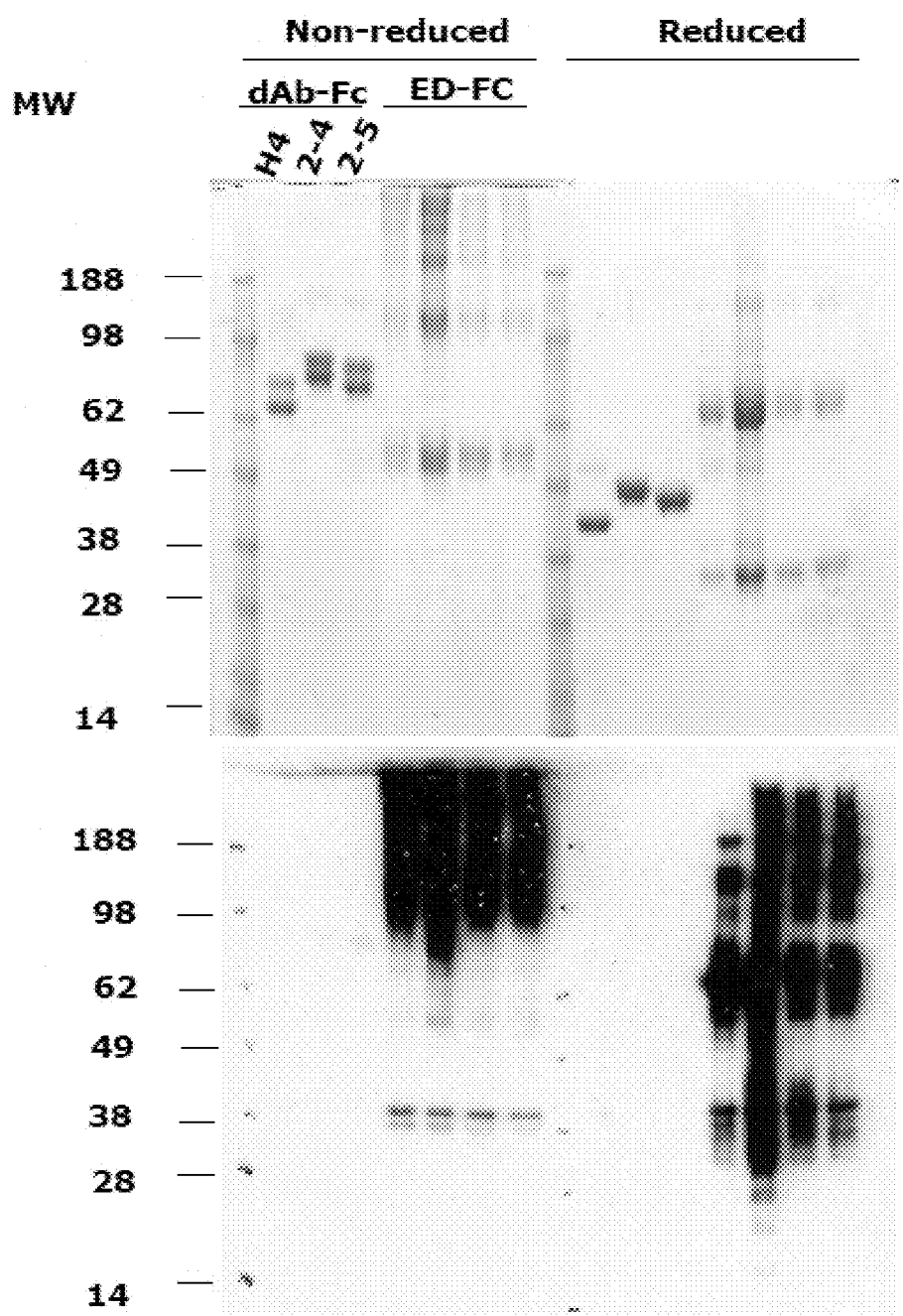
FIG. 16. SDS-PAGE both non-reduced and reduced of dAb-Fc and ECD2-Fc along with corresponding Western Blots reacted with anti-P2X$_7$ antibody.

The dAb-Fc species PEP2-4 and PEP2-5 along with control dAb HEL4 were run on non-reduced and reduced gels and corresponding Westerns run on the fractions revealed with anti-P2X$_7$ antibody (FIG. 16). Both dAb-Fc expression and ECD2-Fc expression is clear. The reduced gels show specific label on the ECD2Fc of the anti-P2X$_7$ antibody at 62 kDa with a lower molecular weight proteolytic fragment (single chain) at 31 kDa. The corresponding Western shows reactivity with both ECD2 bands but none with HEL4Fc, PEP2-4Fc or PEP2-5Fc.

Figure 17:
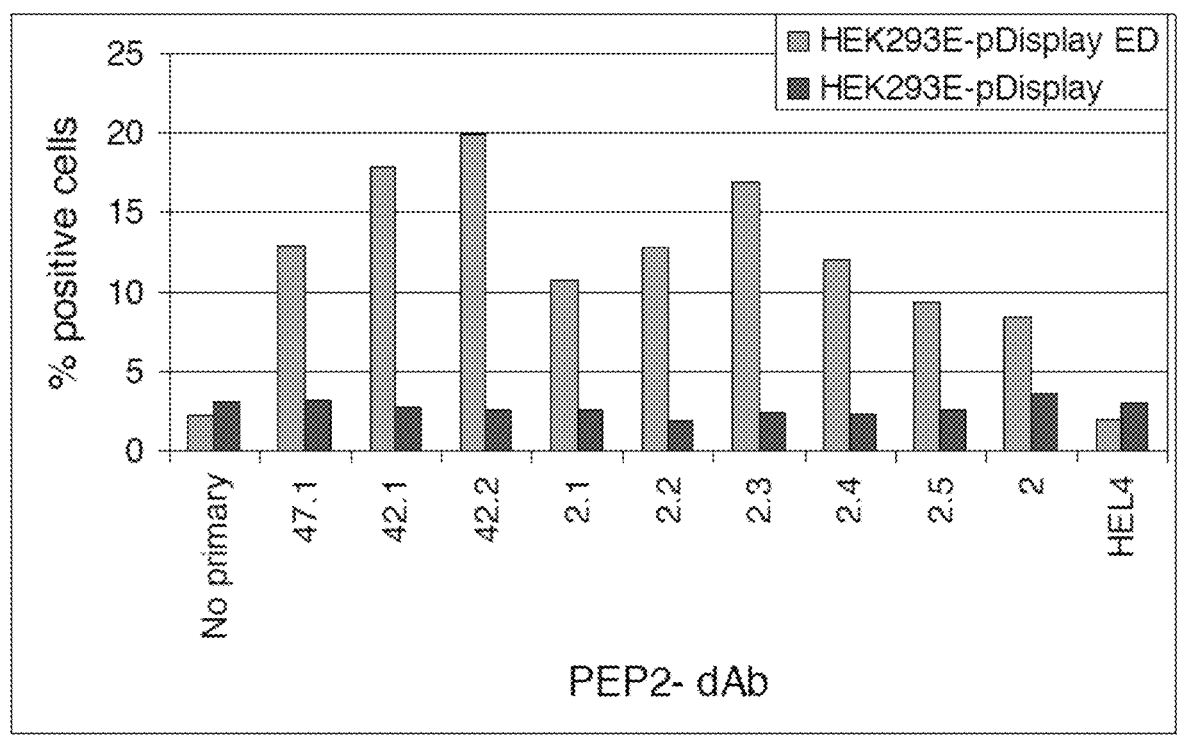
FIG. 17. A selection of dAbs tested at 5 uM. Staining was detected with anti-human IgG Fab.
Figure 18:
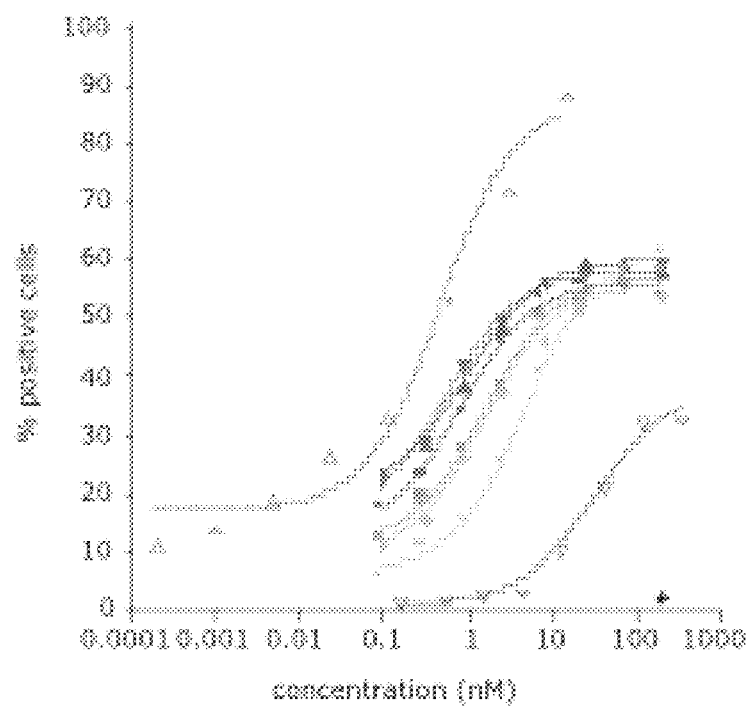
FIG. 18. Flow cytometry of the dAb-Fc binding to the pDisplay-ECD2 on HEK cells showing tighter cell binding by higher affinity species.

Binding by flow cytometry to live HEK293E cells expressing pDisplay-ECD2 was clearly improved (FIG. 17). Gating live cell binding with HEL4 as the control negative binder showed clear improvements with a higher percentage of positive cells detected with lead dAbs indicating the target epitope was less sterically hindered and available for binding (FIG. 18).

Conclusion: Antigen binding sites have been identified that bind the non-functional P2X$_7$ receptor on live cells and ECD2. The removal of residues 307-332, commencing an estimated 3 nm from the E200 epitope site, has improved binding with the removal of partial steric hindrance. No loss of E200 conformation occurs even though the segment 307-332 would be expected to stabilise the protein fold as it interacts closely with the N-terminal segment.

Example 5—Generating Various High Affinity Binders

Objective: To generate antigen binding sites with high affinity for the non-functional P2X$_7$ receptor.

Background: The antigen binding sites from Example 1 having the following sequences:

| | CDR1 | CDR2 | CDR3 |
|---|---|---|---|
| WT | SSYAMS | ---AISGSGGSTYYADSVKG--- | CAKSYGA--------FDY |
| PEP2-2 | RNHD.G | ---AISGSGGS...............  | ..EPKPMDTE------..Y |
| PEP2-47 | PMKD.G | ---AISGSGGS...............  | ..EPSHFDRP------..Y |
| PEP2-42 | DNVE.S | ---SIGSKGED...............  | ..QTVNVPEPA-----.AY |
| PEP2-1 | DNEP.G | ---S.AD..NH...............  | ..QR.LNRYRAQ--...Y |
| PEP2-5 | PASN.. | ----S.TA..YR...............  | ..QGQISNFPR----..Y |
| PEP2-4 | GM.N.. | ----S.NAT..R...............  | ..FNRFSHRQYN--...Y |
| PEP2-34 | ........ | ---T.TSD.LR...............  | ..VHTFANRSLN--...Y |
| PEP2-7 | GA.S.. | ----T.N...LA...............  | ..CSSCTSLNAN--...Y |

-continued

| | CDR1 | CDR2 | CDR3 |
|---|---|---|---|
| PEP2-11 | AR.P.A---S.D.G.LQ | ............----... | ASAPKYFR-----..Y |
| PEP2-30 | AK.P.V---S.GPG.AR | ............----... | PWRVYSYDR----..Y |
| PEP2-13 | ...A.A---T.D.N.LI | ............----... | LQRYDRYTLN..Y | were used as starting points for iterative rounds of randomization and screening subject to issues of binding in the Fc format, solubility and possession of a uniphasic dissociation trace on Biacore. PEP2-2 and PEP2-47 possessed the requisite characteristics and were selected for affinity maturation even though they surprisingly had lower single domain affinity for the ECD2 conformational and E200 peptide targets than other lead dabs such as PEP2-4 and PEP2-5.

Materials and methods: The selected $V_H$ domains including 2-2, 2-47 and daughters ere affinity matured through 6 rounds of sequence diversification that included all CDRs as well as all framework regions through NNS diversification that sampled all 20 amino acids at each position. The scaffold of the $V_H$ library originated from the human $V_H$ that gave rise to the HEL4 control non-binder and the diverse positive binders has the sequence:

VHD EVQLLEPGGGLVQPGGSLRLSCAASGVNVSHDSMTWVRQAPGKGLEW

VSAIRGPNGSTYYADSVKGRFTISRDNSKNTLYLQMNSLRAEDTAVYYCAS

GARHADTERPPSQQTMPFWGQGTLVTVSS

Error-prone libraries were generated with a 2.7 amino acid error rate. Pools of clones were screened against the E200 initially and then the ECD2 by phage ELISA for increased binding affinity. Eight error-prone libraries were subcloned into the soluble dAb expression vector pDOM38 without tag. Passive selection was carried out until Round 3. A total of 1000 clones were screened by Biacore from Round 5 libraries PEP2-42, PEP2-pooled and the Round 4 library PEP2-pooled. The pool of clones represents PEP2 clones 2-1, 2-2, 2-11, 2-13, 2-30, 2-34, 2-42 and 2-47. Improvement in off-rates by Biacore were observed. ELISA screening against 1 nM biotinylated E200 showed $EC_{50}$ improvement from the range $10^7$ to $10^6$ ug/mL in Round 3 to $10^4$ ug/mL in Round 5, well above control dAbs.

Figure 19:
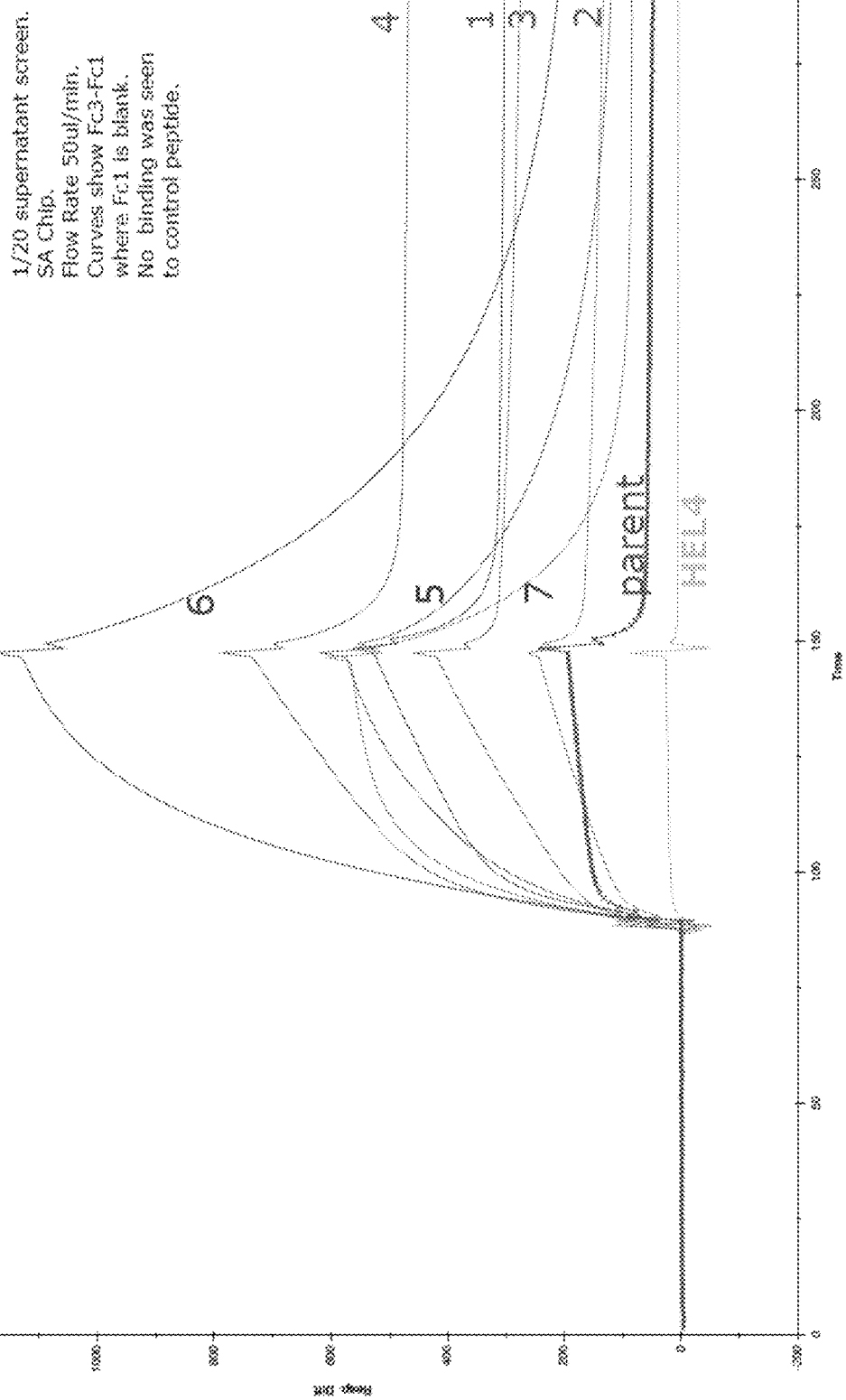
FIG. 19. Biacore tracings of selected PEP2-42 clones showing improved binding to E200 peptide.
Figure 20:
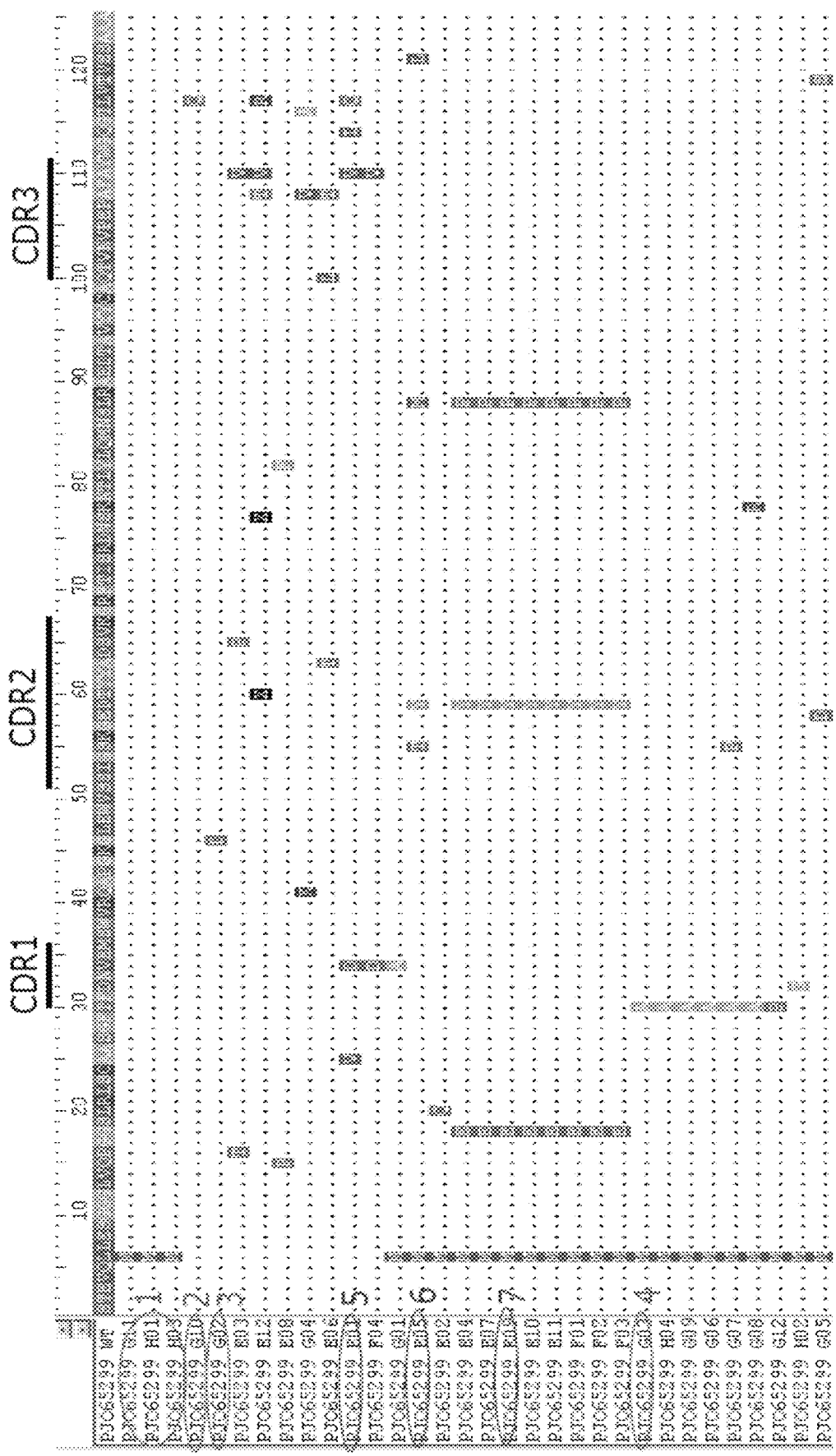
FIG. 20. Sequences of PEP2-42 clones.

Biacore tracing of selected PEP2-42 clones to E200 peptide are shown in FIG. 19. The parent clone and HEL4 control dabs are at the bottom of the figure. Sequence variations of the selected clones are shown in the following figure. The 32 clones shown all have improved off-rates. Off-rate curves fell into two families and clones were chosen accordingly (FIG. 20) with E/F (blue at left) representing a classical off-rate curve and G/H (red at left) an irregular biphasic type. $K_D$ values are 76 nM for clone 6 and 200 nM for clone 7.

Determination of biochemical and/or biophysical characteristics of the antigen binding sites were obtained by SEC-MALLS. Those with monomeric solution characteristics were selected over those with a propensity to aggregate. Clones were generally found with a solubility in PBS>10 mg/mL.

NNS screening, particularly of part of the variable CDR3 region, but extending to critical residues in F4 such as the residues 103-105 was used to refine antigen binding.

Figure 21:
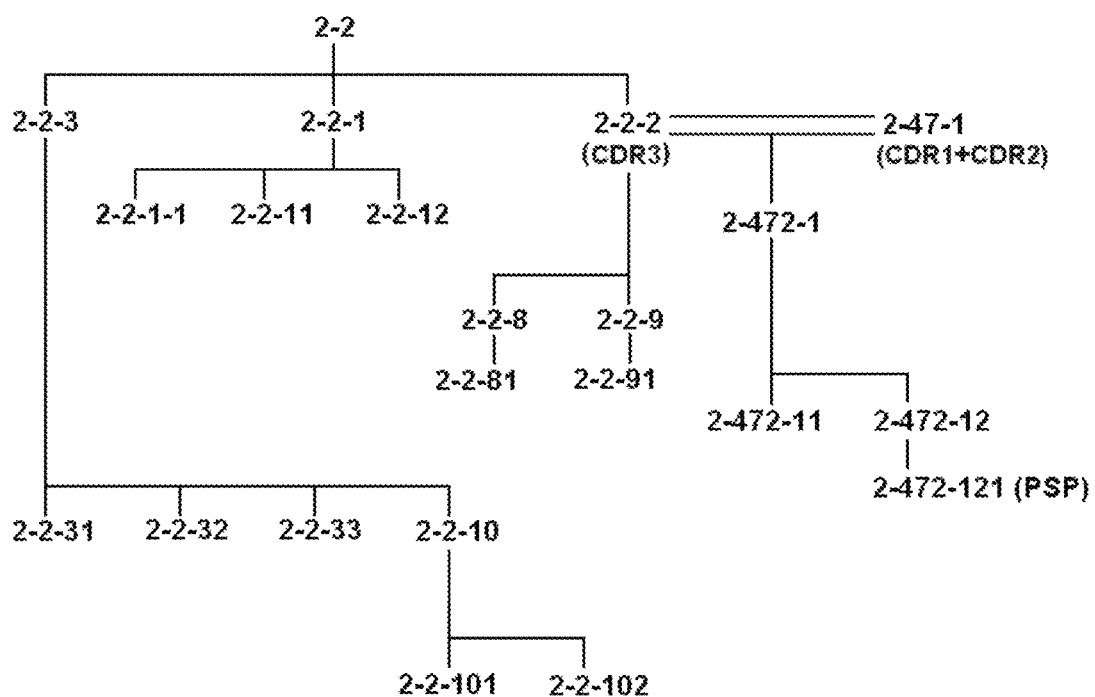
FIG. 21. Tree of affinity maturation pathways from lead binder to expressed extracellular domain of target receptor FIG. 22. Biacore traces of the PEP2-2-3 Fc clone at increasing concentrations run against 10 RU of E200 peptide.
Figure 22:
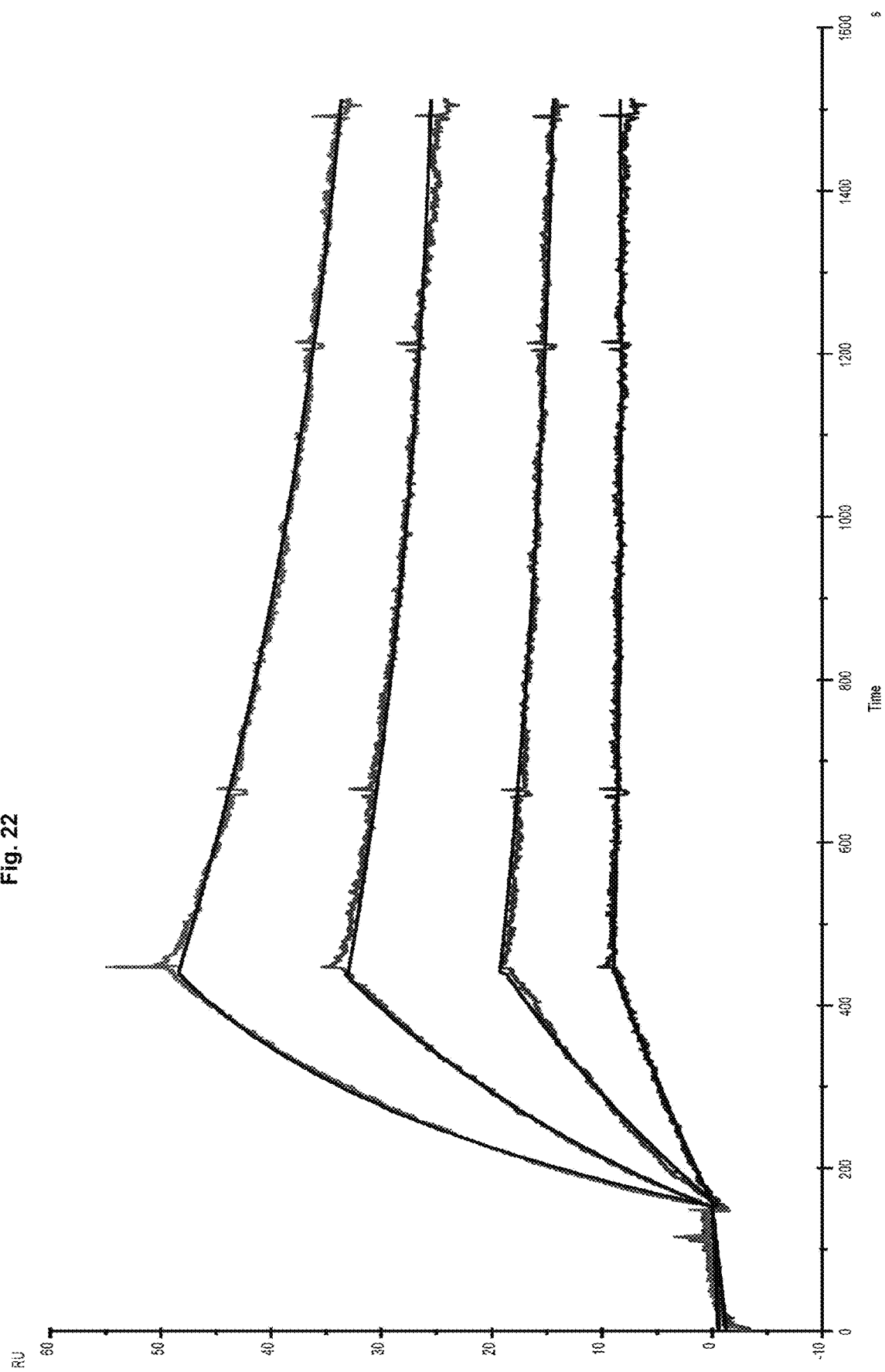

Results:

The affinity maturation family tree of antibodies is shown in the FIG. 21. An example of the improved binding by Biacore is shown in the form of the clone PEP2-2-3Fc in FIG. 22. The channel was coated with 10 RU E200 peptide and then loaded with 100 pM, 250 pM, 500 pM and 1 nM PEP2-2-3 in ascending order on the figure. Curve fitting reveals a $K_D$ of 130 pM. The corresponding value for the unformatted dAb PEP2-2-3 against E200 is 7 nM, showing a more moderate increase in binding for the high affinity dabs when formatted as dAb-Fc compared with the increase from the parent dabs such as PEP2-2 that increased from 1 uM to 300 μM.

Corresponding values for the $K_D$ when measured against ECD2 in either solution form or as a ECD-Fc construct showed significantly lower binding against the conformational epitope, with PEP2-2-3 Fc producing a value of 1.5 nM, PEP2-2-1560 pM and PEP2-472-1584 pM as examples.

Examples of PEP2-Fc KD derived from Biacore using E200 are shown in the following Table.

| PEP-Fc | $K_D$ (pM) |
|---|---|
| 2-2 | 300 |
| 2-2-2 | 100 |
| 2-2-3 | 130 |
| 2-2-1-1 | 90 |
| 2-42 | 5,500 |
| 2-42-1 | 120 |
| 2-47 | 7500 |
| 2-47-1 | 110 |
| 2-247-1 | 190 |
| (2-2/2-47-1 CDR crossover) | |
| 2-247-2 | 450 |
| (2-2-1/2-47-1 CDR crossover) | |
| 2-472-1 | 90 |
| (2-47-1/2-2-2 CDR crossover) | |

Figure 23:
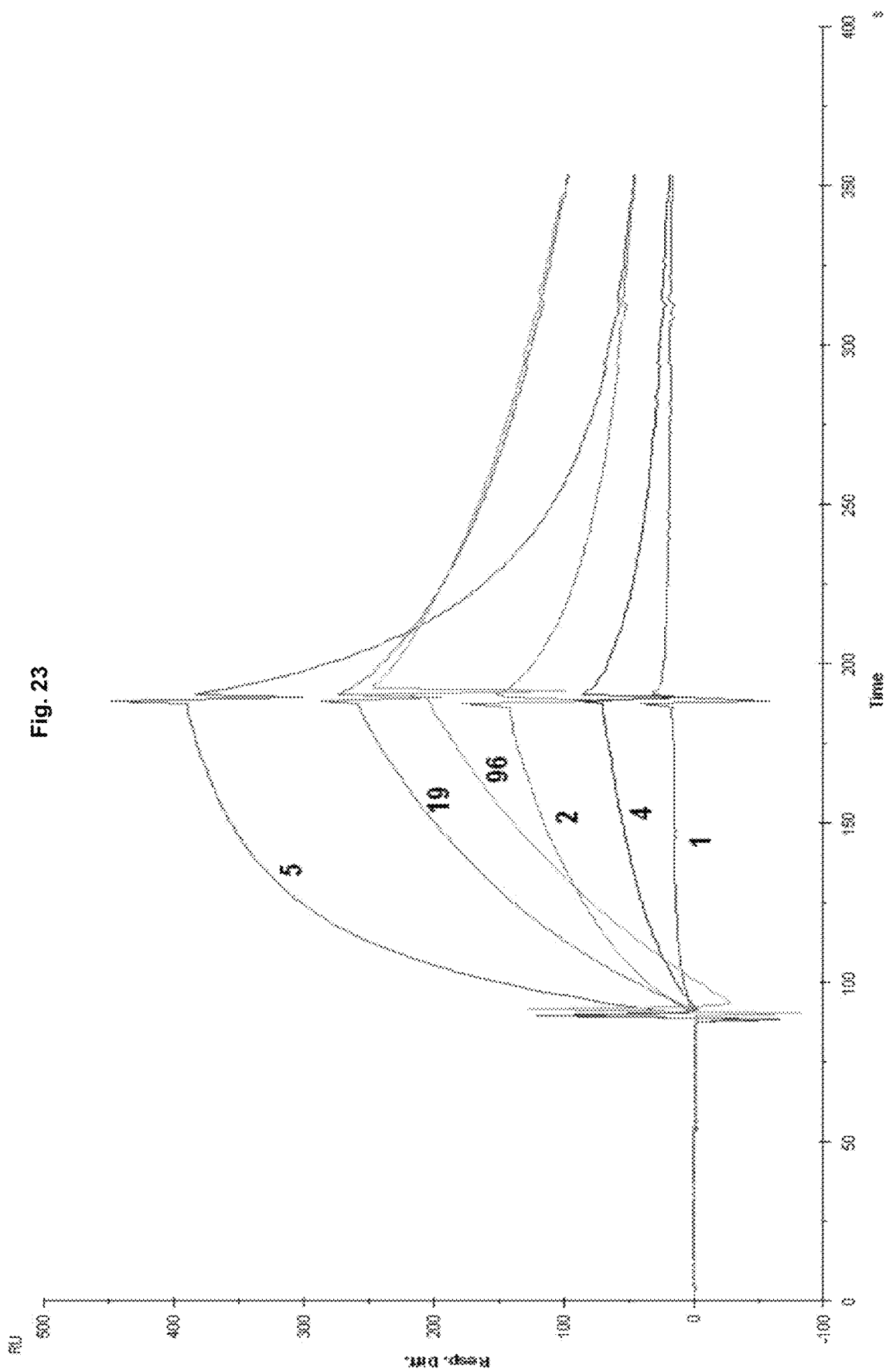
FIG. 23. Biacore traces of clones produced by NNS screening of Trp103 in PEP2-2-1.

The effect of NNS screening on position 103 in PEP2-2-1 is shown in FIG. 23. Trace 1 is buffer only and Trace 5 is a typical example of improved binding obtained by exchanging the Trp for an Arg residue.

Figure 24:
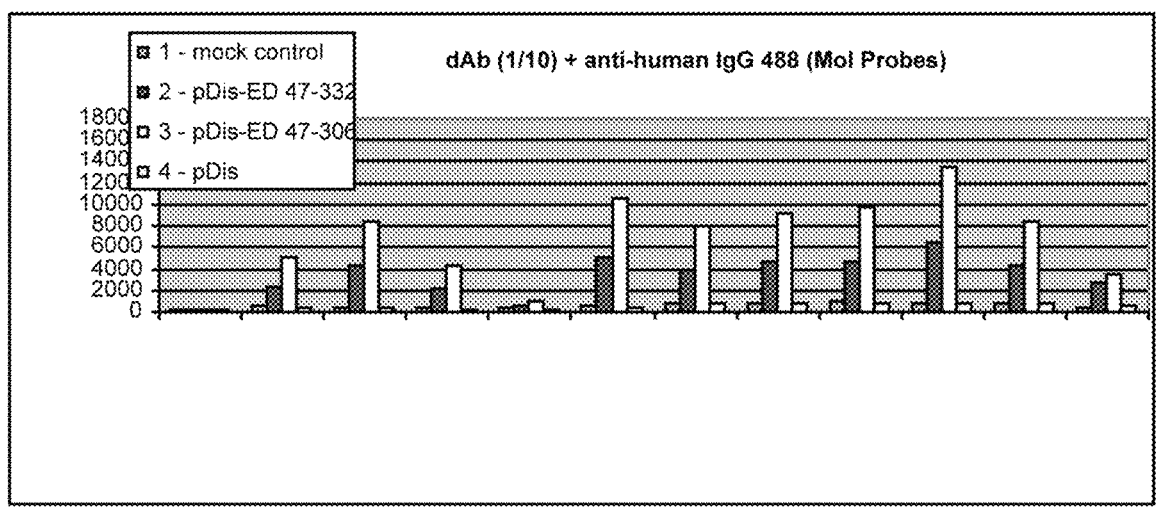
FIG. 24. Binding by flow cytometry of PEP2-2-1 to cells expressing ECD1 or ECD2 together with controls (mock and pDisplay only).

Binding of selected lead clones to HEK293 cells expressing mock control (no binding), pDisplay-ECD1 (moderate binding), pDisplay-ECD2 (higher binding) and pDisplay control (no binding) is seen in FIG. 24.

Figure 25:
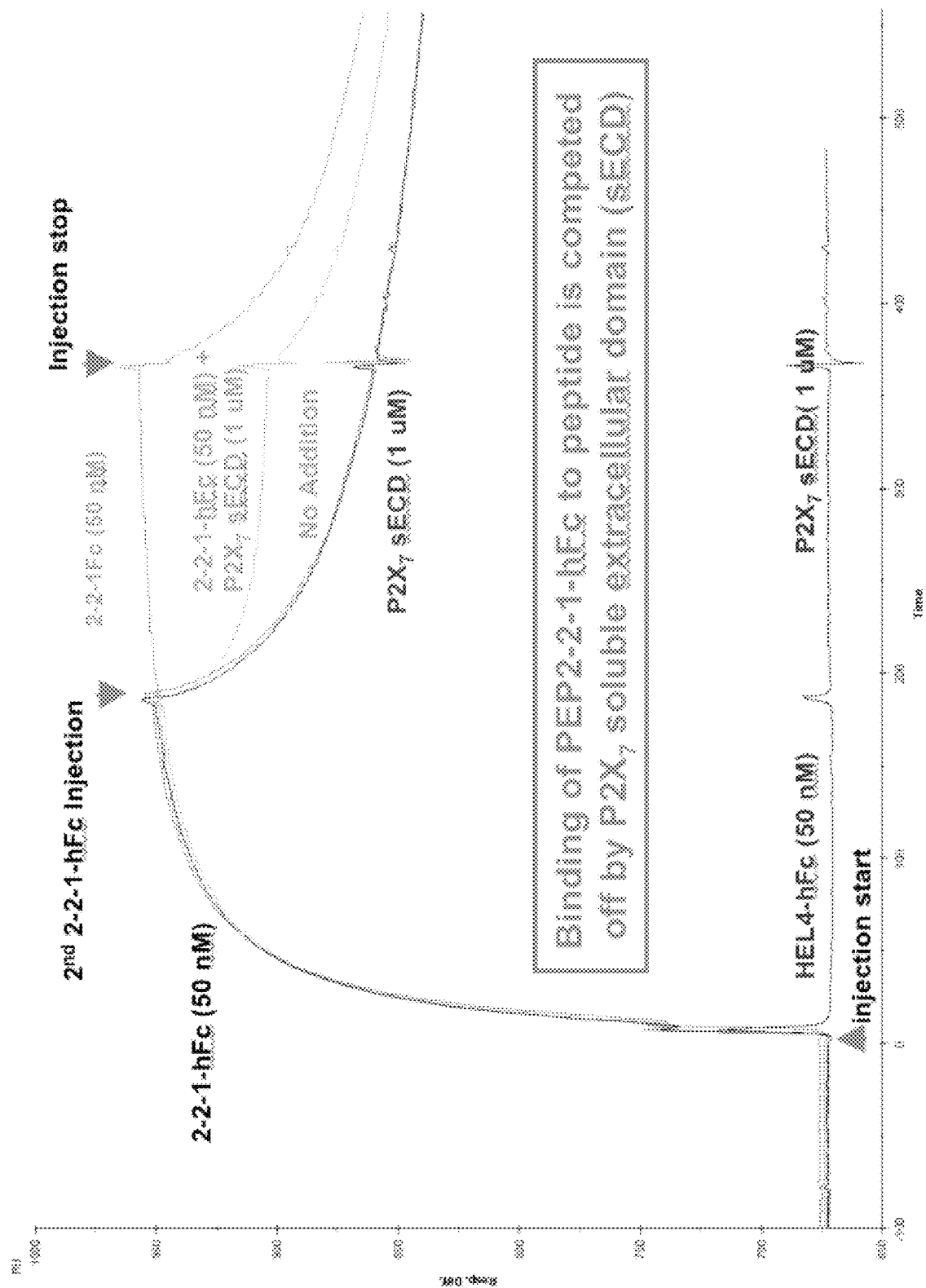
FIG. 25. Biacore tracings showing competitive binding between PEP2-2-1, E200 peptide and ECD2 (47-306).

The lead clones bind specifically and competitively to the target antigen and can be competed off with the addition of the soluble ECD2. As an example FIG. 25 shows PEP2-2-1 Fc at 50 nM is competed off with 1 uM of soluble ECD2. An SA Biacore chip is coated with E200-biotin peptide. Data shown is from 20 RU coated channel with a flow rate of 20 uL/min in HBS-EP buffer. The HEL 4 Fc neither binds nor is affected by the addition of the ECD2. Similar results are achieved in competing off the PEP2-2-1 Fc with E200 at 5 uM or the ECD2 Fc construct at 1 uM.

Figure 26:
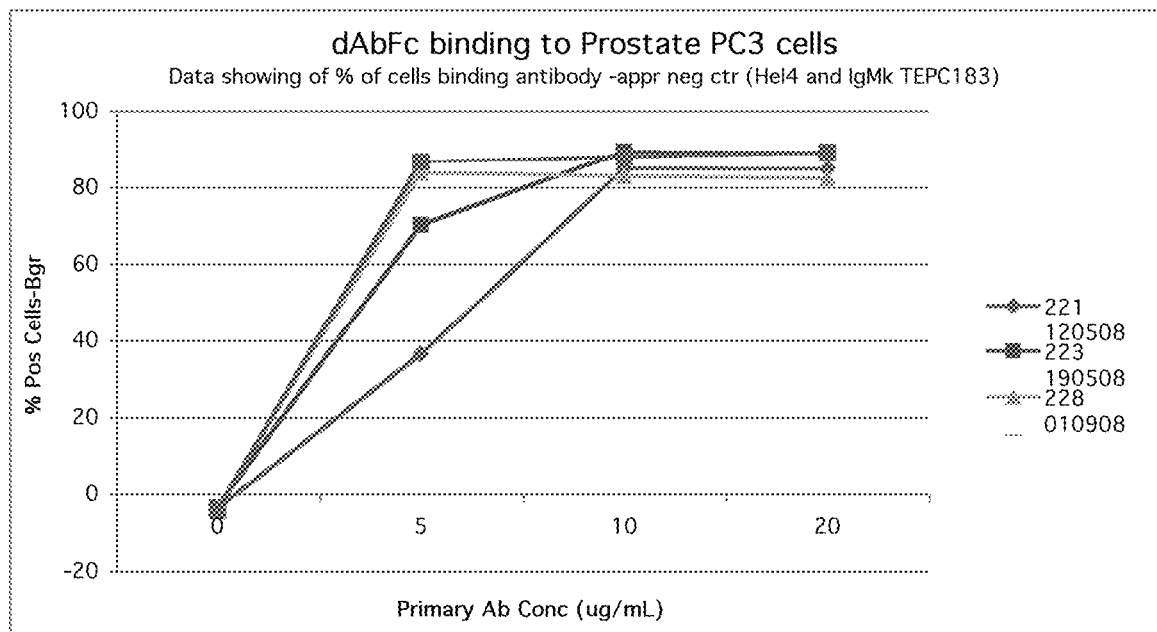
FIG. 26. Lead dAbs 2-2-1 Fc, 2-2-3 Fc and 2-2-8 Fc binding to live prostate PC3 cells at 0-20 ug/mL.
Figure 27:
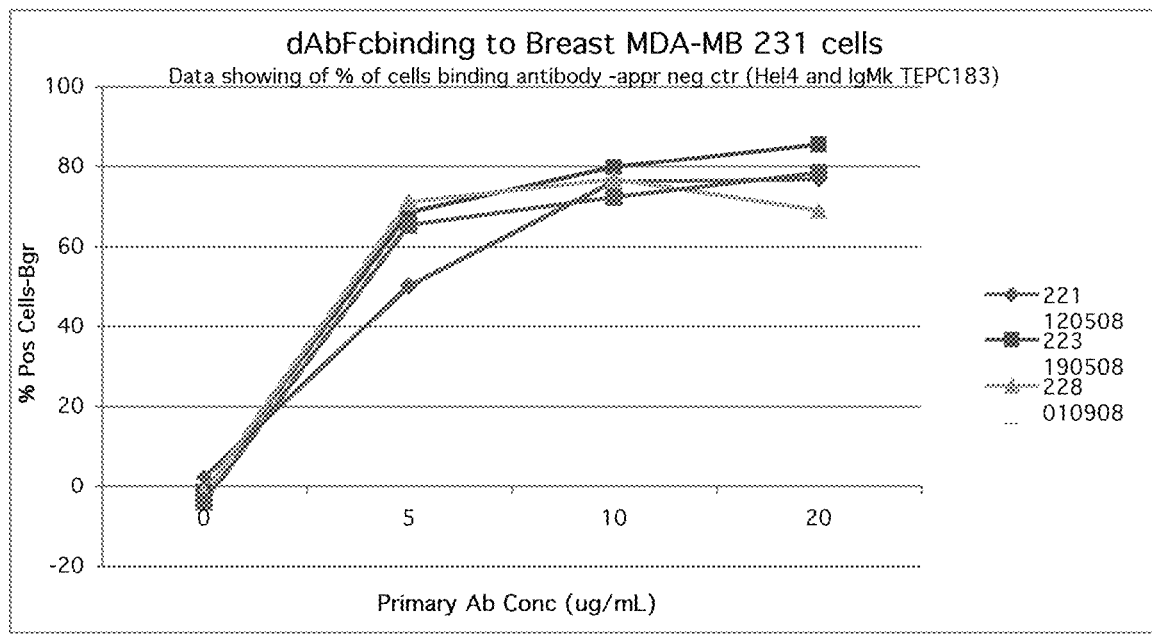
FIG. 27. Lead dAbs 2-2-1 Fc, 2-2-3 Fc and 2-2-8 Fc binding to live breast MDA MB 231 cells at 0-20 ug/mL.
Figure 28:
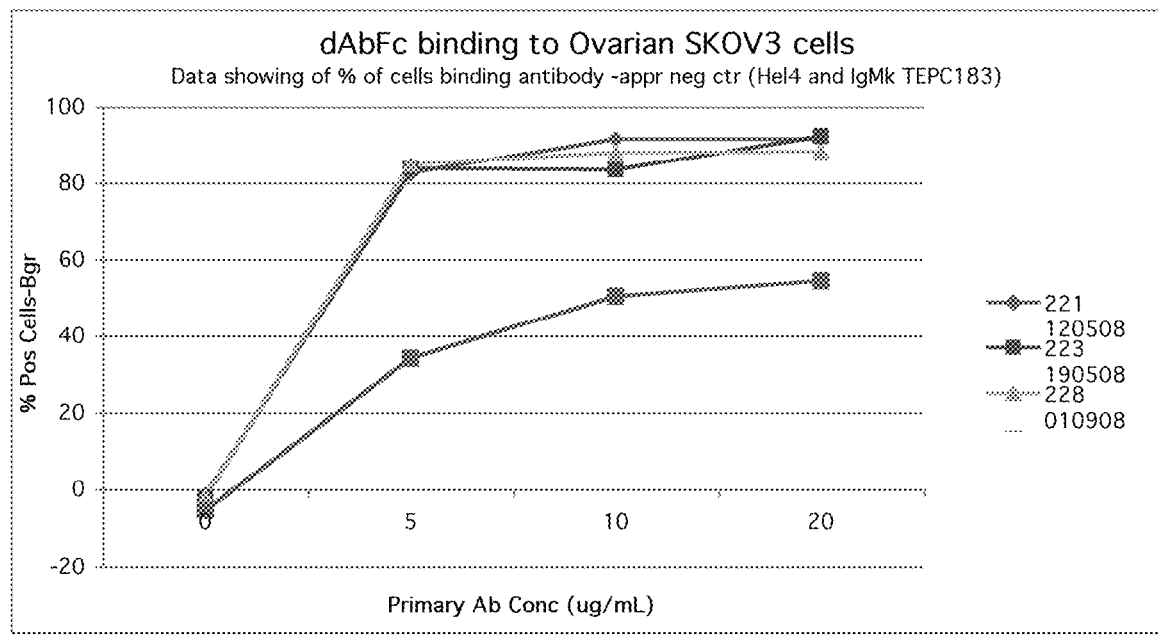
FIG. 28. Lead dAbs 2-2-1 Fc, 2-2-3 Fc and 2-2-8 Fc binding to live ovarian SKOV-3 cells at 0-20 ug/mL.
Figure 29:
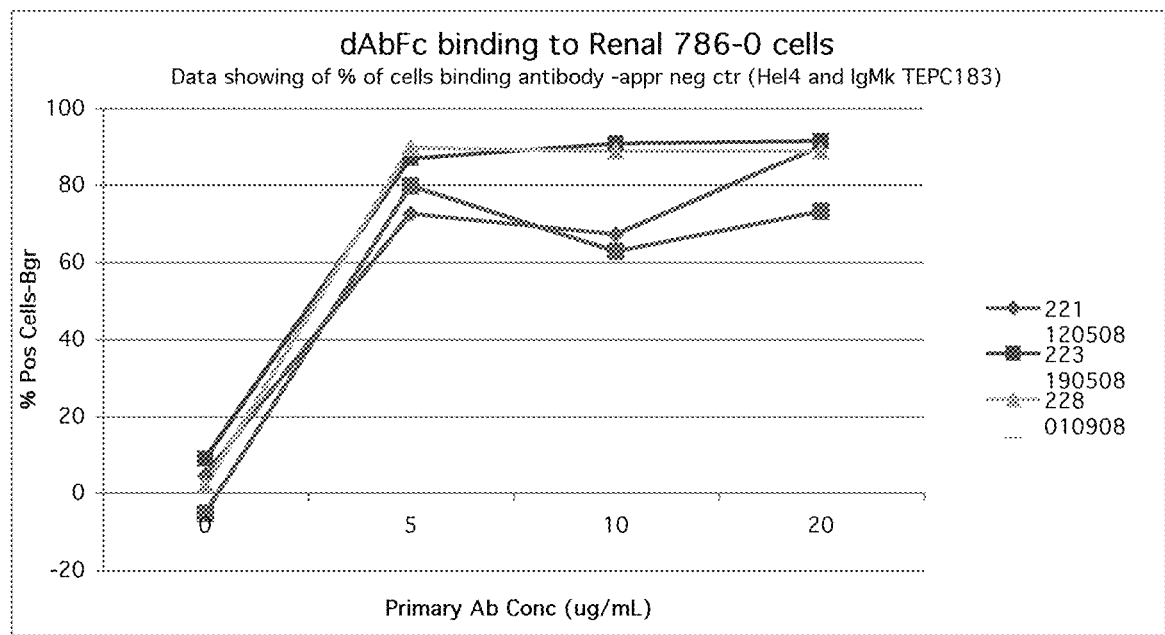
FIG. 29. Lead dAbs 2-2-1 Fc, 2-2-3 Fc and 2-2-8 Fc binding to live renal 786-0 cells at 0-20 ug/mL.
Figure 30:
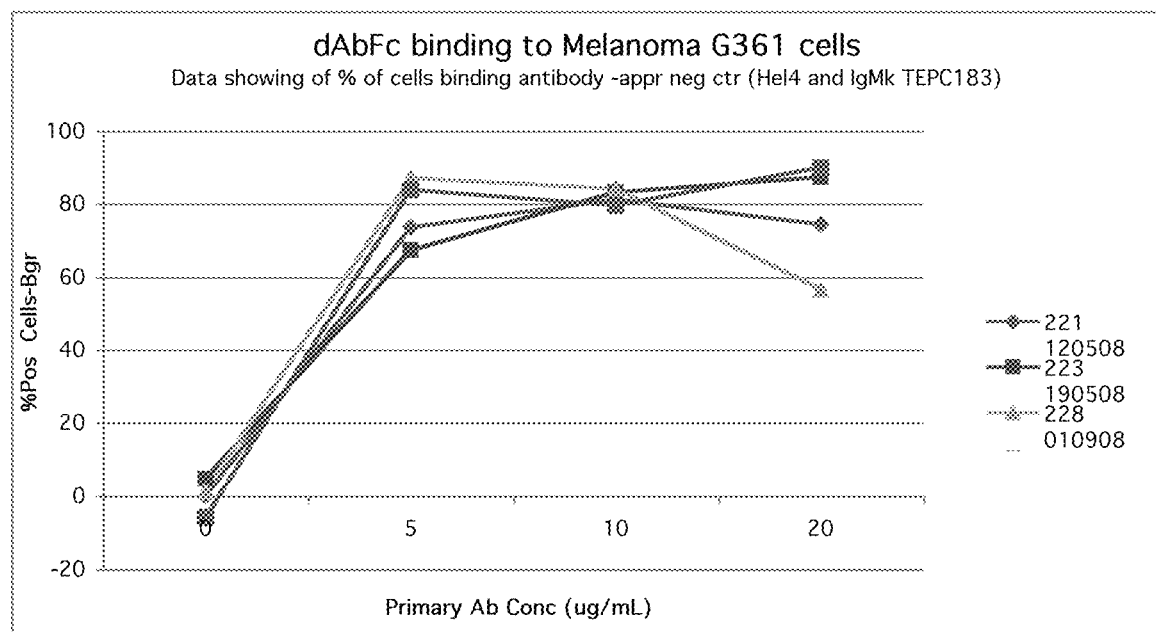
FIG. 30. Lead dAbs 2-2-1 Fc, 2-2-3 Fc and 2-2-8 Fc binding to live melanoma G361 cells at 0-20 ug/mL.
Figure 31:
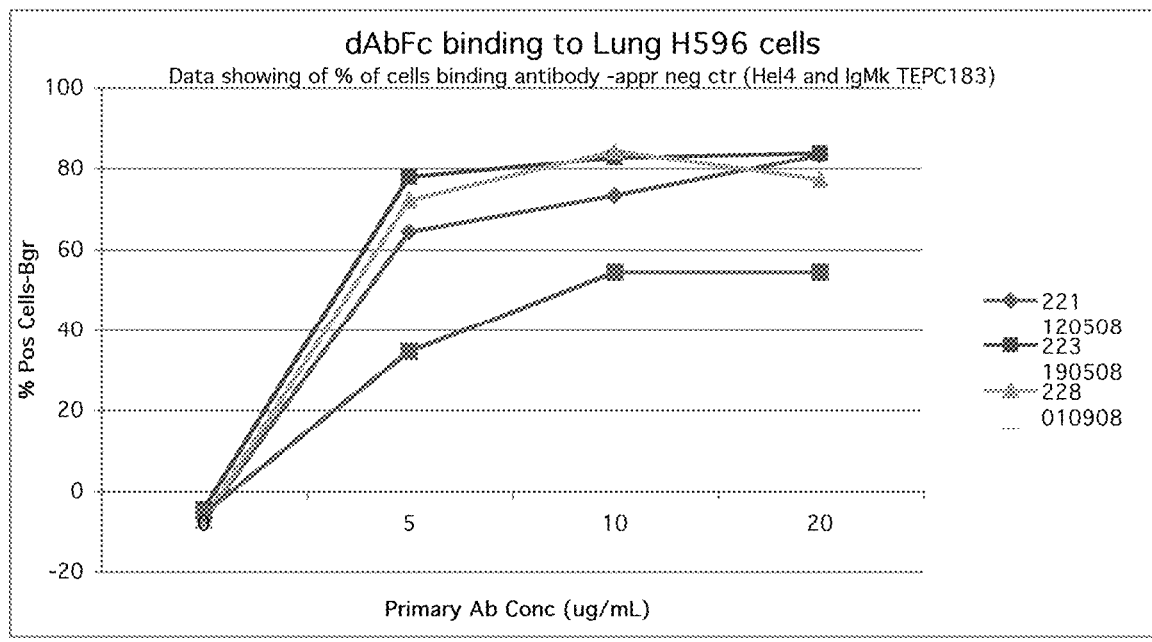
FIG. 31. Lead dAbs 2-2-1 Fc, 2-2-3 Fc and 2-2-8 Fc binding to live lung NCI-H596 cells at 0-20 ug/mL.

Flow cytometry of binding of several lead dAb-Fc antigen binders to live cancer cells is shown in the following examples. These include: prostate PC3 (FIG. 26), breast MDA-MB 231 (FIG. 27), ovarian SKOV-3 (FIG. 28), Renal 786-O (FIG. 29), Melanoma G361 (FIG. 30) and Lung NCI-H596 (FIG. 31) cell lines.

Figure 33:
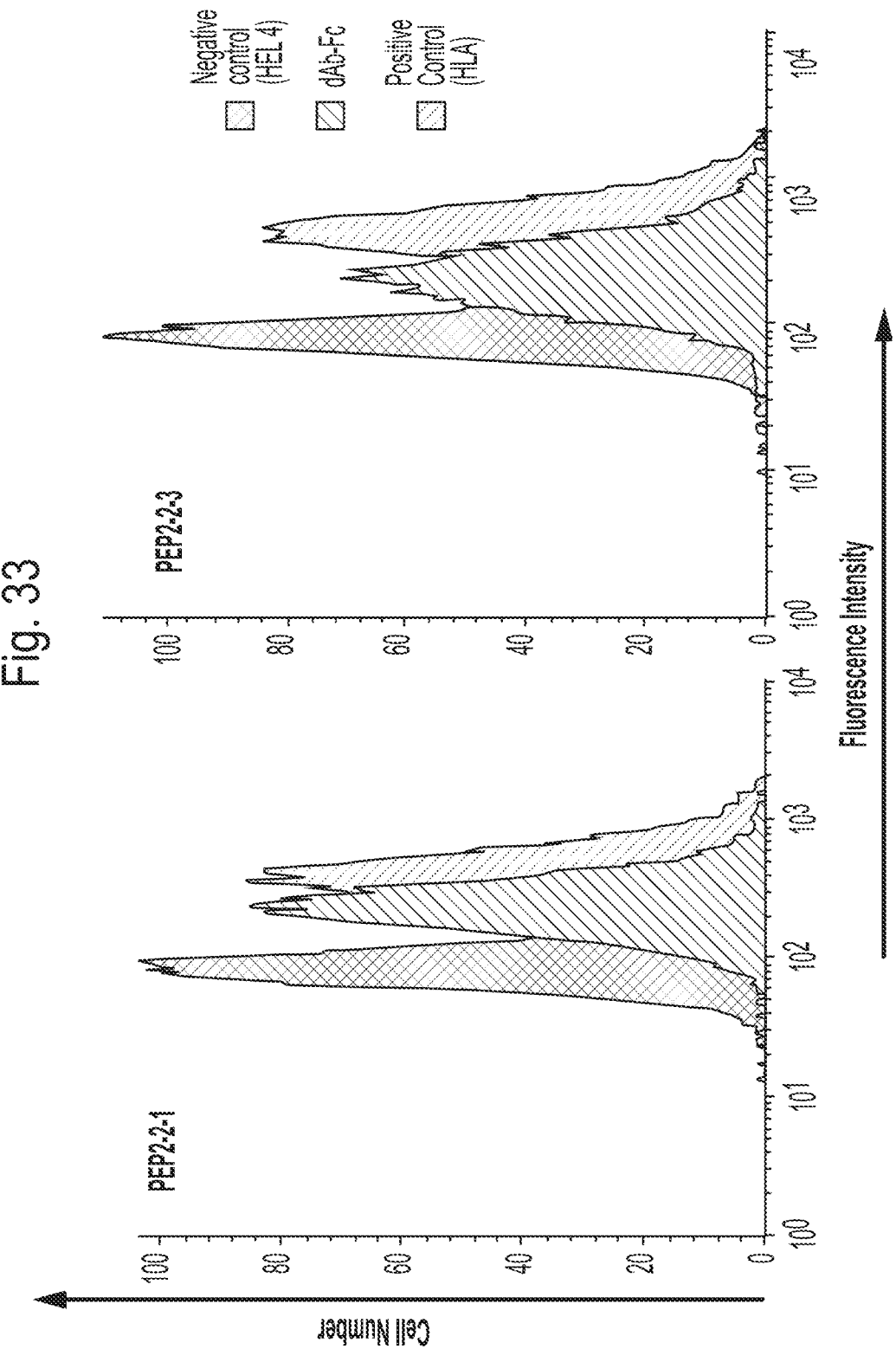
FIG. 33. Flow cytometry of prostate LNCap cells showing binding by PEP2-2-1 Fc, PEP2-2-3 Fc and HLA whereas the HEL4 control shows no binding above the secondary alone.

Non-crossreactivity with functional P2X$_7$ receptors on lymphocytes and monocytes was examined with flow cytometry. An example is shown in FIG. 32 in which the two dAb Fc clones PEP2-2-1 and PEP2-2-3 Fc showed no binding above the HEL4 Fc control background. In contrast, binding to live cancer cells such as prostate LNCap is clear (green in FIG. 33, with the HEL4 control in red showing no binding above the secondary and the HLA positive control shown in blue).

Figure 34:
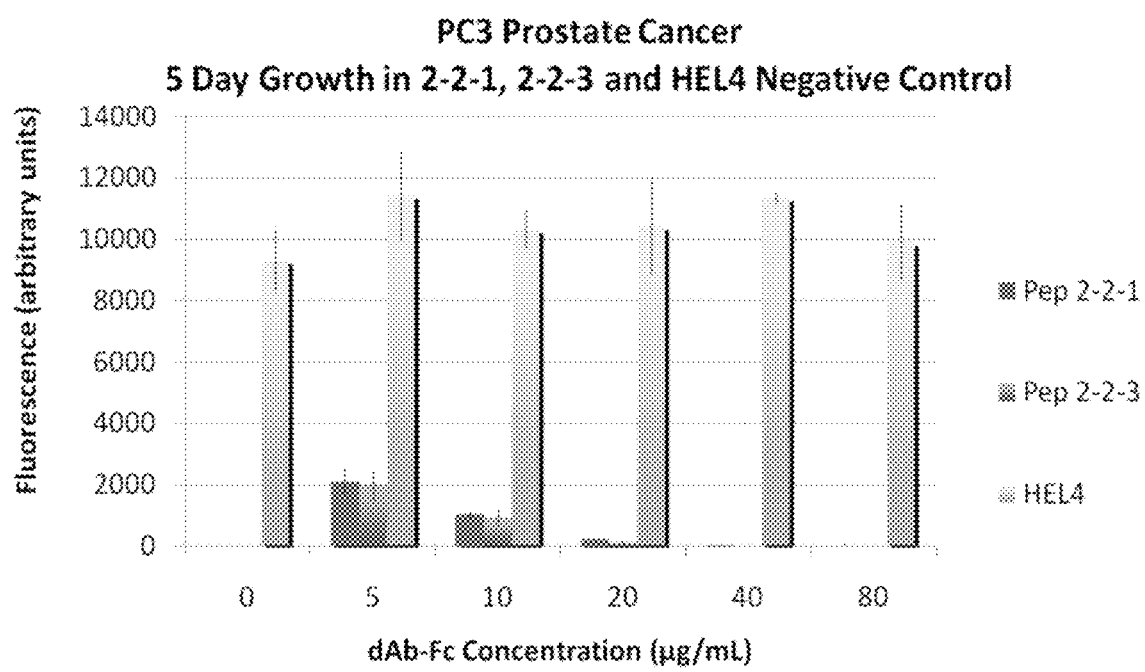
FIG. 34. CTB assay showing inhibition of PC3 cell growth over 5 days in the presence of increased PEP2-2-1 Fc and PEP2-2-3 Fc compared with control HEL4 Fc.
Figure 35:
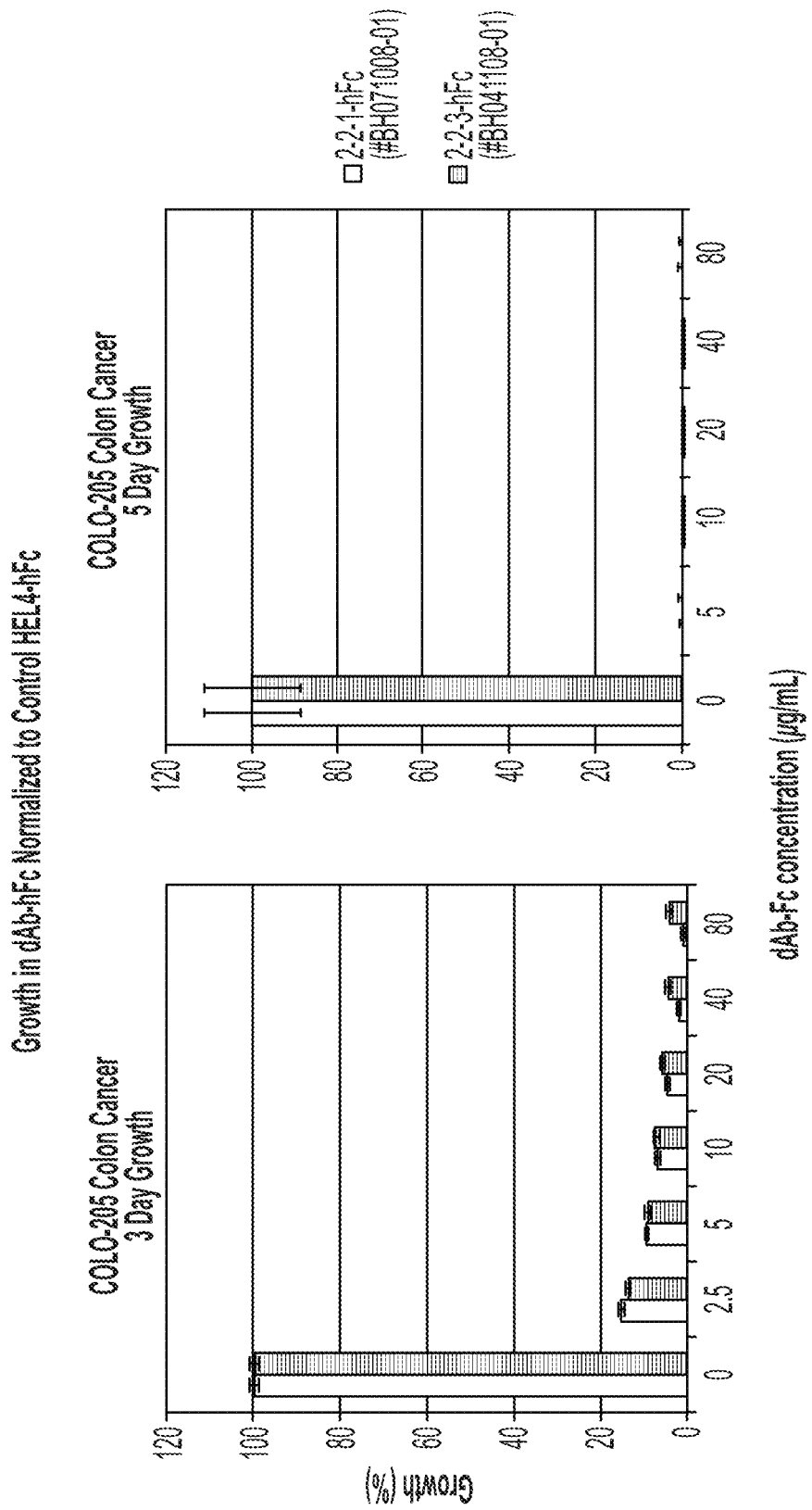
FIG. 35. CTB assay showing inhibition of COLO205 cell growth over 3 and 5 days in the presence of increased PEP2-2-1 Fc and PEP2-2-3 Fc compared with control HEL4 Fc.
Figure 36:
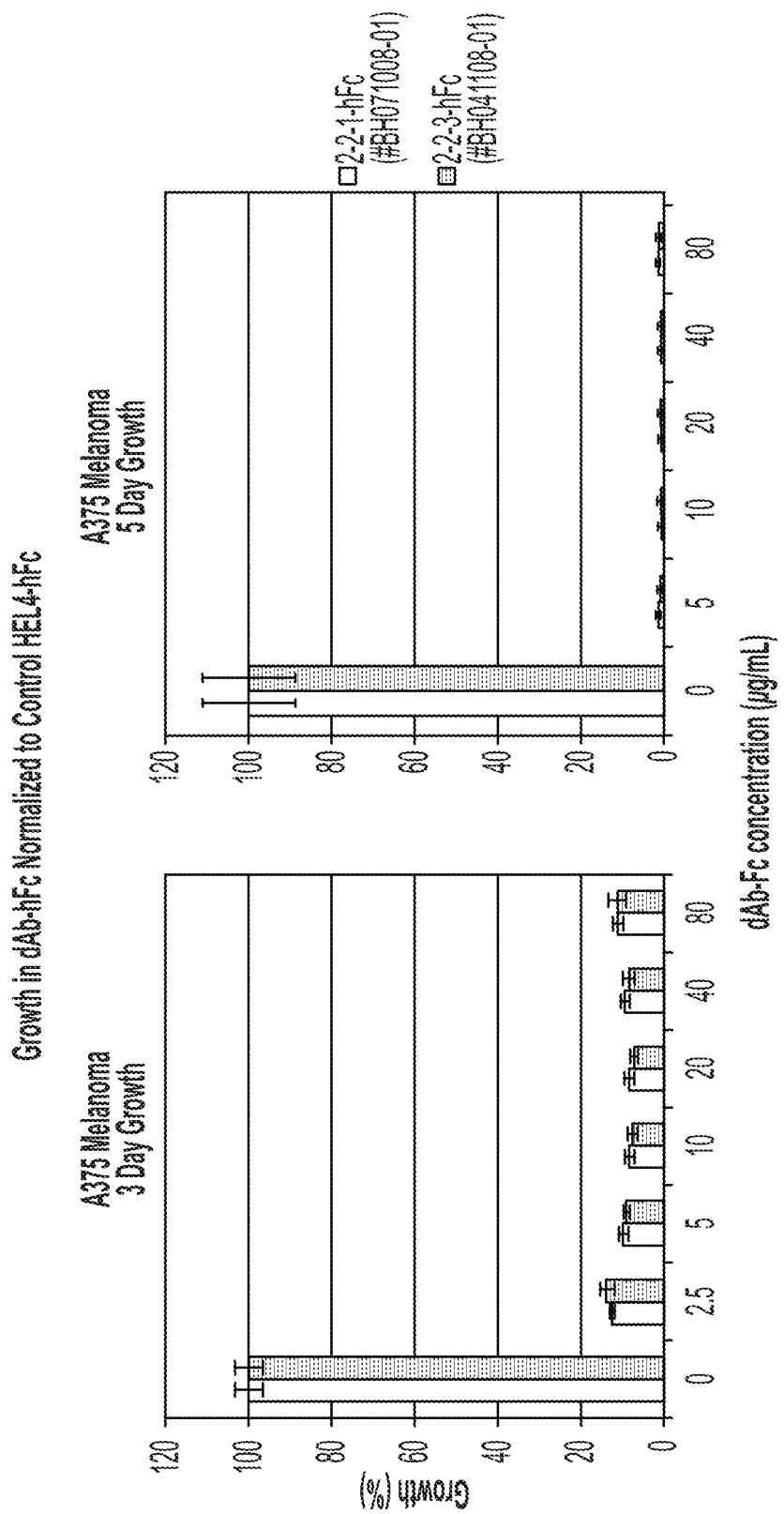
FIG. 36. CTB assay showing inhibition of A375 cell growth over 3 and 5 days in the presence of increased PEP2-2-1 Fc and PEP2-2-3 Fc compared with control HEL4 Fc FIG. 37. Biacore traces of PEP2-2-12 dAb domain tested at 10, 5, 2.5, 1 and 0.5 nM.
Figure 37:
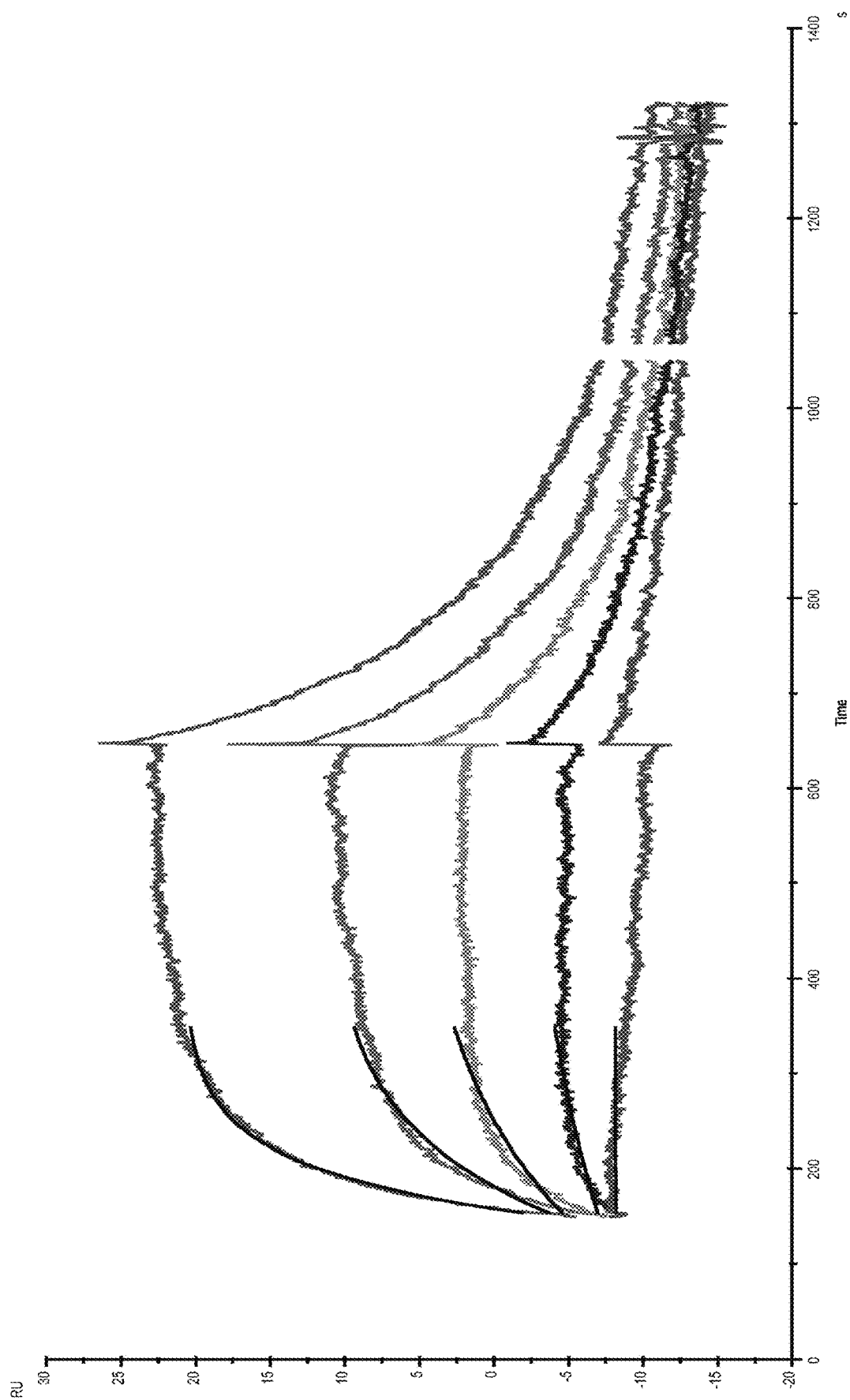

Direct cell killing or growth inhibition, as measured using the Cell Titer Blue Assay, was monitored with the lead clones PEP2-2-1 and PEP2-2-3 using a variety of cell lines. Over a 3 or 5 day growth cycle, the control cells grew while the net growth in the presence of the 2-2-1 Fc or 2-2-3 Fc was measured as a proportion of the growth in the presence of the HEL4 Fc control. FIG. 34 shows PC3 cell growth progressively inhibited as 2-2-1 or 2-2-3 are titrated up to 40 ug/mL over 5 days whereas the control cells are unaffected by HEL4 Fc. The colorectal cancer cell line COLO205 shows more sensitivity with both 2-2-1 and 2-2-3 Fc causing significant growth inhibition at 3 days while at 5 days, no cells remain even at 2.5 ug/mL (FIG. 35). Similarly the melanoma cell line A375 shows significant cell killing at 3 days while at 5 days no cells remain (FIG. 36).

Conclusion: Antigen binding sites that have high affinity for the non-functional P2X$_7$ receptor on live cells were identified, sequenced and biophysically characterised. Their effects on cell function were examined.

Example 6—Future Experiments

Objective: To further enhance affinity of the lead dabs through additional targeted NNS screening of residues involved in direct binding to the antigen and in residues enabling the CDRs to pack more efficiently. To improve stability and solubility of antigen binding sites by modifying the Fc. To improve the efficiency of cell killing.

Materials and methods: Standard techniques to enhance binding affinity such as additional rounds of NNS screening will be performed. The clones produced will be screened by Biacore to find those with improved off rates and phage ELISA against ECD2 (47-306). Additional screening using the CTB Assay will be performed to identify clones with the most efficient combination of binding affinity and killing capacity.

Expected results: Clones with at least one log lower binding constants are expected to be isolated that also kill cancer cells more efficiently than existing leads. As an example, new high affinity lead dAb domains (no Fc format) such as PEP2-2-12 in FIG. 36 show a KD against the ECD2 domain of 945 μM whereas the parent PEP2-2-1 exhibits a KD of 560 μM as an Fc construct with associated co-operative binding. The construction of leads with different Fc domains will enable the influence of the Fc on solubility properties and cell killing to be examined. Examples are the addition of mouse type IgG2a Fc in place of human IgG type 1 Fc.

Figure 38:
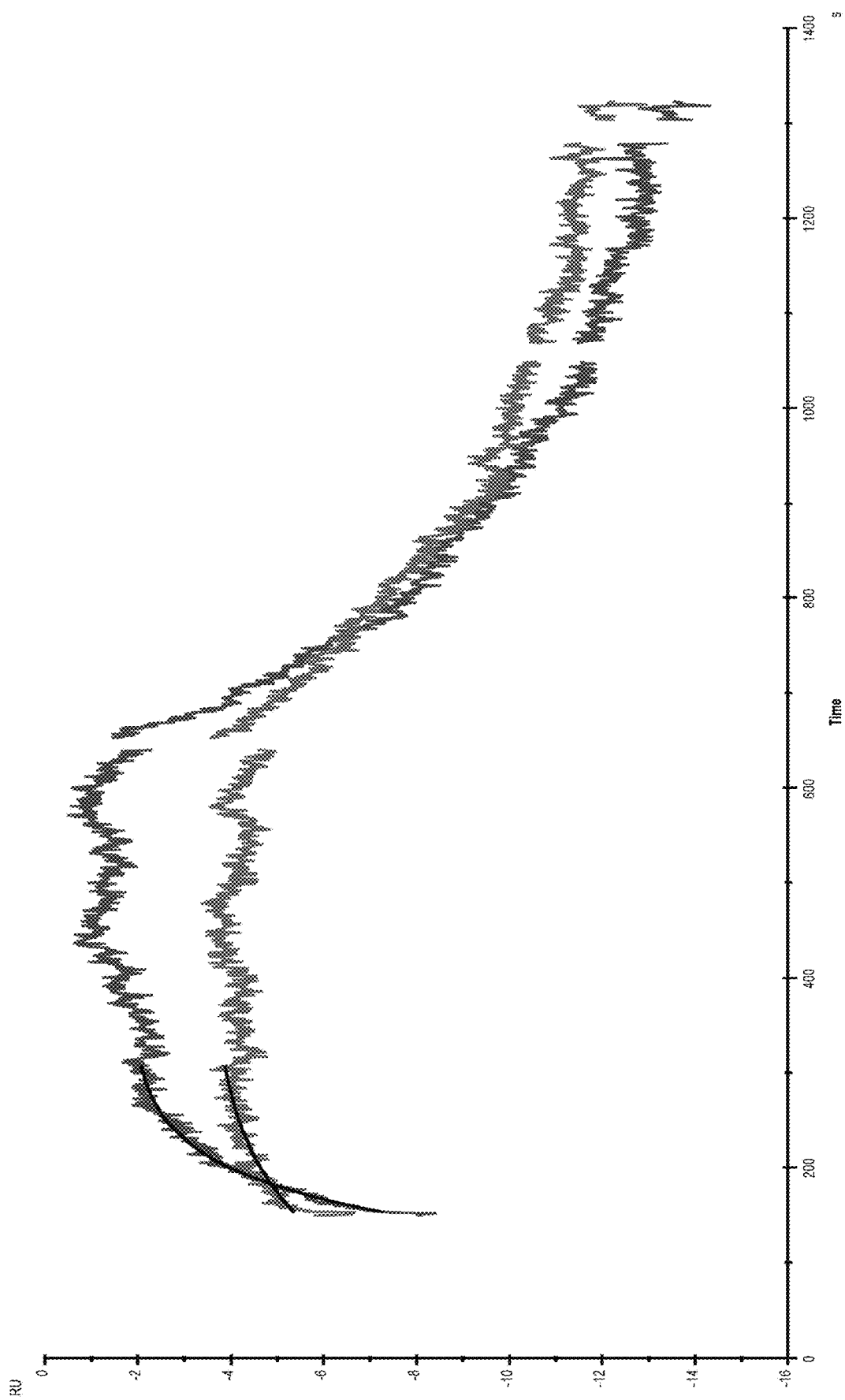
FIG. 38. Biacore traces of PEP2-2-12Alexa488 domain tested at 5 and 2.5 nM.
Figure 39:
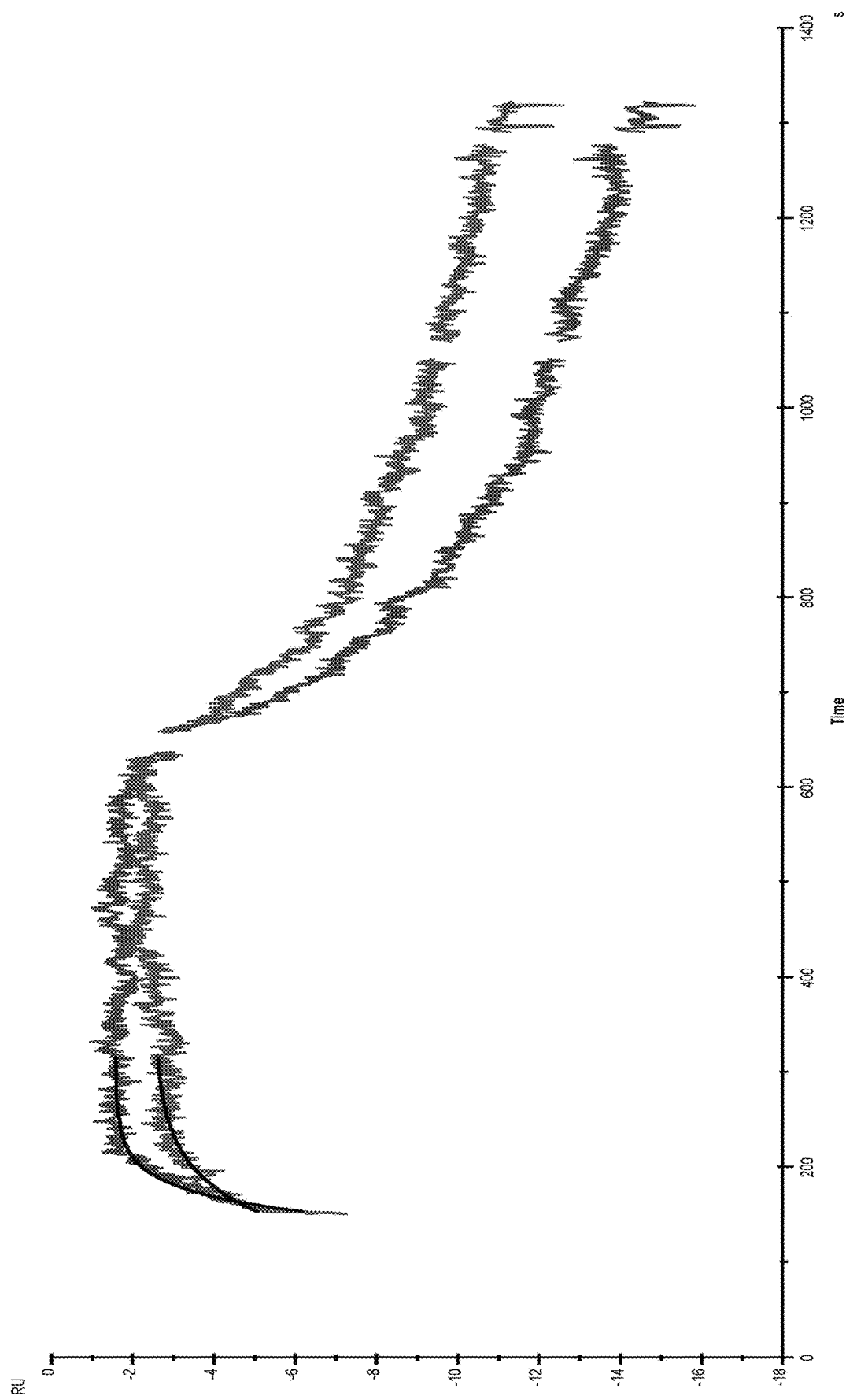
FIG. 39. Biacore traces of PEP2-472-12Alexa488 domain tested at 10 and 5 nM.
Figure 40:
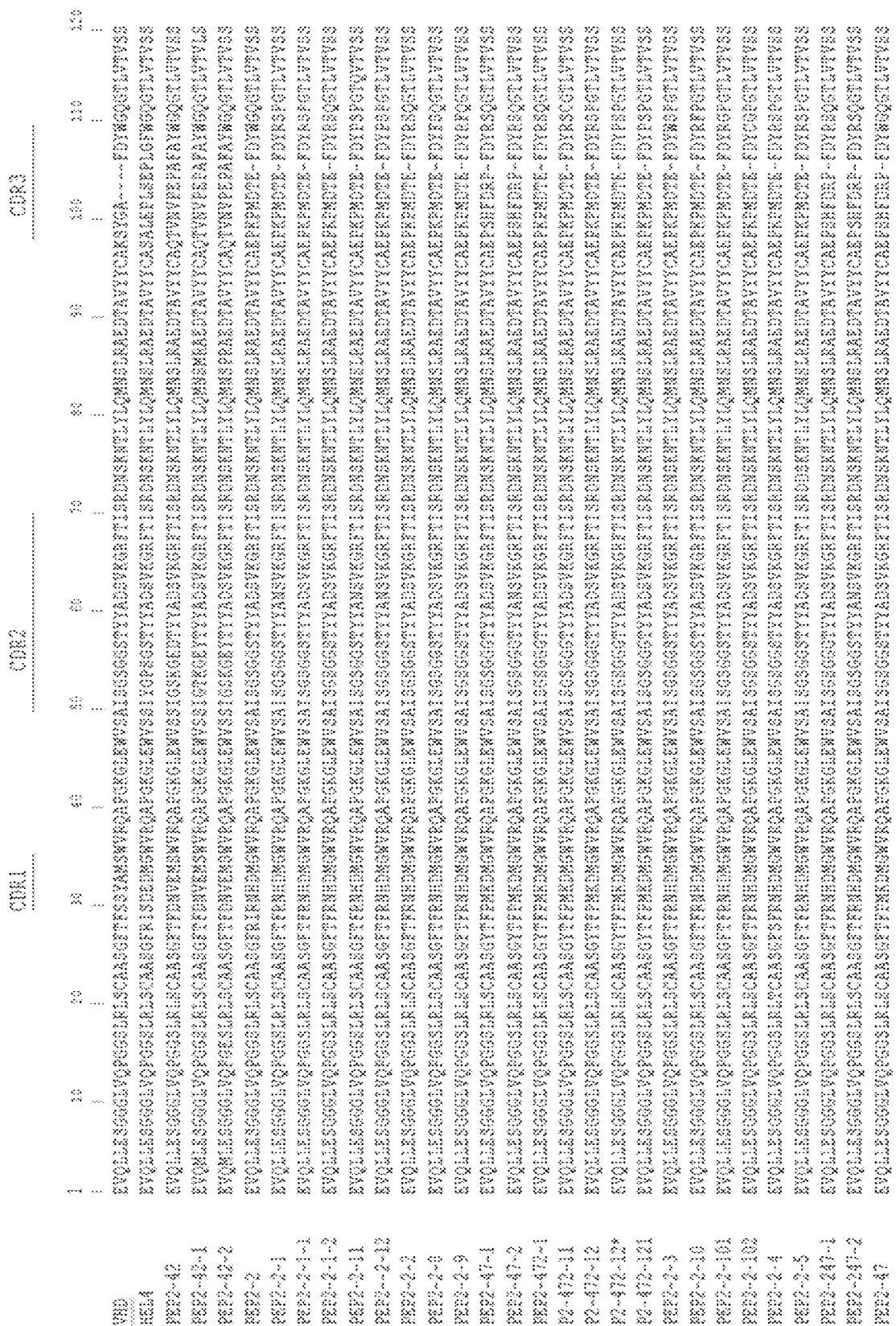
FIG. 40. Alignment of dAb sequences.
Figure 44:
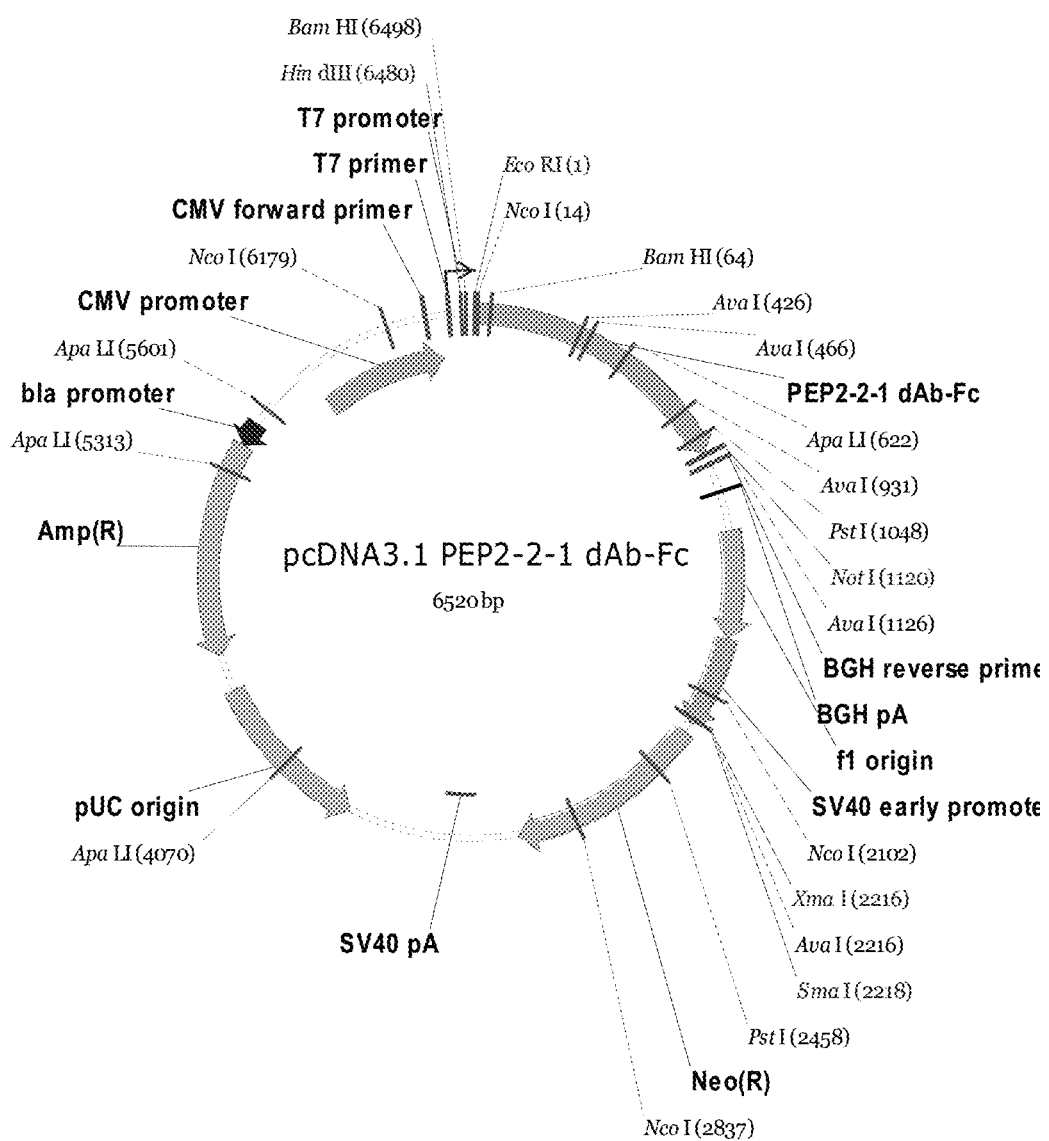
FIG. 44. Map of construct pcDNA3.1 PEP2-2-1 dAb-FC.

The labelling of high affinity single domain species would enable them to be used for systemic screening purposes. An example is shown in FIG. 38 in which an Alexa488 label has been attached to the dAb domain PEP2-2-12 and similar Biacore affinity determination suggests a K$_D$ of 174 pM. A high affinity lead with different parent is shown in FIG. 39 where PEP2-472-12Alexa488 domain is measured with a KD of 156 pM.

The invention claimed is:

1. A fusion protein comprising an antigen binding site for binding to a P2X$_7$ receptor, the antigen binding site being defined by general formula:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:

CDR1 has a sequence:
```
                                    (SEQ ID NO: 52)
RNHDMG;
```
CDR2 has a sequence:
```
                                    (SEQ ID NO: 53)
AISGSGGSTYYANSVKG;
```
CDR3 has a sequence:
```
                                    (SEQ ID NO: 57)
EPKPMDTEFDY.
```

2. The fusion protein comprising an antigen binding site for binding to a P2X$_7$ receptor according to claim 1, wherein FR1 has a sequence:
```
                                    (SEQ ID NO: 139)
EVQLLESGGGLVQPGGSLRLSCAASGFTF;
```
FR2 has a sequence:
```
                                    (SEQ ID NO: 145)
WVRQAPGKGLEWVS;
```
FR3 has a sequence:
```
                                    (SEQ ID NO: 148)
RFTISRDNSKNTLYLQMNSLRAEDTAVYYCA;
and
```
FR4 has a sequence:
```
                                    (SEQ ID NO: 162)
WSPGTLVTVSS, (SEQ ID NO: 153)
WGQGTLVTVSS, (SEQ ID NO: 155)
RSPGTLVTVSS, (SEQ ID NO: 157)
PSPGTLVTVSS, (SEQ ID NO: 158)
RSQGTLVTVSS, (SEQ ID NO: 159)
WSQGTLVTVSS, (SEQ ID NO: 160)
RGQGTLVTVSS, (SEQ ID NO: 161)
RFQGTLVTVSS, (SEQ ID NO: 163)
GSPGTLVTVSS, (SEQ ID NO: 164)
WGPGTLVTVSS, (SEQ ID NO: 165)
RGPGTLVTVSS, (SEQ ID NO: 166)
CGPGTLVTVSS
or
                    (residues 109-119 of SEQ ID NO: 182)
FSQGTLVTVSS.
```

3. The fusion protein comprising an antigen binding site according to claim 2, wherein FR4 has a sequence:
```
                                    (SEQ ID NO: 155)
RSPGTLVTVSS.
```

4. The fusion protein comprising an antigen binding site according to claim 2, wherein FR4 has a sequence
```
                                    (SEQ ID NO: 157)
PSPGTLVTVSS.
```

5. The fusion protein comprising an antigen binding site according to claim 1, wherein the antigen binding site is selected from the group consisting of an immunoglobulin variable domain (an Fv), an antibody, a single domain antibody (a dAb), a Fab, an scFv, a diabody or a triabody.

6. The fusion protein comprising an antigen binding site according to claim 1, wherein the fusion protein is an scFv.

7. The fusion protein according to claim 5, wherein the scFv is divalent or trivalent.

8. The fusion protein according to claim 1, wherein the fusion protein comprises a cellular ligand.

9. The fusion protein according to claim 1, wherein the fusion protein comprises a heterologous protein fused to the N-terminus or the C-terminus of the antigen binding site.

10. A nucleic acid comprising a nucleotide sequence encoding a fusion protein according to claim 1.

11. A genetically modified host cell including a nucleic acid according to claim 10.

12. The genetically modified host cell according to claim 11, wherein the nucleic acid is stably integrated into the genome of the cell.

13. The genetically modified host cell according to claim 12 wherein the cell is a eukaryotic cell.

14. A fusion protein according to claim 5, wherein the fusion protein comprises an scFv and the scFv comprises an effector protein fused at either the amino or the carboxy terminus of the scFv.

15. A method of treating a cancer that expresses nonfunctional $P2X_7$ receptor, the method comprising providing in a cell the fusion protein of claim 1 and administering the cell expressing the fusion protein to an individual in need of treatment for cancer, thereby treating the cancer.

16. A method of producing a cell capable of targeting a nonfunctional $P2X_7$ receptor present on the surface of a cancer cell, the method comprising transfecting a cell with a nucleic acid according to claim 10, culturing the cell to allow the fusion protein encoded by the nucleic acid to be presented on the surface of the cell, thereby producing a cell capable of targeting a nonfunctional $P2X_7$ receptor present on the surface of a cancer cell.

* * * * *